United States Patent
Kalayanov et al.

(10) Patent No.: US 8,592,429 B2
(45) Date of Patent: Nov. 26, 2013

(54) 5-AMINO-4-HYDROXYPENTOYL AMIDES

(75) Inventors: Genadiy Kalayanov, Huddinge (SE); Bart Rudolf Romanie Kesteleyn, Berlare (BE); Kevin Parkes, Little Chesterford (GB); Bengt Bertil Samuelsson, Huddinge (SE); Wim Bert Griet Schepens, Mechelen (BE); Johannes Wilhelmus J. Thuring, Beerse (BE); Hans Kristian Wallberg, Huddinge (SE); Jörg Kurt Wegner, Mechelen (BE)

(73) Assignee: Janssen R&D Ireland, Little Island, Co Cork (IE)

( * ) Notice: Subject to any disclaimer, the term of this patent is extended or adjusted under 35 U.S.C. 154(b) by 0 days.

(21) Appl. No.: 13/515,187

(22) PCT Filed: Dec. 10, 2010

(86) PCT No.: PCT/EP2010/069328
§ 371 (c)(1),
(2), (4) Date: Jun. 11, 2012

(87) PCT Pub. No.: WO2011/070131
PCT Pub. Date: Jun. 16, 2011

(65) Prior Publication Data
US 2012/0295920 A1   Nov. 22, 2012

(30) Foreign Application Priority Data

Dec. 11, 2009 (EP) ..................................... 09178979
May 10, 2010 (EP) ..................................... 10162370

(51) Int. Cl.
| | | |
|---|---|---|
| A61K 31/18 | (2006.01) | |
| A61K 31/17 | (2006.01) | |
| A61K 31/325 | (2006.01) | |
| A61K 31/38 | (2006.01) | |
| A61K 31/42 | (2006.01) | |
| A61K 31/44 | (2006.01) | |
| A61K 31/495 | (2006.01) | |

(52) U.S. Cl.
USPC .................................................. 514/255.05

(58) Field of Classification Search
USPC .................................................. 514/255.05
See application file for complete search history.

(56) References Cited

U.S. PATENT DOCUMENTS

2008/0249102 A1 * 10/2008 Ekegren et al. ............ 514/252.1

FOREIGN PATENT DOCUMENTS

WO   WO 2007048557 A1 * 5/2007
WO   WO 2007/147884 A1   12/2007

OTHER PUBLICATIONS

Mahlingam, A.K. et al., "HIV-1 Protease Inhibitors with a Transition-State Mimic Comprising a Tertiary alcohol: Improved Antiviral Activity in Cells"—J. Med. Chem. 2010, 53, 607-615.*
Becker, Stepen, "Atazanavir: Improving the HIV Protease Inhibitor Class", Expert Rev. Anti-Infect Ther, (2003), vol. 1, No. 3, pp. 403-413.
Fields, R.D., et al., "Dual-Attribute Continuous Monitoring of Cell Proliferation/Cytotoxicity", Am. Biotechnol. Lab, (1993), vol. 11, pp. 48-50.
Holloway, M.K., et al., "A Priori Prediction of Activity for HIV-1 Protease Inhibitors Employing Energy Minimization in the Active Site", J. Med. Chem., (1995), vol. 38, No. 2, pp. 305-317.
Miller, J.F., et al., "Ultra-Potent P1 Modified Arylsulfonamide HIV Protease Inhibitors: The Discovery of GW0385", Bioorganic & Medicinal Chemistry Letters, (2006), vol. 16, No. 7, pp. 1788-1794.
Wensing, A.M.J., et al., "Fifteen Years of HIV Protease Inhibitors: Raising the Barrier to Resistance", Antiviral Research, (2010), vol. 85, No. 1, pp. 59-74.
International Search report for Application No. PCT/EP2010/069328 mailed Feb. 22, 2011.

* cited by examiner

Primary Examiner — San-Ming Hui
Assistant Examiner — JeanMarie Calvillo
(74) Attorney, Agent, or Firm — Michael J. Atkins

(57) ABSTRACT

HIV inhibitors of formula (I) wherein $R^1$ is halo, $C_{1-4}$ alkoxy, trifluoromethoxy; $R^2$ is a group of formula (A); $R^3$ is a group of formula (B); $R^4$ is a group of formula (C); n is 0 or 1; A is CH or N; $R^5$ and $R^6$ are hydrogen, $C_{1-4}$ allyl, halo; $R^7$ and $R^8$ are $C_{1-4}$ allyl or $C_{1-4}$ alkoxy-$C_{1-4}$ alkyl; $R^9$ is $C_{1-4}$ allyl, cyclopropyl, trifluoromethyl, $C_{1-4}$ alkoxy, or dimethylamino; $R^{10}$ is hydrogen, $C_{1-4}$ alkyl, cyclopropyl, trifluoromethyl, $C_{1-4}$ alkoxy, or dimethylamino; pharmaceutically acceptable addition salts and solvates thereof; pharmaceutical compositions containing these compounds as active ingredient and processes for preparing said compounds.

21 Claims, No Drawings

5-AMINO-4-HYDROXYPENTOYL AMIDES

CROSS REFERENCE TO RELATED APPLICATIONS

This application is a national stage of PCT Application No. PCT/EP2010/069328, filed Dec. 10, 2010, which claims priority from European Patent Application No. 09178979.2, filed Dec. 11, 2009 and European Patent Application No. 10162370.0, filed May 10, 2010, all of which are hereby incorporated by reference in their entirety.

This invention concerns 5-amino-4-hydroxy-pentoyl amides having HIV (Human Immunodeficiency Virus) replication inhibiting properties, the preparation thereof and pharmaceutical compositions comprising these compounds.

Initially, treatment of HIV infection consisted of monotherapy with nucleoside derivatives and although successful in suppressing viral replication, these drugs quickly lost their effectiveness due to the emergence of drug-resistant strains. It became clear that a high mutation rate combined with rapid replication made HIV a particularly challenging target for antiviral therapy. The introduction of combination therapy of several anti-HIV agents improved therapeutic outcome. The current standard of care is the so-called HAART (Highly Active Anti-Retroviral Therapy), which offers a powerful and sustained viral suppression. HAART typically involves combinations of nucleoside or nucleotide reverse transcriptase inhibitors (NRTIs or NtRTIs respectively) with a non-nucleoside reverse transcriptase inhibitor (NNRTI) or a protease inhibitor (PI). Current guidelines for antiretroviral therapy recommend such triple combination therapy regimen even for initial treatment. Although HAART is capable of suppressing HIV up to undetectable levels, resistance can emerge due to compliance problems. It also has been shown that resistant virus is carried over to newly infected individuals, resulting in severely limited therapy options for these drug-naive patients.

Therefore there is a continued need for new and effective compounds that can be used as anti-HIV drugs. In particular, there is need for further HIV protease inhibitors that are more effective in terms of activity against wild type virus, but also against mutated strains, in particular toward mutated strains selected by the currently approved protease inhibitors. There is a need for protease inhibitors that are beneficial in terms of their pharmacokinetical profile, in particular that exhibit reduced plasma protein binding.

The present invention is aimed at providing particular novel series of 5-amino-4-hydroxy-pentoyl amides having HIV replication inhibiting properties.

The compounds of the invention differ from prior art compounds in structure, pharmacological activity and/or pharmacological potency. It has been found that they not only are very active against wild type virus, but also against mutant strains, in particular against strains that have become resistant to one or more known protease inhibitors, which strains are referred to as drug- or multidrug-resistant HIV strains.

Thus, in one aspect, the present invention concerns compounds of formulae I, including the stereochemically isomeric forms thereof, which can be represented by formula I:

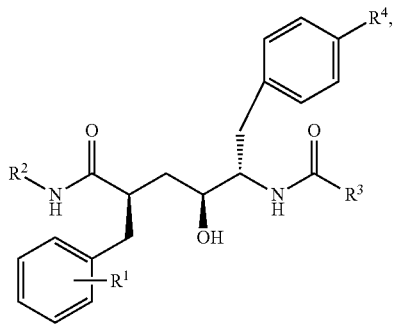

(I)

wherein $R^1$ is halo, $C_{1-4}$alkoxy, trifluoromethoxy;

$R^2$ is a group of formula:

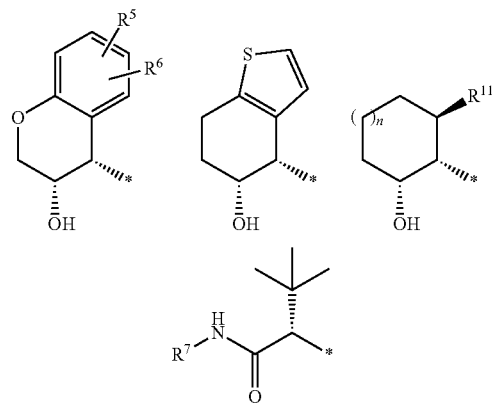

$R^3$ is a group of formula:

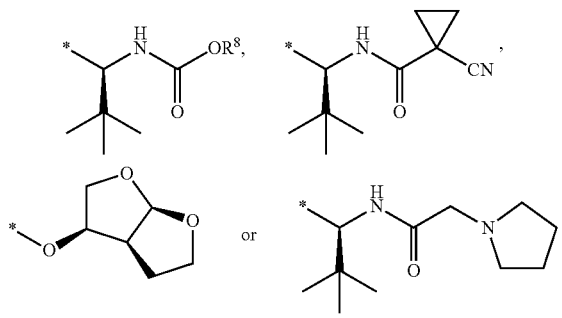

$R^4$ is a group of formula:

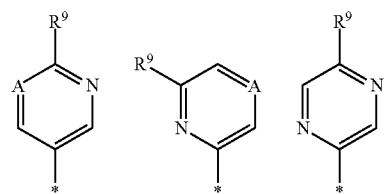

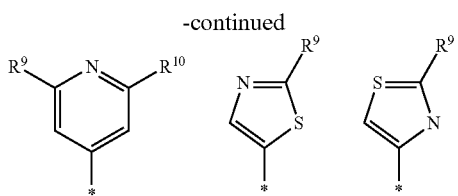

n is 0 or 1;
each A independently is CH or N;
$R^5$ and $R^6$ independently are hydrogen, $C_{1-4}$alkyl, or halo;
$R^7$ is $C_{1-4}$alkyl or $C_{1-4}$alkoxy$C_{1-4}$alkyl;
$R^8$ is $C_{1-4}$alkyl or $C_{1-4}$alkoxy$C_{1-4}$alkyl;
each $R^9$ independently is $C_{1-4}$alkyl, cyclopropyl, trifluoromethyl, $C_{1-4}$alkoxy, or dimethylamino;
$R^{10}$ is hydrogen, $C_{1-4}$alkyl, cyclopropyl, trifluoromethyl, $C_{1-4}$alkoxy, or dimethylamino;
$R^{11}$ is hydrogen or $C_{1-4}$alkyl;
the pharmaceutically acceptable addition salts and the pharmaceutically acceptable solvates thereof.

Whenever used in a molecular fragment or group, a bond with an asterisk (-*) represents the bond linking that fragment or group with the remainder of the molecule.

As used herein, $C_{1-4}$alkyl as a group or part of a group defines straight or branched chain saturated hydrocarbon radicals having from 1 to 4 carbon atoms such as methyl, ethyl, 1-propyl, 2-propyl, 1-butyl, 2-butyl, 2-methyl-propyl, t.butyl. Of interest among $C_{1-4}$alkyl is $C_{1-3}$alkyl or $C_{1-2}$alkyl; $C_{1-3}$alkyl defines straight or branched chain saturated hydrocarbon radicals having from 1 to 3 carbon atoms; $C_{1-2}$alkyl defines methyl or ethyl.

The term "halo" is generic to fluoro, chloro, bromo or iodo, in particular to fluoro or chloro.

Whenever a radical occurs in the definition of the compounds of formula I or in any of the subgroups of compounds of formula I specified herein, said radical independently is as specified above in the definition of the compounds of formula I or in the more restricted definitions as specified hereinafter.

It should also be noted that the radical positions on any molecular moiety used in the definitions may be anywhere on such moiety as long as it is chemically stable. For instance radical $R^1$ may be on any position of the phenyl to which it is attached.

When any variable (e.g. halogen, $C_{1-4}$alkyl) occurs more than once in any moiety, each definition is independent. Any limited definitions of the radicals specified herein are meant to be applicable to the group of compounds of formula I as well as to any subgroup defined or mentioned herein. Lines drawn from substituents into ring systems indicate that the bond may be attached to any of the suitable ring atoms.

The pharmaceutically acceptable addition salt forms, which the compounds of the present invention are able to form, can conveniently be prepared using the appropriate acids, such as, for example, inorganic acids such as hydrohalic acids, e.g. hydrochloric or hydrobromic acid, sulfuric, hemisulphuric, nitric, phosphoric, and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic, and the like acids. Conversely said acid addition salt forms can be converted into the free base form by treatment with an appropriate base.

The compounds of formula I containing acidic protons may be converted into their pharmaceutically acceptable metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary, and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term "pharmaceutically acceptable solvate" is meant to comprise hydrates and solvent addition forms that the compounds of formula I, including stereoisomeric forms thereof, can form. Examples of such solvates are e.g. hydrates, alcoholates, such as ethanolates, i.propanolates, n.propanolates, and the like.

The compounds of formula I thereof may contain one or more centers of chirality and may exist as stereochemically isomeric forms. Of special interest are those compounds of formula I that are stereochemically pure. The term "stereochemically isomeric forms" as used herein defines all the possible stereoisomeric forms of the compounds of formula I, the pharmaceutically acceptable addition salts thereof, and the pharmaceutically acceptable solvates thereof. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula I, the pharmaceutically acceptable addition salts thereof, and the pharmaceutically acceptable solvates thereof substantially free, i.e. associated with less than 10%, preferably less than 5%, in particular less than 2% and most preferably less than 1% of the other isomers. Stereogenic centers may have the R- or S-configuration; substituents on bivalent cyclic (partially) saturated radicals may have either the cis- or trans-configuration; double bonds can have an E (entgegen) or Z (zusammen)-stereochemistry.

Some of the compounds of formula I may also exist in their tautomeric form. Such forms although not explicitly indicated in the above formula are intended to be included within the scope of the present invention.

The present invention is also intended to include any isotopes of atoms present in the compounds of the invention. For example, isotopes of hydrogen include tritium and deuterium and isotopes of carbon include $^{13}C$ and $^{14}C$.

Whenever used hereinabove or hereinafter, the terms "compounds of formula I", "the present compounds", "the compounds of the present invention" or any equivalent terms, and similarly, the terms "subgroups of compounds of formula I", "subgroups of the present compounds", "subgroups of the compounds of the present invention" or any equivalent terms, are meant to include the compounds of general formula I, or subgroups of the compounds of general formula I, as well as their salts, solvates, and stereoisomers.

Whenever mention is made hereinbefore or hereinafter that substituents can be selected each independently out of a list of definitions, such as for example for $R^1$ or $R^2$, any possible combinations are intended to be included that are chemically possible or that lead to molecules of such chemical stability that they can be processed in standard pharmaceutical procedures.

Particular subgroups of the compounds of formula I or any subgroup of compounds of formula I specified herein wherein
(a) $R^1$ is halo; or $R^1$ is fluoro or chloro; which halo (or fluoro or chloro) in particular is substituted in ortho position; or
(b) $R^1$ is methoxy; which methoxy in particular is substituted in meta position.

Particular subgroups of the compounds of formula I or any subgroup of compounds of formula I specified herein wherein
(a) $R^2$ is a group of formula

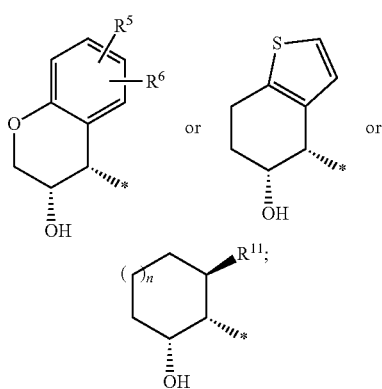

(b) or wherein $R^2$ is a group of formula:

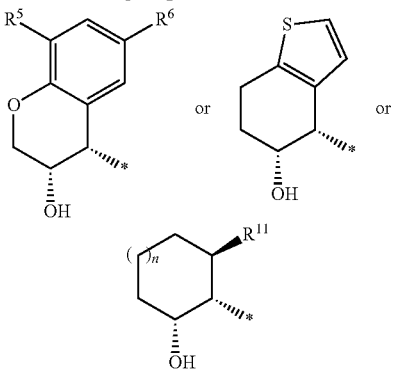

Further embodiments of the present invention are those compounds of formula I or any of the subgroups of compounds of formula I wherein $R^5$ is hydrogen, and $R^6$ is halo or $C_{1-4}$alkyl; $R^5$ is halo and $R^6$ is hydrogen; $R^5$ is halo or $C_{1-4}$alkyl, and $R^6$ is hydrogen; or $R^5$ and $R^6$ are both hydrogen, or are both halo.

Further embodiments of the present invention are those compounds of formula I or any of the subgroups of compounds of formula I wherein in the definitions of $R^5$ and $R^6$ halo is fluoro or chloro, and $C_{1-4}$alkyl is methyl.

Particular embodiments of the present invention are those compounds of formula I or any of the subgroups of compounds of formula I, including the compounds wherein $R^2$ is as defined above under (a) or (b), wherein $R^5$ is hydrogen and $R^6$ is fluoro or chloro; $R^5$ is fluoro or chloro and $R^6$ is hydrogen; $R^5$ is hydrogen and $R^6$ is methyl; $R^5$ and $R^6$ are both hydrogen, or $R^5$ is chloro and $R^6$ is fluoro; more in particular wherein $R^5$ is hydrogen and $R^6$ is fluoro; $R^5$ is chloro and $R^6$ is hydrogen; $R^5$ is hydrogen and $R^6$ is methyl; $R^5$ and $R^6$ are both hydrogen, $R^5$ is chloro and $R^6$ is fluoro, $R^5$ is methyl and $R^6$ is fluoro, or $R^5$ is fluoro and $R^6$ is methyl.

Embodiments of the present invention are those compounds of formula I or any of the subgroups of compounds of formula I wherein $R^3$ is a group of formula

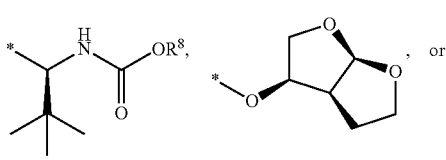

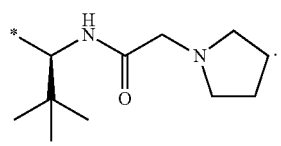

A further embodiment concerns those compounds of the invention wherein $R^3$ is a group of formula

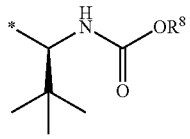

Embodiments of the present invention are those compounds of formula I or any of the subgroups of compounds of formula I wherein $R^8$ is methyl or 2-methoxyethyl; or wherein $R^8$ is methyl.

Embodiments of the present invention are those compounds of formula I or any of the subgroups of compounds of formula I wherein $R^9$ is $C_{1-2}$alkoxy or dimethylamino; or $R^9$ is methoxy or dimethylamino; or $R^9$ is methoxy.

Embodiments of the present invention are those compounds of formula I or any of the subgroups of compounds of formula I wherein $R^4$ is a group having the chemical structure specified above, but wherein in the first group $R^9$ is $R^{9a}$ in the second group $R^9$ is $R^{9b}$ in the third group $R^9$ is $R^{9c}$ in the fourth group $R^9$ is $R^{9d}$ in the fifth and in the sixth group $R^9$ is $R^{9e}$; which groups therefore can be represented as follows:

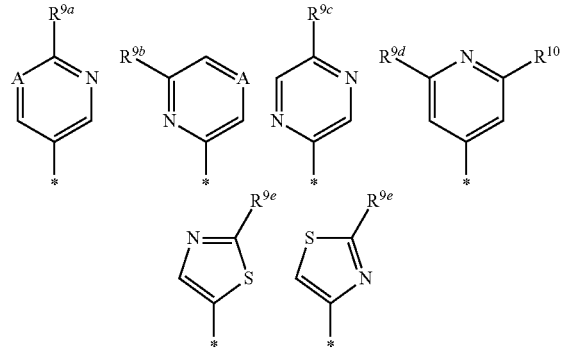

wherein each A independently is CH or N; or wherein each A is CH;

$R^{9a}$ is $C_{1-4}$alkoxy or dimethylamino;

$R^{9b}$ is $C_{1-4}$alkoxy or dimethylamino;

$R^{9c}$ is $C_{1-4}$alkoxy or dimethylamino;

$R^{9d}$ is $C_{1-4}$alkyl, cyclopropyl, trifluoromethyl;

$R^{10}$ is hydrogen, hydrogen, $C_{1-4}$alkyl, cyclopropyl, or trifluoromethyl; or $R^{10}$ is hydrogen, methyl, cyclopropyl, or trifluoromethyl;

each $R^{9e}$ independently is $C_{1-4}$alkyl, cyclopropyl, $C_{1-4}$alkoxy, or dimethylamino.

Of particular interest are those compounds wherein in $R^{9a}$, $R^{9b}$, $R^{9c}$, $R^{9d}$, or $R^{9e}$ $C_{1-4}$alkoxy is methoxy and $C_{1-4}$alkyl is methyl.

In further embodiment $R^4$ is a group having the chemical structure:

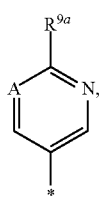

wherein A is CH and $R^{9a}$ is methoxy or dimethylamino.

Embodiments of the present invention are those compounds of formula I or any of the subgroups of compounds of formula I wherein $R^{11}$ is $C_{1-4}$alkyl; or wherein $R^{11}$ is methyl.

One embodiment concerns the compounds 1-102 listed in Table I at the end of the experimental part, including the pharmaceutically acceptable salts and solvates thereof. A particular embodiment concerns the free form (non pharmaceutically acceptable salts and solvates) of the compounds 1-102 listed in Table I.

Of particular interest are the compounds with numbers 7, 8, 52, 67, 91, 93, 96, 101 and 102 listed in the table at the end of the examples including the pharmaceutically acceptable salts and solvates thereof.

The compounds of formula I wherein $R^3$ is a group of formula:

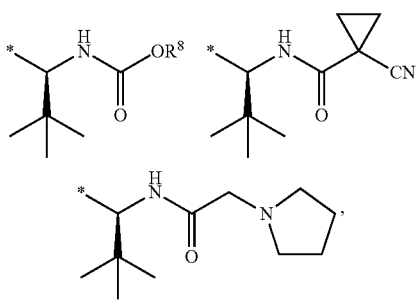

said compounds being represented by formula I-a can be prepared by coupling an intermediate of formula II with a carboxylic acid derivative of formula III in an amide forming reaction. The reaction conditions for this amide forming reaction are those used to couple amino acids in peptide synthesis. Coupling agents that may be used can be selected from N-ethoxycarbonyl-2-ethoxy-1,2-dihydroquinoline (EEDQ), N-isobutoxycarbonyl-2-isobutoxy-1,2-dihydroquinoline (IIDQ), N,N,N',N'-tetramethyl-O-(7-azabenzotriazol-1-yl)uronium hexafluorophosphate (HATU), benzotriazole-1-yl-oxy-tris-(dimethylamino)-phosphonium hexafluorophosphate (BOP), benzotriazol-1-yl-oxy-tris-pyrrolidino-phosphonium hexafluorophosphate (PyBOP®), dicyclohexylcarbodiimide (DCC), 3-ethyl-1(N,N-dimethyl)aminopropylcarbodiimide (EDCI), or 1,3-diisopropylcarbodiimide. A catalyst may be added, for example 1-hydroxybenzotriazole (HOBt) or 4-dimethylaminopyridine (DMAP). The reaction is usually conducted in the presence of a base, in particular an amine base such as a tertiary amine, e.g. triethylamine, N-methylmorpholine, N,N-diisopropylethylamine, (the latter also being referred to as or Hünig's base, DIPEA, or DIEA). Solvents that can be used include bipolar aprotic solvents such as DMA, DMF or acetonitrile, halogenated hydrocarbons such as $CH_2Cl_2$ or $CHCl_3$, ether solvents such as THF. In one embodiment, the coupling reaction is conducted with HATU using triethylamine as base in DMF.

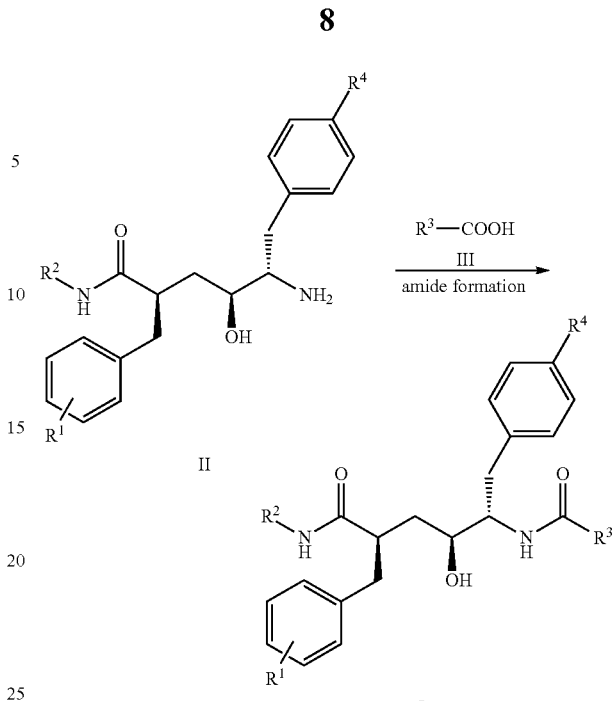

Compounds of formula I wherein $R^3$ is

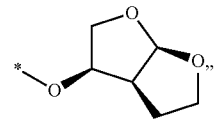 [SMILES: *O[C@H]1CO[C@H]2OCC[C@H]21]

wherein being represented by formula I-b, can be prepared by an urethane forming reaction of an intermediate of formula II with an appropriate electrophilic carbonyl compound of formula IV such as a chloroformate, or an activated 2,5-dioxopyrrolidin-1-olate, para-nitrophenolate or 2-pyridyl carbonate.

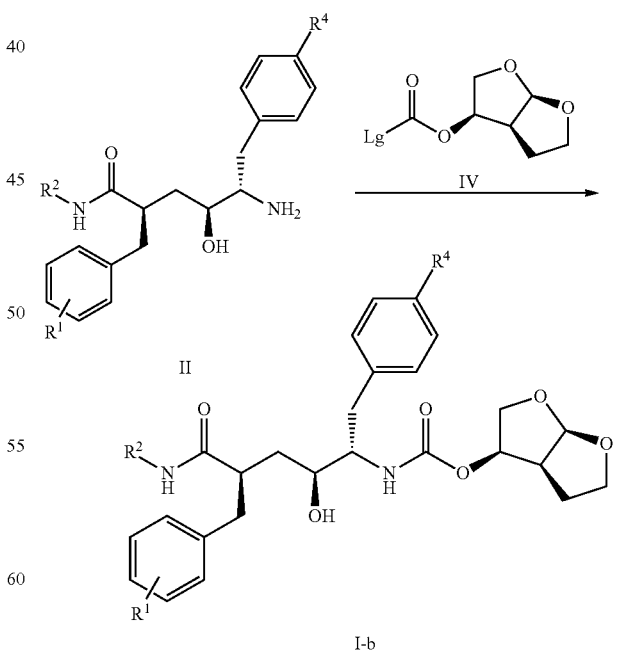

Lg in the above scheme is a leaving group such as chloro, bromo, 2,5-dioxopyrrolidin-1-olate, para-nitrophenolate.

The intermediates of formula II in turn can be prepared as outlined in the following reaction scheme:

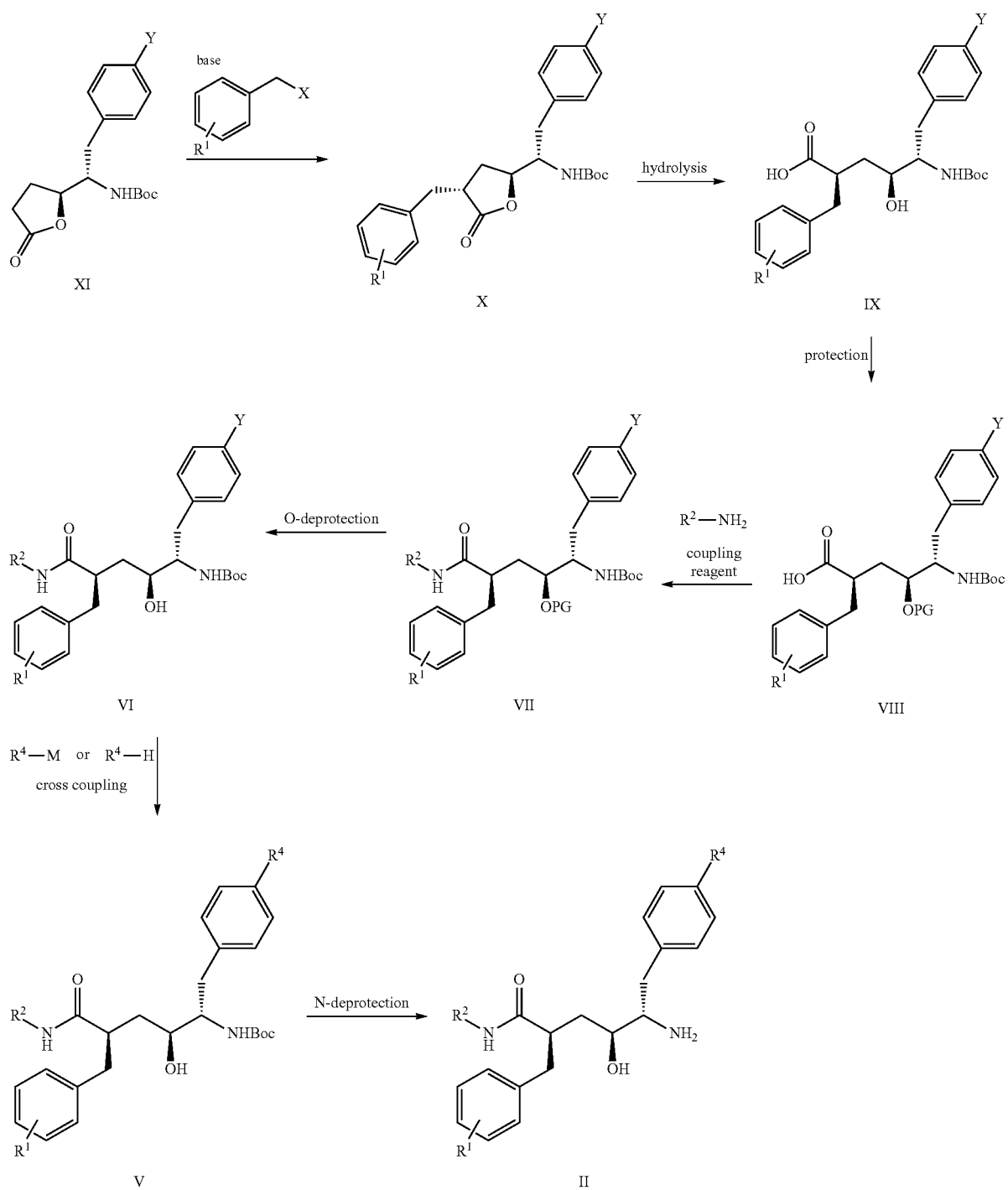

In the above scheme M represents a —B(OR$^a$)$_2$ group or a —Sn(R$^b$)$_3$ group, wherein R$^a$ represents a hydrogen or an alkyl or alkanediyl group, e.g. 2,3-dimethyl-2,3-butanediyl and R$^b$ represents an alkyl group such as methyl or butyl. PG represents a hydroxy-protecting group that can be selectively cleaved in the presence of the Boc group. Y represents bromo, iodo or a trifluoromethanesulfonyl (triflate or TfO—) group. X represents chloro, bromo, or iodo.

The triflate group can be introduced by reacting an intermediate of formula X bearing a hydroxy group at the position of the bromo with a trifluoromethanesulfonimide, in the presence of a base in a solvent such as dichloromethane. The intermediate of formula X bearing a hydroxy group in turn can be prepared from an intermediate XI bearing a protected hydroxy group at the position of the group Y, following the procedures described hereinafter for the conversion of XI to X, followed by a deprotection step. A protecting group that can be used in this procedure is a benzyl group, which can be removed with hydrogen in the presence of a catalyst.

In a first step, the lactone XI is alkylated with a benzyl halide to the benzylated lactone X. This reaction is conducted in an aprotic solvent such as THF, with a base, e.g. lithium bis(trimethylsilyl)amide, sodium bis(trimethylsilyl)amide, or lithium diisopropylamide at low temperature, e.g. at −78° C., followed by the addition of the benzyl halide. The lactone in the intermediates X is ring-opened by hydrolysis using a base such as LiOH, NaOH, or KOH in an aqueous solvent such as a mixture of DMF, DMA, dioxane, THF and water. This hydrolysis results in intermediates IX wherein subsequently the alcohol function is protected with a suitable protecting group PG, for example with a silyl group such as triisopropylsilyl, t-butyldimethylsilyl or the like, under art-known conditions, to generate intermediates of formula VIII. The carboxyl function is converted to the corresponding amide in VII, by coupling reaction of intermediate VIII with a primary amine of formula $R^2$—$NH_2$. The conditions for this reaction are as described above. Optionally $R^2$—$NH_2$ can be used in racemic form and the resulting diastereoisomeric mixture of intermediates VII can be separated, e.g. by chromatography.

In a next step the O-protecting group in VII is removed yielding intermediates VI. For example in case of a t-butyldimethylsilyl group use can be made of tetrabutylammonium fluoride (TBAF) or HF in acetonitrile. The intermediates VI, which can be bromo, iodo or triflate (—OTf) derivatives, are then subjected to a carbon-carbon cross-coupling reaction such as a Suzuki, Stille, Heck, or Negishi reaction that is metal-catalysed (usually with Pd, Ni or Cu catalysts). One example of such cross-coupling reaction is the Suzuki reaction, in which case VI is reacted with a substituted heteroaryl boronic acid or ester (e.g. pinacolatoboronate) in the presence of a palladium catalyst at elevated temperature The reaction is carried out in the presence of a base such as sodium bicarbonate, sodium carbonate, sodium hydroxide, potassium carbonate, cesium carbonate, potassium phosphate, etc. When an inorganic base is difficult to dissolve in an organic solvent, it is used as an aqueous solution. Another such cross-coupling reaction is the Stille reaction in which case VI is reacted with a substituted heteroaryl stannane at elevated temperature in the presence of a palladium catalyst. A metal salt like lithium chloride, lithium bromide or lithium iodide can be used as an additive. Palladium catalysts suitable for the Suzuki or Stille reactions comprise $Pd(PPh_3)_4$ (Ph=phenyl), $Pd_2(dba)_3$ (dba=dibenzylideneacetone), $Pd(OAc)_2$, $Pd(dppf)Cl_2$ (dppf=1,1'-bis(diphenylphosphino) ferrocene). In some cases additional ligands (e.g. tri-t-butylphospine, 1,1'-bis(diphenylphospino)ferrocene, tri-o-tolylphospine or the like) may be added to facilitate the coupling reaction. Still another such a reaction is the Heck reaction which is the reaction of an unsaturated halide (or triflate) with an alkene and a base and palladium catalyst to form a substituted alkene. In the present case it involves a palladium catalysed cross-coupling between an aryl halide or triflate and a thiazole. A suitable catalyst for this reaction is $Pd(PPh_3)_4$. Suitable organic solvents for this type of reactions include tetrahydrofuran, 1,4-dioxane and 1,2-dimethoxyethane, aromatic solvents such as benzene or toluene, alcohol solvents such as methanol or ethanol, acetonitrile, dimethylformamide, or a mixture of these solvents. A base that can be used is an alkali metal acetate such as potassium acetate.

Removal of the Boc N-protecting group in V, for example by acidic treatment using trifluoroacetic acid in a halogenated solvent such as $CH_2Cl_2$, or hydrochloric acid in isopropanol finally leads to intermediate II. The Boc-deprotection can also be accomplished by treatment of intermediate V with trimethylsilyl iodide or a mixture of trimethylsilyl chloride and NaI in an appropriate solvent e.g. acetonitrile, $CHCl_3$ or $CH_2Cl_2$. The Boc-deprotection reactions preferably are conducted at room temperature.

The intermediates of formula XI can be prepared as in the following reaction scheme wherein Y is as specified above and PG is a N-protecting group such as a BOC-group.

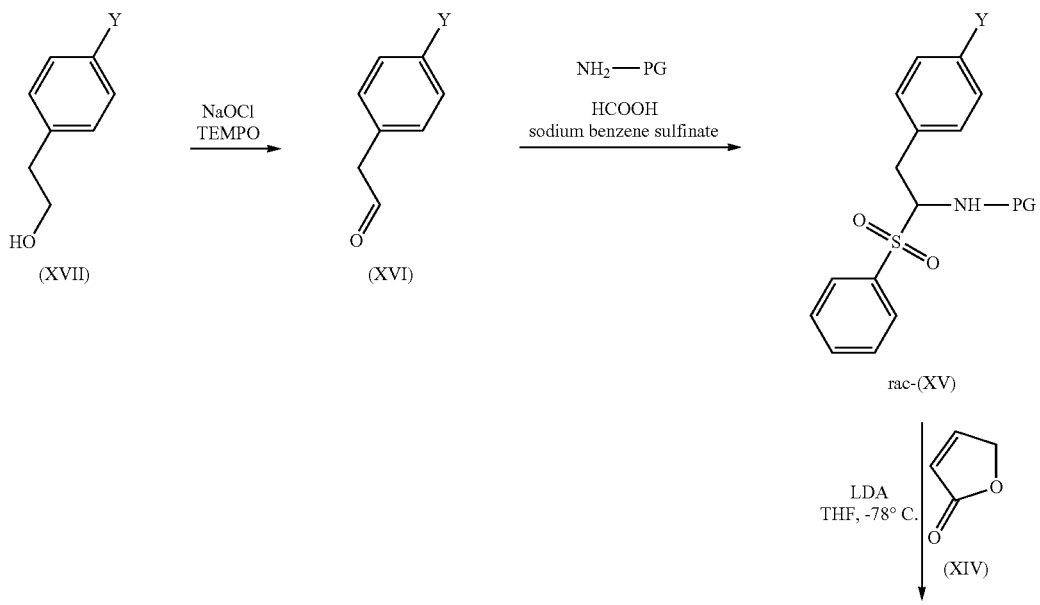

-continued

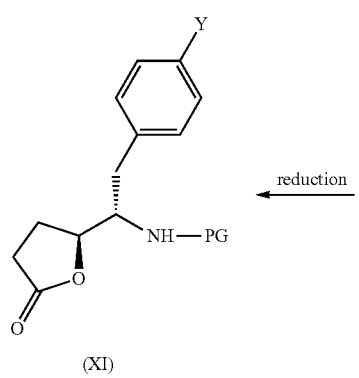
(XI)

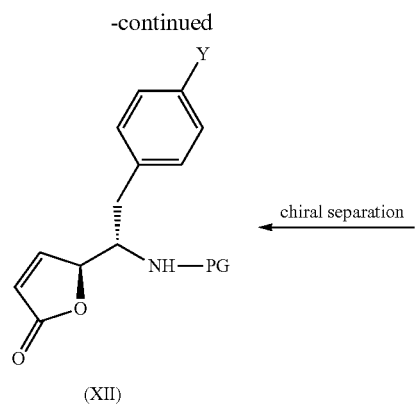
(XII)

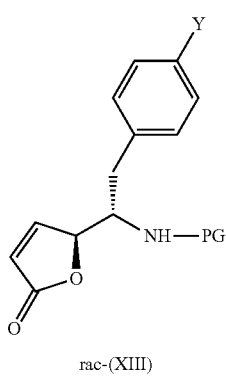
rac-(XIII)

In a first step, the alcohol function in the 2-phenethyl alcohol XVII is oxidized to the corresponding acetaldehyde XVI using a weak oxidant such as sodium hypochlorite in the presence of 2,2,6,6-tetramethylpiperidine-1-oxyl (or TEMPO), which is a selective oxidant generating aldehydes from primary alcohols. In a next step the acetaldehyde XVI is reacted with a protected amine and with a benzene sulfinate. Reaction of the thus obtained sulfone XV with lactone XIV yields the lactone derivative XIII, which is separated with chiral chromatography to enantiomeric pure XII, wherein the double bond is reduced, for example with hydrogen in the presence of Raney Ni.

Where appropriate, the synthetic steps in the preparation of compounds according to formula II, can be performed in another order. For example, the cross-coupling reaction can be carried out at various stages in the synthetic sequence in the above scheme, such as on intermediates VI, VII, VIII, IX and XI. The cross coupling can be even performed at a later stage of the synthesis, for example at the end of the synthesis as illustrated in the following reaction scheme. In this scheme, M is as specified above and the cross-coupling reaction conditions also are as described above. Intermediates XVIII can be prepared following the procedures for the preparation of intermediates II, but without cross-coupling reaction, followed by a coupling reaction to introduce the $R^3$—CO-group.

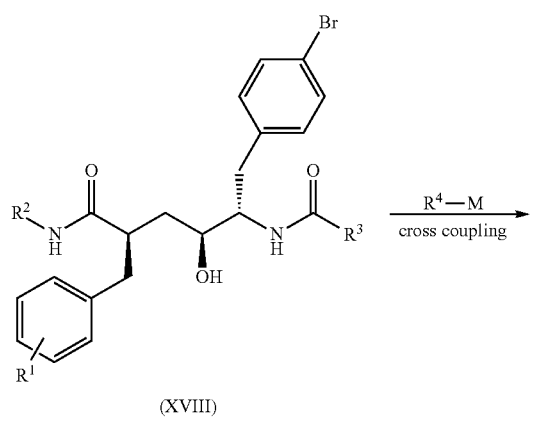
(XVIII)

-continued

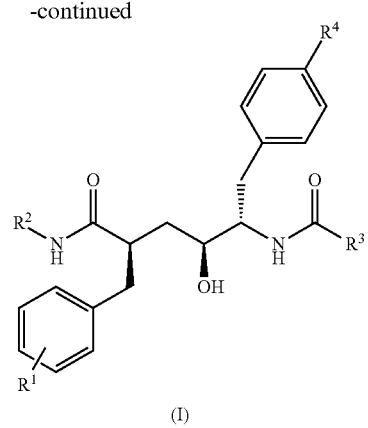
(I)

The compounds of formula I wherein $R^3$ is a group of formula:

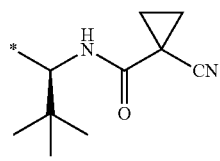 [SMILES: *[C@@H](NC(=O)C1(C#N)CC1)C(C)(C)C]

said compounds being represented by formula I-c can be prepared by an amide forming reaction between an intermediate of formula XIX and cyanocyclopropyl carboxylic acid XX as illustrated in the following reaction scheme. The conditions for this reaction are as described above, e.g. in the transformation of II into I-a.

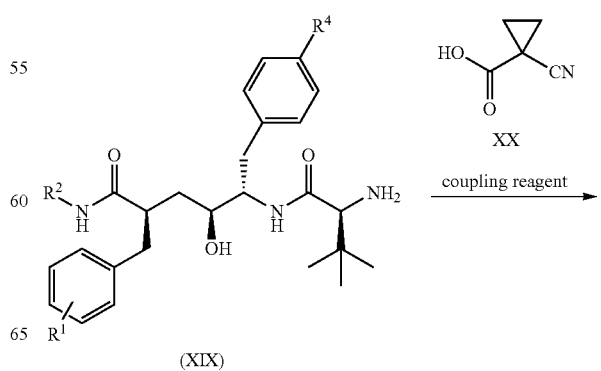
(XIX)

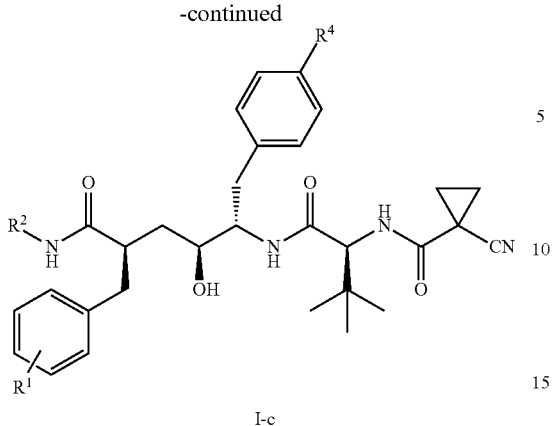

I-c

The intermediates of formula XIX can be prepared as outlined in the following scheme:

described above in the transformation of II to I-a, yielding an intermediate XXII. The Boc protecting group in XXII can be removed under art-known conditions, as described hereinbefore to obtain the free amino intermediate XIX.

The compounds of formula I wherein $R^3$ is a group of formula:

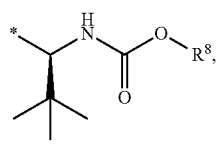

said compounds being represented by formula I-d, can be prepared by an urethane forming reaction at the end of the synthesis as illustrated in the following reaction scheme, by condensation of an intermediate of formula XIX with an appropriate electrophilic carbonyl compound such as a chlo-

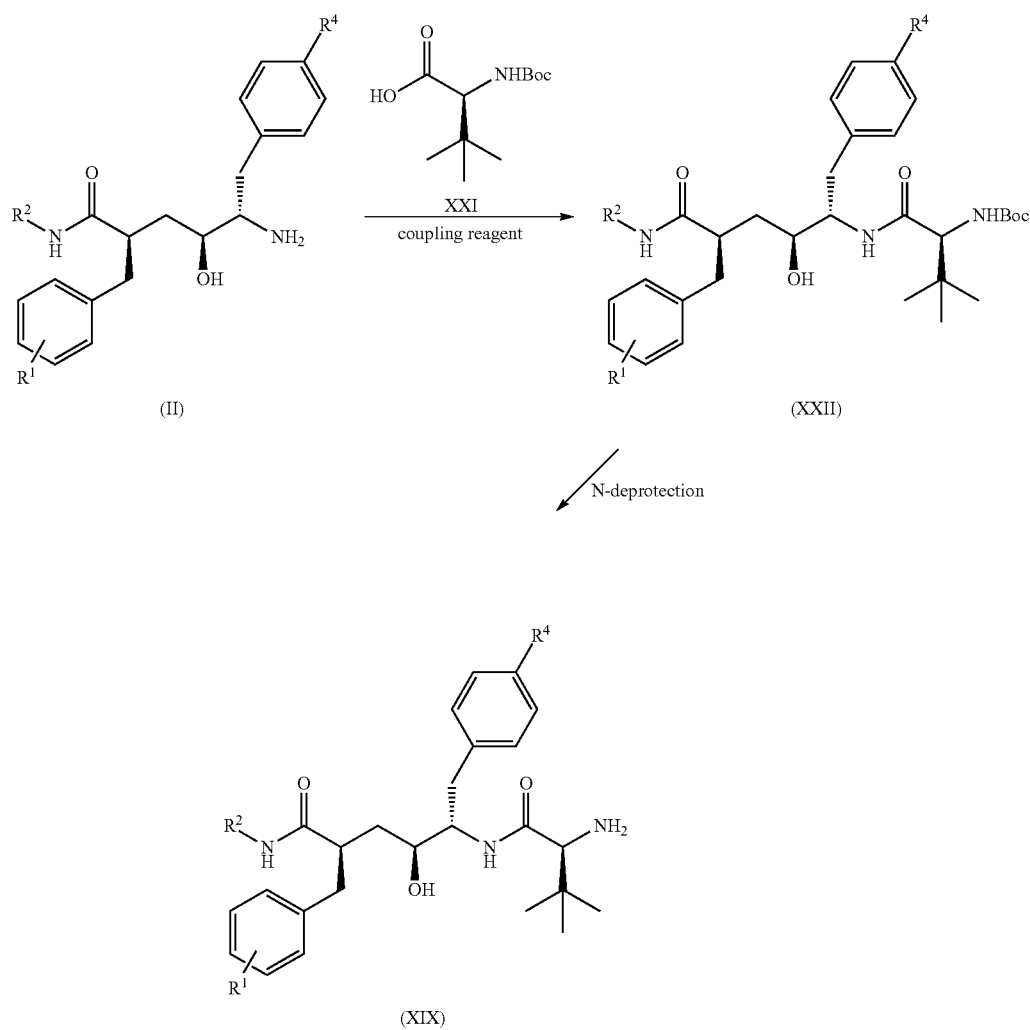

In a first step, an intermediate II is coupled with N-protected t.butylglycine XXI, such as Boc-t.butylglycine, in an amide-forming reaction, following reaction conditions as described roformate, or an activated succinimidyl, para-nitrophenyl, or pyridyl carbonate. This reaction is particularly suited for preparing compounds wherein $R^8$ is $C_{1-4}$alkoxy$C_{1-4}$alkyl.

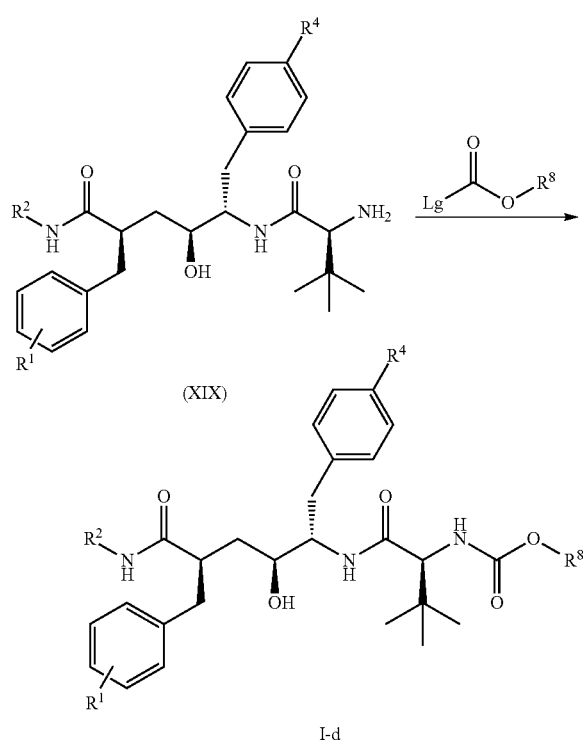

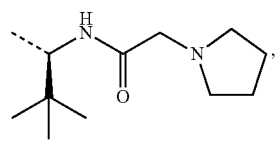

The compounds of formula I wherein R³ is a group of formula:

said compounds being represented by formula I-e, can be prepared either by a coupling reaction with pyrrolidinyl acetic acid in an amide-forming reaction, following reaction conditions as described above. As illustrated in the reaction scheme below, the compounds I-e can also be prepared by a two-step procedure involving first the reaction of an intermediate XIX with chloroacetyl chloride in the presence of a base, e.g. a tertiary amine such as triethylamine, in a solvent such as dichloromethane, resulting in intermediates XXIII. This reaction can e.g. be conducted iniatially at lower temperature such as at 0 C, followed by stirring at room temperature. The intermediates XXIII are then reacted with pyrrolidine in the presence of a nucleophilic catalyst such as tetrabutylammonium iodide or the like, preferentially in a bipolar aprotic solvent (e.g. DMA, DMF, N-methylpyrrolidinone). This reaction preferably is conducted at room temperature.

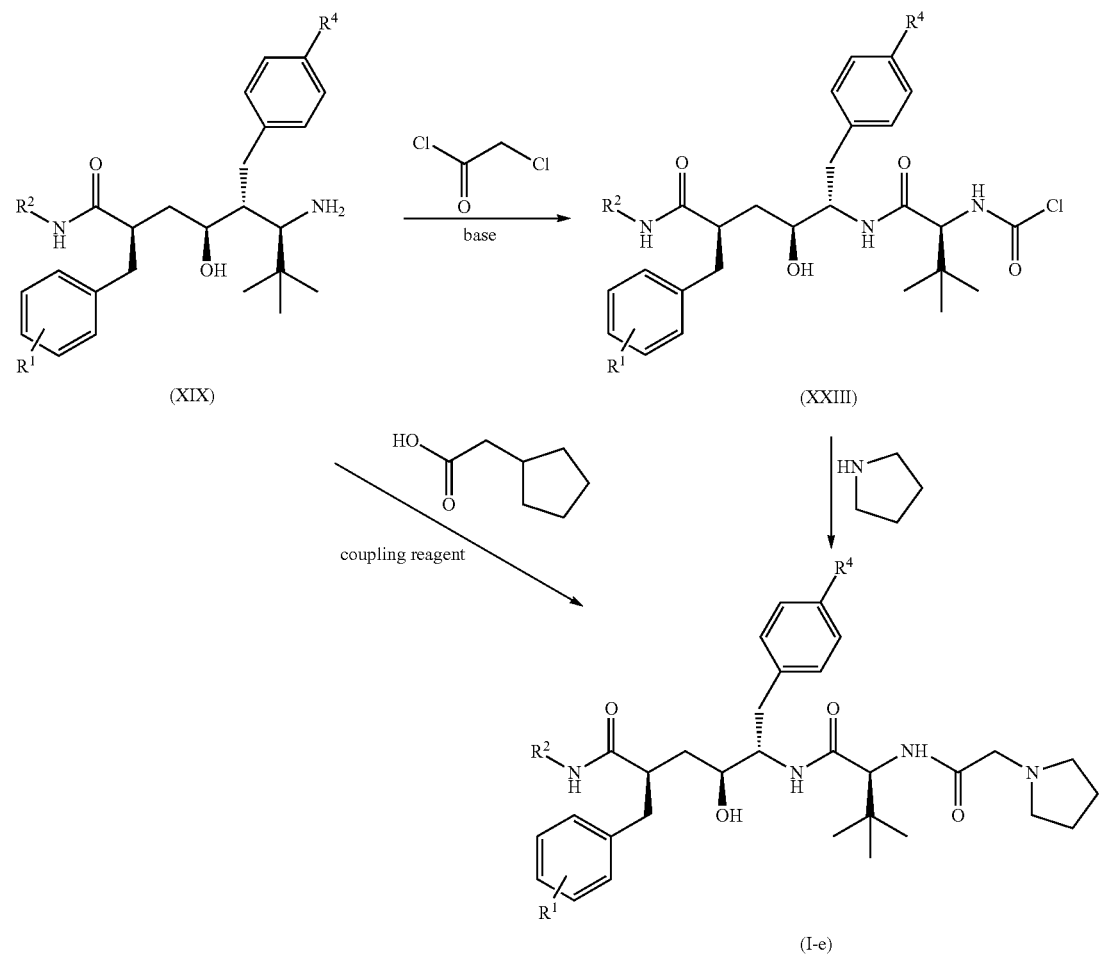

The compounds of formula I wherein R² is 3-hydroxychromanyl can also be prepared by first coupling a 3-hydroxy-4-chromanamine XXIV with a 3-arylpropionic acid XXV resulting in an intermediate XXVI, using conditions as described hereinbefore for the formation of an amide bond. Subsequently the NH and OH functions are protected with 2-methoxypropene resulting in intermediates XXVII. This transformation can be effected using a halogenated solvent, such as dichloromethane, in the presence of an acid catalyst, such as pyridinium p-toluenesulfonate, between 0° C. and room temperature. The resulting amides XXVII and oxirane XXVIII are treated with a strong base, such as n-butyl lithium, at a temperature range between −78° C. and −25° C. to afford intermediate XXIX. The latter is subjected to a cross-coupling reaction with a boronate or tin derivative XXX, as described hereinbefore, yielding XXXI, which in turn is deprotected to XXXII under acid conditions. The latter corresponds to an intermediate of formula II, and can be further processed as described above to compounds of formula:

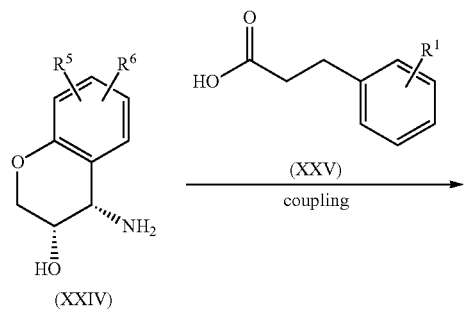

(XXIV)

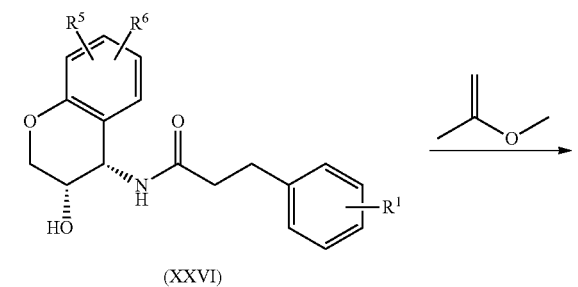

(XXVI)

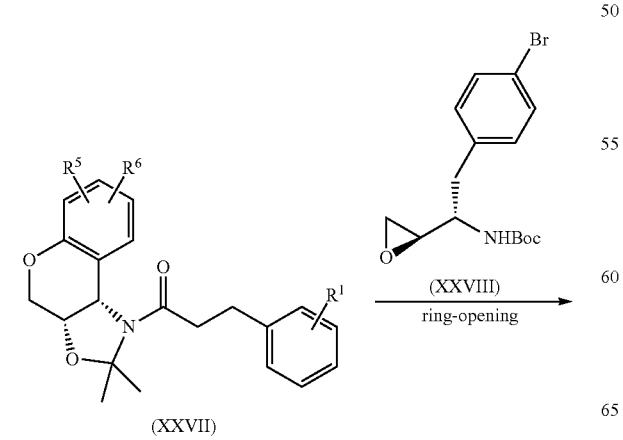

(XXVII)

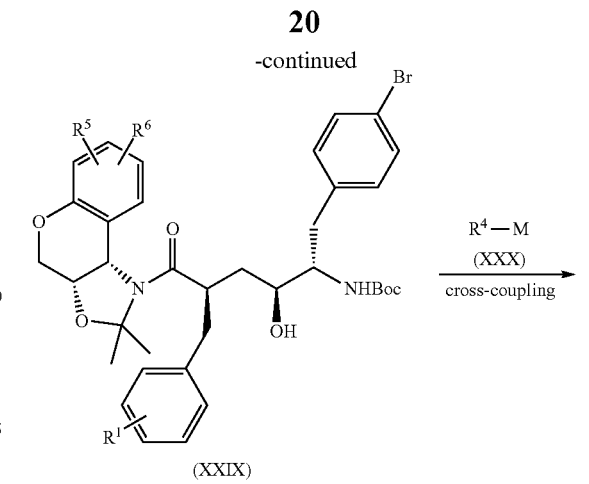

(XXIX)

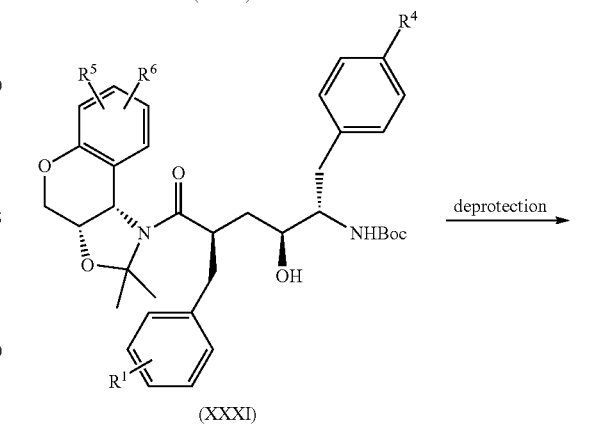

(XXXI)

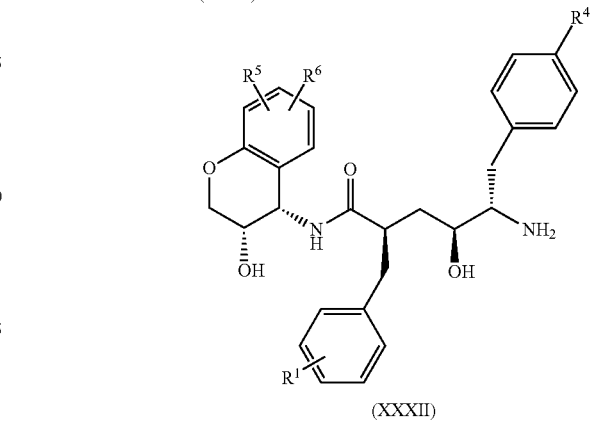

(XXXII)

The compounds of formula I can also be converted into each other by functional group transformation reactions. Compounds of formula I wherein R² is

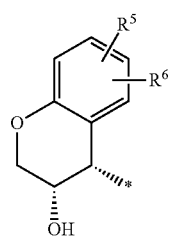

wherein one or both of R⁵ and R⁶ is chloro, bromo, or iodo can be converted to the corresponding compounds wherein one or both of R⁵ and R⁶ is hydrogen using hydrogen in the presence of a catalyst, such as palladium on carbon. Vice versa, where one or both of R⁵ and R⁶ is hydrogen, these compounds can be halogenated at the 6- or 8-position using an halogenating agent such as N-bromosuccinimide (NBS) or N-chlorosuccinimide (NCS). These conversion can also be performed on intermediates having the above R² group.

Some of the intermediates and starting materials are known compounds and may be commercially available or may be prepared according to art-known procedures.

The intermediates of formula R²—NH₂ wherein R² is a chromanol group can be prepared from a phenol XXXIII in 5 synthetic steps. In a first step phenol XXXIII is treated with 3-bromopropionic acid, in water in the presence of a base such as NaOH, at elevated temperature, such as reflux temperature. In a second step, the resulting 3-phenoxypropionic acid XXXIV undergoes a Friedel Crafts acylation, using oxalyl chloride and AlCl₃ in a solvent such as dichloromethane to afford the chromanone XXXV, which in turn is brominated (with bromine or CuBr₂) in a halogenated solvent, such as dichloro methane to afford the bromo chromanone XXXVI. Reduction with a metal hydride reagent, such as NaBH₄ in a protic solvent, such as methanol between 0° C. and room temperature affords the bromo alcohol XXXVII. The bromo alcohol XXXVII undergoes a Ritter reaction, using acetonitrile and an aqueous solution of a strong acid, such as sulfuric acid, to afford the intermediate oxazoline XXXVIII, that is hydrolyzed in diluted acid at a temperature between 80° C. and 120° C. to afford the racemic 4-amino chromanol of the formula XXXIX. Said 4-amino chromanol can be separated in the corresponding enantiomers using art known conditions, such as chromatography using a chiral stationary phase, or by diastereomeric salt formation using an optically pure organic acid as the resolving agent, such as mandelic acid, or the like.

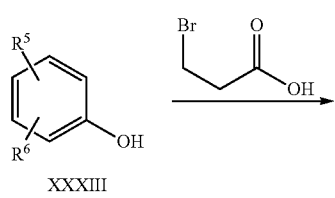

XXXIII

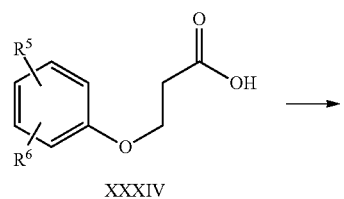

XXXIV

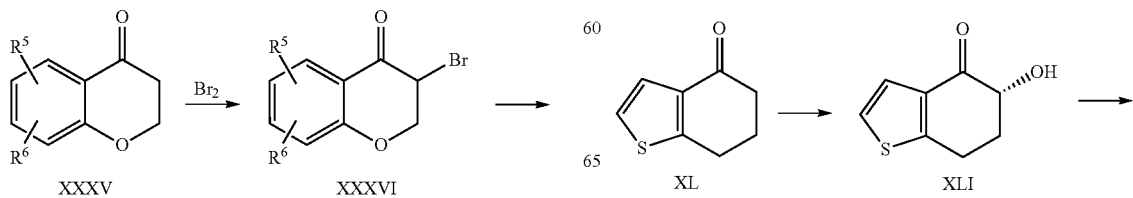

XXXV        XXXVI

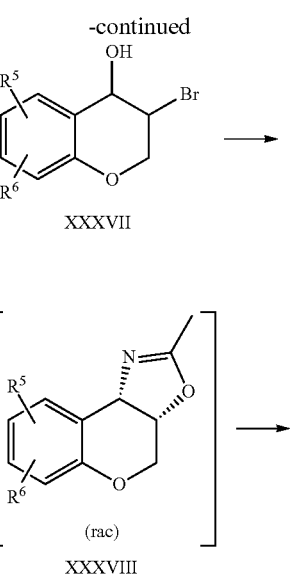

XXXVII

XXXVIII

XXXIX

4-Amino-chromanol XXXIX can be halogenated at the 6- or 8-position, e.g. with N-chlorosuccinimide, to afford the corresponding 6- or 8-halo substituted 4-aminochromanols.

The intermediates of formula R²—NH₂ which are

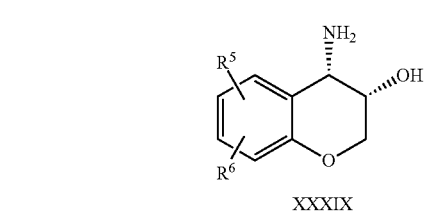

can be prepared from 6,7-dihydro-5H-benzo[b]thiophen-4-one by introducing a hydroxyl-group with (+)-(8,8-dichlorocamphorylsulfonyl)oxaziridine in the presence of a base such as sodium bis(trimethylsilyl)amide in a polar solvent, such as THF, at low temperature, such as −78° C. The keto group is then converted to the corresponding benzyloxime XLII using O-benzylhydroxylamine in pyridine, and the oxime is reduced to the corresponding amine XLIII using e.g. borane in a polar solvent, such as THF, in a temperature range between 0° C. and 70° C.

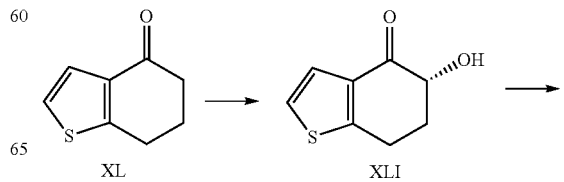

XL        XLI

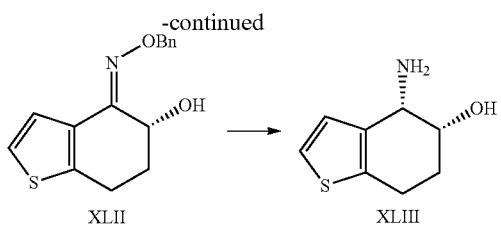

Cyclohexanol amine of the formula XLIVIII can be prepared in 4 steps from 3-(R)-methyl cyclohexanone. In a first step, the acetate XLVa is obtained by treatment in isopropenyl acetate at 100° C. in the presence of an acid catalyst, such as p-toluene sulfonic acid. The corresponding nitro ketone XLVI is obtained by reaction in a mixture of acetic anhydride and concentrated nitric acid at a temperature between room temperature and 50° C. The keto function is reduced by a metal hydride reagent, such as sodium borohydride, in an alcoholic solvent, such as methanol at room temperature, to afford the nitro alcohol XLVII. Reduction to the amino alcohol XLVIII is achieved by hydrogenolysis in the presence of Raney nickel in ethyl acetate.

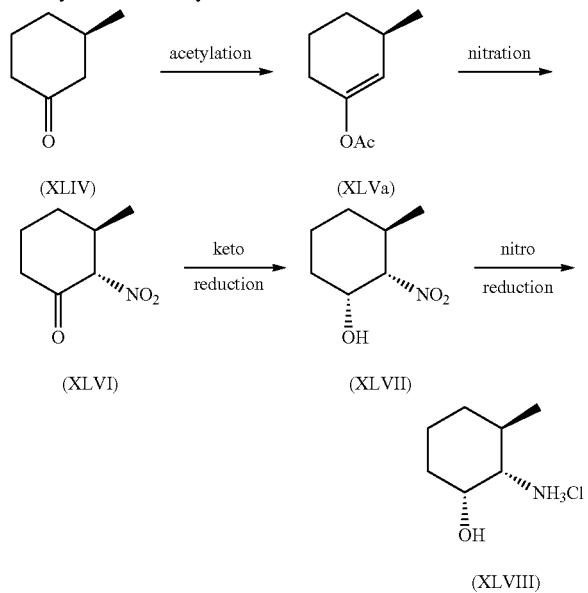

The compounds of formula I and most of the intermediates in the present invention contain an asymmetric carbon atoms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur with retention of stereochemical integrity. An alternative manner of separating the enantiomeric forms of the compounds of formula I and intermediates involves liquid chromatography, in particular liquid chromatography using a chiral stationary phase, such as high performance liquid chromatography or chromatography using supercritical carbon dioxide.

The compounds of formula I show anti-HIV properties, in particular they behave as HIV protease inhibitors. HIV is the aetiological agent of Acquired Immune Deficiency Syndrome (AIDS) in humans and preferentially infects human T-4 cells and destroys them or changes their normal function, particularly the coordination of the immune system. As a result, an infected patient has an ever-decreasing number of T-4 cells, which moreover behave abnormally. Hence, the immunological defense system is unable to combat infections and neoplasms and the HIV infected subject usually dies by opportunistic infections such as pneumonia, or by cancers.

The compounds of the invention also show activity against drug- and multidrug-resistant HIV strains, in particular against HIV strains that have acquired resistance to one or more of the approved protease inhibitors, in particular to atazanavir, lopinavir, and ritonavir.

Due to their anti-HIV properties, the compounds of formula I, the pharmaceutically acceptable addition salts and solvates thereof, including any stereoisomeric forms thereof, are useful in the treatment of individuals infected by HIV and for the prophylaxis of these infections. Conditions that may be prevented or treated with the compounds of the present invention, especially conditions associated with HIV, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention may therefore be used as a medicine against any of the above-mentioned conditions. In particular, the compounds of formula I may be used in the manufacture of a medicament for the treatment or the prevention of HIV infection.

In a further aspect this invention provides a method of treating a human, suffering from, or a method of preventing humans to suffer from viral infections, especially HIV infections. Said method comprises the administration, of an effective amount of a compound of formula I, a pharmaceutically acceptable addition salt, a pharmaceutically acceptable solvate thereof, or a possible stereoisomeric form thereof, to humans. Said use as a medicine or method of treatment comprises the administration to HIV-infected subjects of an amount effective to combat the conditions associated with HIV and other pathogenic retroviruses, especially HIV-1.

The present invention also provides compositions for treating HIV infection comprising a therapeutically effective amount of a compound of formula I and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula I used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in separate preparations or in a single preparation, together with pharmaceutically acceptable carriers. Said other antiretroviral compounds may be any known antiretroviral compounds such as nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126,443), apricitabine (AVX 754, (−)-dOTC), fozalvudine tidoxil (FZT, HDP-990003), phosphazide, KP-1461, racivir (PSI-5004), MIV-210, and GS-9131; non-nucleoside reverse transcriptase inhibitors (NNRTIs) such as delavirdine (DLV), efavirenz (EFV), nevirapine (NVP), dapivirine (TMC120), etravirine (ETR, TMC125), rilpivirine (TMC278), IDX899, RDEA-806, UK-453601, RDEA-427, and UC-781; nucleotide reverse transcriptase inhibitors (NtRTIs), e.g. tenofovir and its pro-drug tenofovir disoproxil fumarate (TDF); protease inhibitors, e.g. ritonavir (RTV), saquinavir (SQV), lopinavir (ABT-378, LPV), indinavir (IDV), amprenavir (VX-478), nelfinavir (AG-1343), atazanavir (BMS 232,632), darunavir (TMC114), fosamprenavir (GW433908 or VX-175), brecanavir (GW-640385, VX-385), tipranavir (PNU-140690), DG-17, SPI256, PPL-100 (MK 8122), and TMC310911; entry inhibitors, which comprise fusion inhibitors (e.g. enfuvirtide (T-20) sifuvirtide, HRG-214, albuvirtide, SUC-HAS, and maC46/M87o), attachment inhibitors, modulators of intracellular cholesterol and corticosteroid biosynthesis (e.g. SP-01A), and co-receptor inhibitors, the latter comprise the CCRS antagonists (e.g. CCR5 mAb004, maraviroc (UK-427,857), PRO-140, TAK-220, TAK-652, PF232798, vicriviroc (SCH-D, SCH-417, 690), GSK-706769, nifeviroc, and SCH-532706) and CXR4 antagonists (e.g. AMD-070), further examples of entry inhibitors are TNX-355, INCB 9471, BMS-488043, nonakine, and VGV-1; maturation inhibitors, e.g. bevirimat (PA-457) and vivecon; and inhibitors of the viral integrase, e.g. raltegravir (MK-0518), elvitegravir (JTK-303, GS-9137), BMS-538158, S-349572, JTK-656 S-247303, and GS-265744.

The following examples are intended to illustrate the present invention and not to limit its scope thereto.

EXAMPLES

Analytical thin-layer chromatography (TLC) was performed on silica gel 60 $F_{254}$ plates (Merck) with visualization by ultraviolet, potassium permanganate or phosphomolybdic acid. Silicagel column chromatography was performed on SuperFlash® (50 μm) or GraceResolv® (35-45 μm) silicagel cartridges. $^1$H Nuclear magnetic resonance (NMR) spectra were recorded at 400 or 500 MHz. Chemical shifts δ are given in ppm referenced to tetramethylsilane (TMS) and J values in Hz. Multiplicy is indicated using the following abbreviations: s for singlet, br. s for broad singlet, d for doublet, t for triplet, q for quartet, spt for septet and m for multiplet. Optical rotations $[\alpha]^{20}_D$ are reported in deg/dm and the concentration c is given in g/100 mL in the specified solvent. Infrared (IR) and vibrational circular dichroism (VCD) spectra were recorded in a 0.09 mm cell with $CaF_2$ windows, on a Bruker Equinox-55® instrument with a PMA-37 module at 4-$cm^{-1}$ resolution (samples were dissolved in DMSO-$d_6$). VCD's were collected three times with one hour collection time each. Unless otherwise indicated, enantiomeric excess (ee) was determined by supercritical fluid chromatography (SFC) on a Chiralpak Daicel® AD-H column. Compound names were generated using ChemDraw Ultra®, version 9.0 (CambridgeSoft®).

Example 1

Synthesis of tert-butyl (S)-2-(4-bromophenyl)-1-((S)-5-oxotetrahydrofuran-2-yl)ethyl-carbamate ((−)-Precursor 1)

Method A:

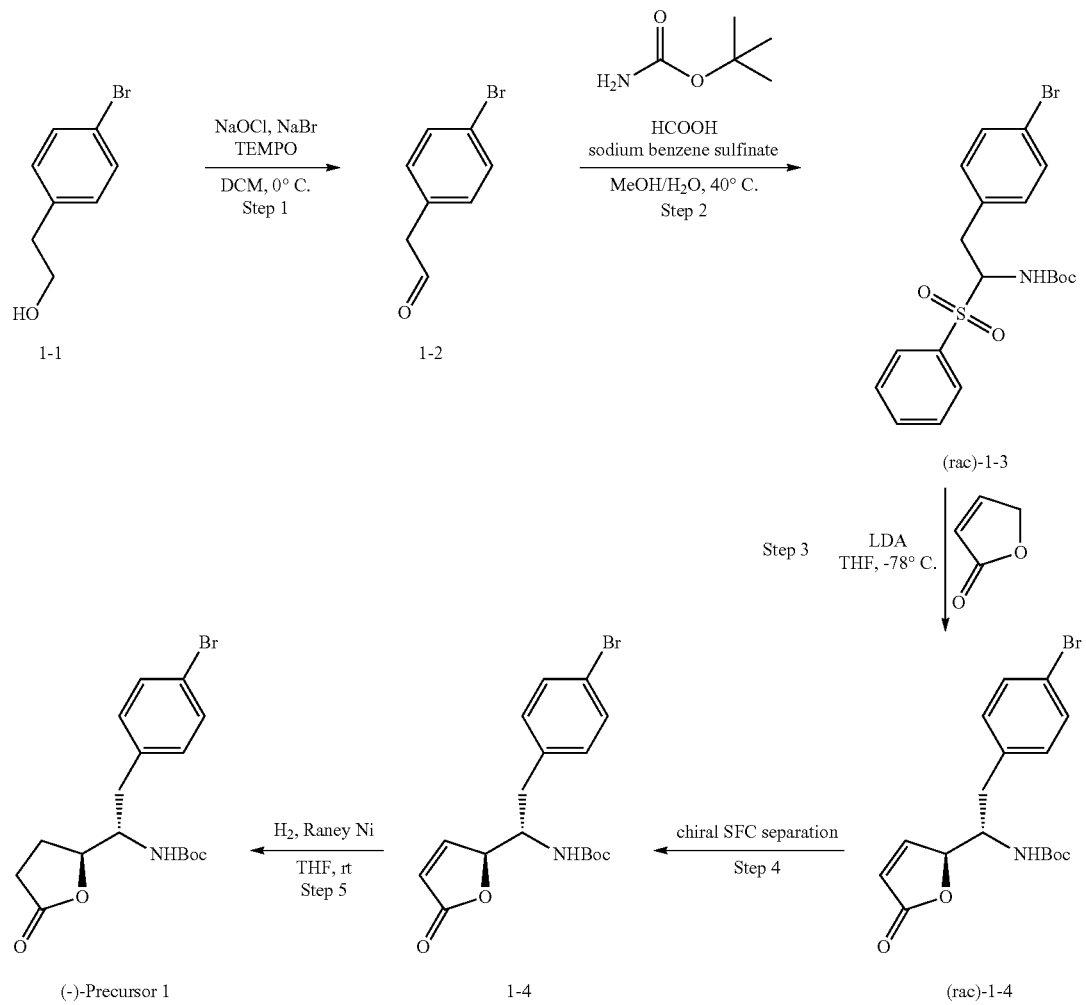

Step 1: 2,2,6,6-Tetramethylpiperidine-1-oxyl (TEMPO; 1.6 g, 1.0 mmol, 0.002 eq.) and NaBr (6 g, 500 mmol, 1.0 eq.) were successively added under vigorous stirring to a solution of alcohol 1-1 ([CAS No.: 4654-39-1]; 100 g, 500 mmol, 1.0 eq.) in dichloromethane (2300 mL) at 0° C. A solution of aqueous saturated NaHCO$_3$ and 10% NaOCl (400 mL) were added. The mixture was stirred for approximately ten minutes until thin-layer chromatography (TLC) indicated that the starting material had disappeared. The dichloromethane layer was separated. The aqueous layer was rapidly extracted with diethyl ether. The combined organic phases were washed with an aqueous solution of NaHSO$_3$ (10%) and KI (4%), brine, and dried with anhydrous sodium sulfate. After removing most of the volatiles under vacuum (keep temperature below 25° C.), the resulting solution of aldehyde 1-2 in dichloromethane (50 mL) was used as such directly in the next step.

Step 2: A mixture of the dichloromethane solution of aldehyde 1-2 (460 mmol, 1.0 eq.), tert-butyl carbamate (107.8 g, 920 mmol, 2.0 eq.), sodium benzene sulfinate (151.0 g, 920 mmol, 2.0 eq.) and formic acid (42.3 g, 920 mmol, 2.0 eq.) in a mixture of methanol (250 mL) and water (500 mL) was stirred at 40° C. for 24 hours (reaction was monitored by TLC). The reaction mixture was cooled to room temperature. The resulting precipitate was filtered off, washed with water and diethyl ether, and dried under reduced pressure to afford 150 g (72% starting from Intermediate 1-1) of Intermediate (rac)-1-3.

Step 3: To a mixture of diisopropylamine (26 g, 250 mmol, 1.1 eq.) in dry tetrahydrofuran (THF; 100 mL) was added dropwise n-butyllithium (100 mL of 2.5 M solution, 250 mmol, 1.1 eq.) at −78° C. under nitrogen. The mixture was allowed to warm to room temperature and stirred at room temperature for 30 minutes. The mixture was re-cooled to −78° C. and a solution of 2(5H)-furanone (21 g, 250 mmol, 1.1 eq.) in dry THF (100 mL) was added dropwise. After stirring for another 20 minutes at −78° C., the reaction mixture was transferred to a solution of Intermediate (rac)-1-3 (100 g, 227 mmol, 1.0 eq.) in dry THF (800 mL) at −78° C.

The resulting mixture was stirred for another 20 minutes at −78° C. A saturated aqueous NaHCO$_3$ solution was added dropwise to the reaction mixture at −40° C., extraction was done with ethyl acetate. The combined organic phases were washed with a saturated aqueous Na$_2$CO$_3$ solution and brine, dried with MgSO$_4$ and concentrated under vacuum. The resulting residue was washed with a diethyl ether/methanol (10:1) mixture and dried to afford 40 g of (rac)-1-4. The mother liquid was evaporated to dryness, the resulting residue was purified by preparative high-performance liquid chromatography (HPLC) to afford 10 g of (rac)-1-4. In total, 50 g (58%) of the racemic product was obtained.

Step 4: The racemic mixture (rac)-1-4 was separated via preparative supercritical fluid chromatography (SFC) on a Chiralpak Daicel® AD-20 μm column (50×300 mm, mobile phase: isocratic 30% propan-2-ol, flow rate: 130 mL/min) The desired (1S,2S)-enantiomer 1-4 was isolated as the second fraction with a yield of 42%.

Step 5: A solution of Intermediate 1-4 (10 g, 26.2 mmol, 1.0 eq.) in THF (200 mL) was hydrogenated (1.0 atm of hydrogen) at 25° C. for three hours with Raney Ni (2 g, 20% mass ratio) as catalyst. After uptake of hydrogen (1.0 eq.), the catalyst was filtered off and the filtrate was evaporated. The residue was purified by silica gel column chromatography to give 7.0 g (70%, ee>95%) of (−)-Precursor 1 as white crystals. $^1$H NMR (400 MHz, CDCl$_3$) 5 ppm 1.39 (s, 9H) 2.05-2.23 (m, 2H) 2.45-2.61 (m, 2H) 2.85 (dd, J=13.5, 8.6 Hz, 1H) 2.91 (dd, J=13.7, 7.4 Hz, 1H) 3.98 (q, J=8.5 Hz, 1H) 4.46 (t, J=7.6 Hz, 1H) 4.62 (d, J=9.8 Hz, 1H) 7.12 (d, J=7.8 Hz, 2H) 7.43 (d, J=8.0 Hz, 2H); [α]$^{20}_D$=−23.4° (c 0.99, CH$_3$CN).
Method B:

solution of amide 1-5 ([CAS No.: 949885-93-2]; 103.7 g, 267 mmol, 1.0 eq.) in THF (560 mL) was dropwise added to the reaction mixture over a period of at least one hour, the temperature was kept below 3° C. The reaction mixture was allowed to warm to room temperature and stirred for a minimum of four hours at this temperature. After cooling to −5° C., the reaction was quenched by the slow addition of an aqueous ammonium chloride solution. The organic layer was separated, washed with brine and partially concentrated under reduced pressure. Heptane was added, the mixture was again partially concentrated under reduced pressure and cooled to 15° C. The precipitate was filtered off and washed with heptane. After drying at 45° C. for 16 hours, 112.2 g (wt % 72%, 80% yield) of crude Intermediate 1-6 was obtained.

Step 2: A solution of RuCl$_3$.3H$_2$O (2.04 g, 7 mmol, 0.03 eq.) in water (77 mL) was added to a solution of NaIO$_4$ (236 g, 1105 mmol, 5.5 eq.) in water (1.9 L). This reaction mixture was added over 30 minutes to a solution of Intermediate 1-6 (107.7 g (wt % 71%), 201 mmol, 1.0 eq.) in acetone (1.9 L) at room temperature. The reaction mixture was stirred at room temperature until conversion was complete (approximately one hour). An aqueous Na$_2$S$_2$O$_3$ solution was added to the reaction mixture over 30 minutes. The reaction mixture was concentrated under reduced pressure until no more acetone came out. Water (1.9 L) was added to the residue, the suspension was stirred for 30 minutes at room temperature. The precipitate was filtered off and the wet cake was re-slurried in water. The wet cake obtained after filtration and washing with water was dried at 45° C. to give 80.6 g (wt % 90%, 90% yield) of crude Intermediate 1-7.

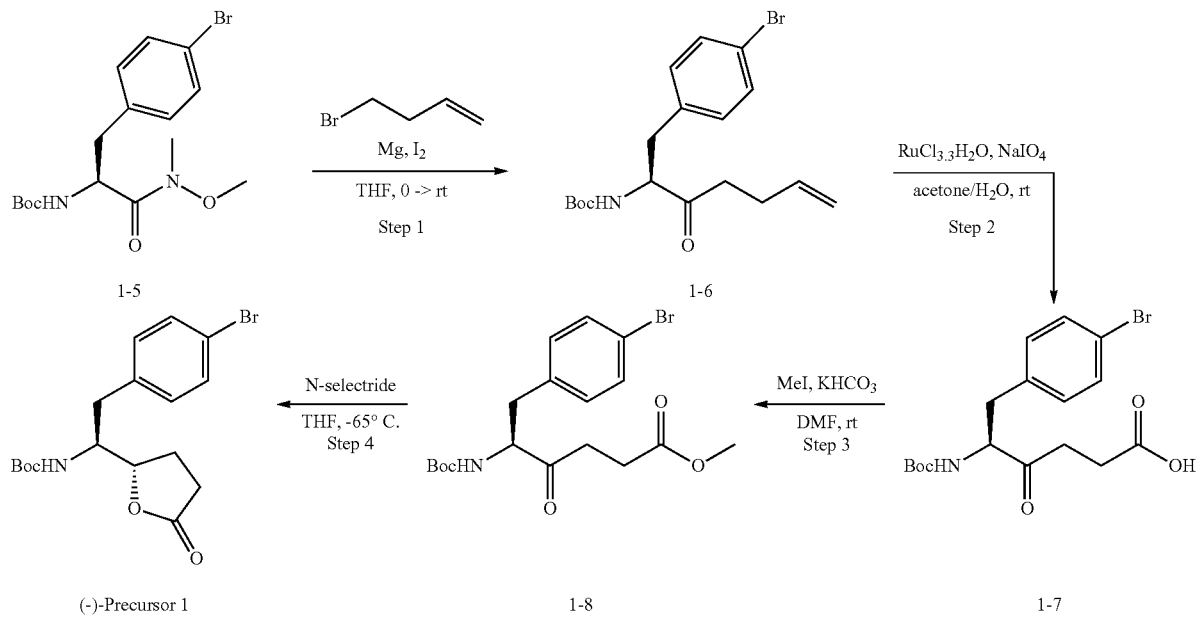

Step 3: A mixture of Intermediate 1-7 (67.0 g (wt % 90%), 150 mmol, 1.0 eq.) and KHCO$_3$ (75.1 g, 750 mmol, 5.0 eq.) in dimethylformamide (DMF; 1200 mL) was stirred at room temperature for 20 minutes. Iodomethane (42.6 g, 300 mmol, 2.0 eq.) was added over a period of 20 minutes to the reaction mixture, the reaction mixture was stirred at room temperature for seven hours. After the reaction mixture was filtered over Celite, an aqueous solution of ammonium chloride was added at such a rate that the temperature stayed below 25° C. Next Step 1: Iodine (2.2 g, 8.0 mmol, 0.03 eq.) was added to a reaction flask charged with magnesium (79.8 g, 3282 mmol, 12.3 eq.) and THF (2.7 L) under nitrogen. The reaction mixture was heated to 30-35° C. and maintained at this temperature. 4-Bromo-butene (361.4 g, 2677 mmol, 10.0 eq.) was slowly added over a period of two hours, the temperature of the reaction was kept below 65° C. After the addition was complete, the reaction mixture was stirred for a minimum of two hours at 60-65° C. and then cooled in an ice bath. A tert-butyl methyl ether was added and the mixture was filtered over Celite. The organic layer was separated, washed with brine and concentrated under reduced pressure. Heptane was added to the residue, after the suspension was stirred for six hours at room temperature, the precipitate was filtered off, washed with heptane and dried in a vacuum oven at 40° C. for 16 hours. 50.0 g (wt % 91%, 73% yield) of Intermediate 1-8 was obtained.

Step 4: N-Selectride (135 mL of a 1M solution in THF, 135 mmol, 1.24 eq.) was dropwise added over a minimum of 1.5 hours to a solution of ester 1-8 (45 g, 109 mmol, 1.0 eq.) in dry THF (900 mL) at −65° C. under nitrogen. After the reaction mixture was stirred for an extra hour at −65° C., the temperature was raised to −35° C. and stirring was continued for 30 minutes at this temperature. Subsequently an aqueous 10% citric acid solution was dropwise added at 0 to 10° C., followed by the addition of tert-butyl methyl ether. After the mixture was stirred for 30 minutes, the organic layer was separated, washed with a saturated aqueous NaHCO₃ solution and brine, and concentrated under reduced pressure. The residue was re-dissolved in tert-butyl methyl ether and concentrated again under reduced pressure. The crude product was purified by flash silica gel column chromatography (eluent: heptane/tert-butyl methyl ether 2:1) to give 37.0 g (94%, ee>95%) of (−)-Precursor 1 as an off-white solid. $[\alpha]^{20}_D = -20.9°$ (c 1.0, MeOH)

The primary amines mentioned below were used as Precursors representing examples of formula $R^2$—$NH_2$ as defined hereinbefore. Those for which no commercial supply is available can be synthesized according to literature procedures (Precursors 2, 14a, 15 and 17) or through procedures described in Examples 2-13 (Precursors 3-14b).

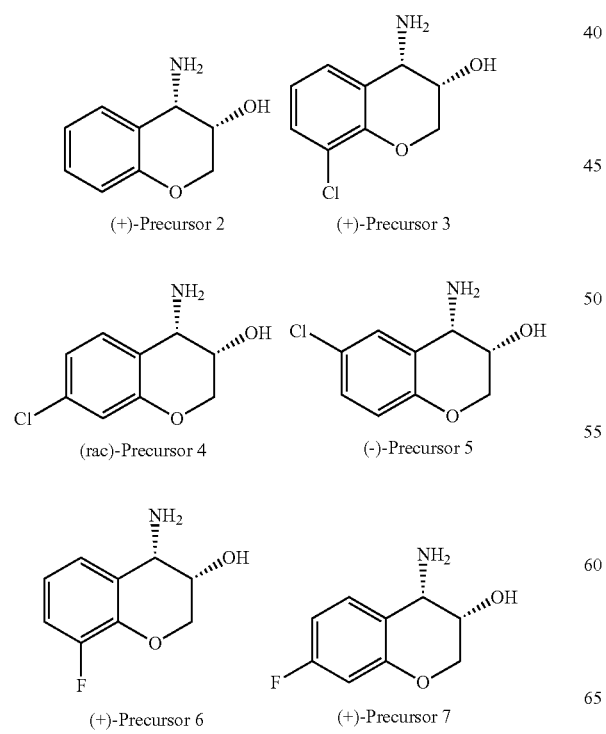
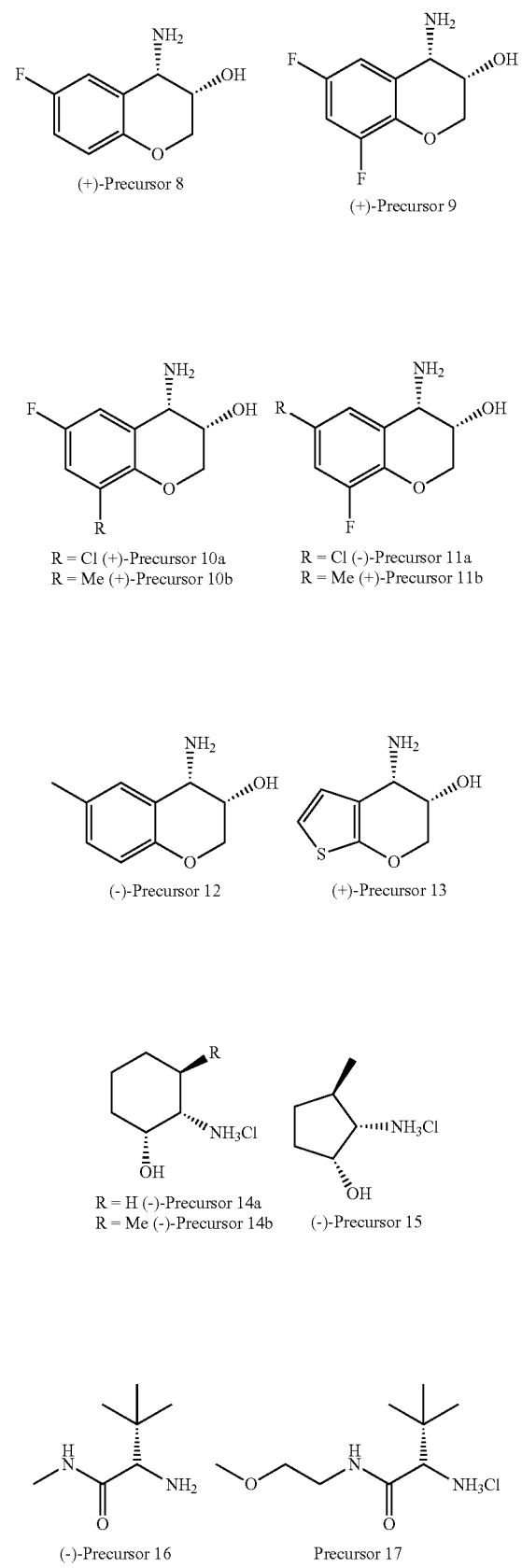

Example 2

(3S,4S)-4-amino-8-chlorochroman-3-ol ((+)-Precursor 3)

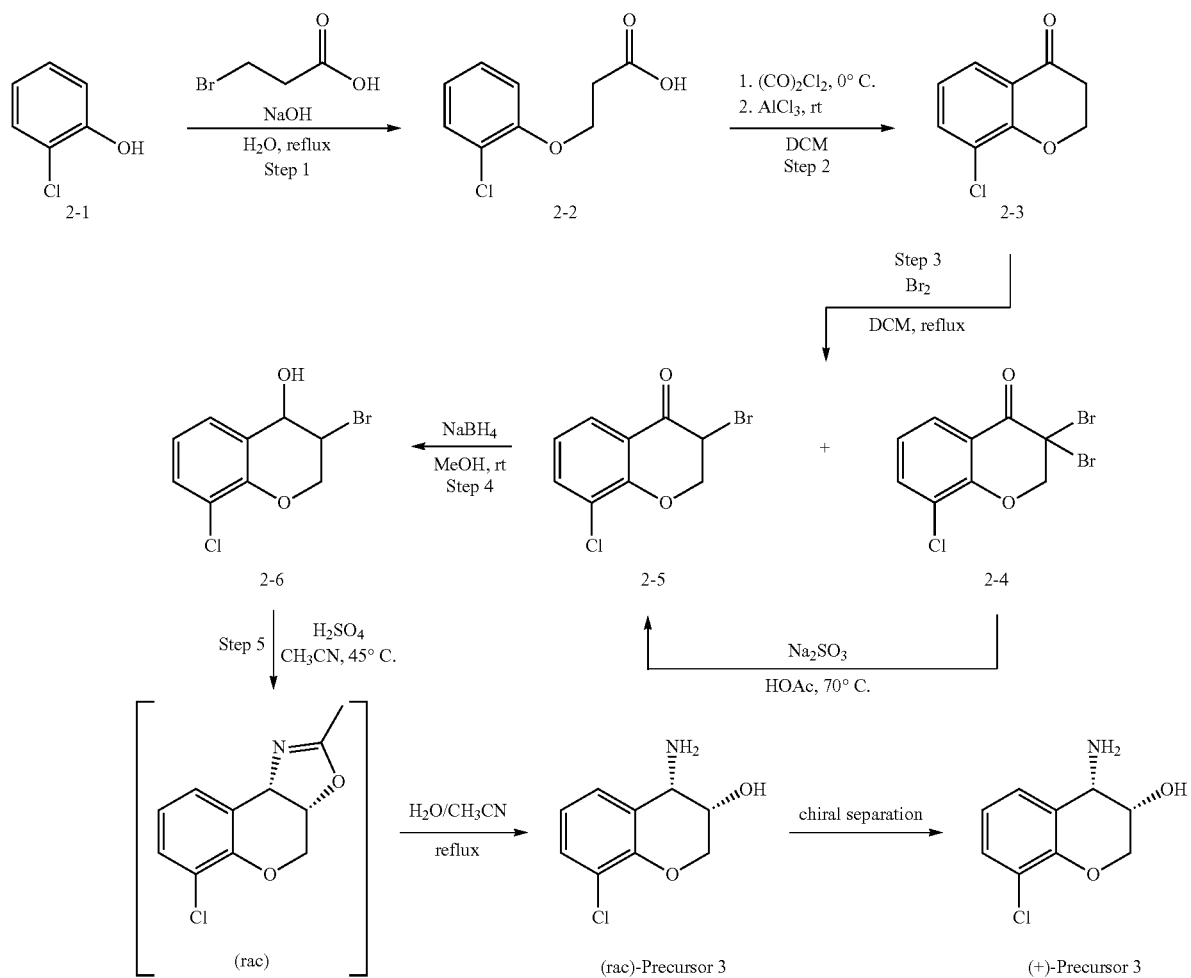

Step 1: An ice-cooled solution of 3-bromopropionic acid (298 g, 1.95 mol, 1.25 eq.) and NaOH (156 g of an aqueous 50% solution, 1.95 mol, 1.25 eq.) in water (500 mL) was added over a period of 90 minutes to a mixture of 2-chlorophenol ([CAS No.: 95-57-8]; 200 g, 1.56 mol, 1.0 eq.) and NaOH (124 g of an aqueous 50% solution, 1.56 mol, 1.0 eq.) in water (1 L) at reflux temperature. The reaction mixture was stirred at reflux temperature for three hours. After cooling down to room temperature, the reaction mixture was acidified with a concentrated aqueous hydrochloric acid solution. The precipitate was filtered off and washed with water to give a first crop of acid 2-2. The filtrate was extracted with dichloromethane, the combined organic phases were subsequently extracted with saturated NaHCO$_3$. The aqueous layer was acidified with a concentrated aqueous hydrochloric acid solution; the precipitate was filtered off and washed with water to give a second crop of acid 2-2. After drying in a vacuum oven over weekend, 112 g (36%) of Intermediate 2-2 was obtained as a white solid.

Step 2: A solution of acid 2-2 (112 g, 558 mmol, 1.0 eq.) and some drops of DMF in dichloromethane (1.5 L) was cooled in an ice bath. Oxalylchloride (142 g, 1.12 mol, 2.0 eq.) was added dropwise, the reaction mixture was allowed to warm to room temperature and stirred overnight. The solvent was concentrated under reduced pressure. The residue was reconstituted in dichloromethane (1.5 L). Aluminium trichloride (89 g, 670 mmol, 1.2 eq.) was added portion wise and the reaction mixture was stirred overnight at room temperature. The reaction mixture was slowly poured into a cooled 1 M hydrochloric acid solution. The layers were separated and the water phase was extracted with dichloromethane. The combined organic layers were washed with a saturated aqueous Na$_2$CO$_3$ solution and brine, dried with anhydrous MgSO$_4$ and concentrated under reduced pressure, to obtain 104 g (102%) of crude Intermediate 2-3.

Step 3: Bromine (30.7 mL, 598 mmol, 1.05 eq.) was slowly added to a solution of crude Intermediate 2-3 (104 g) in dichloromethane at reflux temperature. After the addition was complete, the resulting mixture was stirred at reflux temperature for 30 minutes. The reaction mixture was cooled to room temperature, washed with a saturated aqueous sodium metabisulfite solution and brine, dried with anhydrous MgSO$_4$, and concentrated under vacuum to give a mixture of dibromine 2-4 and monobromine 2-5. The residue was dissolved in acetic acid (750 mL), and sodium sulfite (93 g, 740 mmol) was added. The reaction mixture was stirred at 70° C. for three hours. The reaction mixture was cooled to room temperature and partially evaporated, water and dichloromethane were added. The organic layer was separated and concentrated under reduced pressure. Crude Intermediate 2-5 was used as such in the next step (no yield was determined).

Step 4: NaBH$_4$ (21.7 g, 574 mmol) was added in portions to a solution of crude Intermediate 2-5 in methanol (1.5 L) at 0° C. and the mixture was stirred at room temperature for 30 minutes. The reaction mixture was partially concentrated under reduced pressure, and the residue was diluted with ethyl acetate. The organic phase was washed with brine, dried with anhydrous magnesium sulphate and concentrated under reduced pressure. The crude product was purified by silica gel column chromatography (eluent: dichloromethane→dichloromethane/methanol 96:4) to provide 105.5 g (67% starting from Intermediate 2-3) of Intermediate 2-6.

Step 5: Concentrated sulfuric acid (16 mL, 300 mmol, 2.0 eq.) was dropwise added to a solution of Intermediate 2-6 (39.5 g, 150 mmol, 1.0 eq.) in acetonitrile (800 mL). The reaction was stirred at 45-50° C. until no more starting material was present (about five hours) and then concentrated under reduced pressure. Water (800 mL) and acetonitrile (200 mL) were added, the reaction mixture was stirred at reflux temperature for two days. The reaction mixture was then cooled to room temperature, washed with dichloromethane and basified with an aqueous 50% NaOH solution to pH~12-13. The precipitate was filtered off, washed with water and dried in a vacuum oven to give 25.2 g (84%) of racemic Precursor 3.

The racemic mixture was separated via preparative HPLC on a Chiralpak Daicel® AD column (mobile phase: acetonitrile), the desired (3S,4S)-enantiomer ((+)-Precursor 3) was isolated as the first fraction (ee>95%). $^1$H NMR (400 MHz, DMSO-d$_6$) δ ppm 1.92 (br. s., 2H) 3.84-3.92 (m, 2H) 4.14 (dd, J=10.9, 2.5 Hz, 1H) 4.17 (dd, J=11.1, 5.5 Hz, 1H) 5.17 (br. s., 1H) 6.85 (t, J=7.8 Hz, 1H) 7.23 (d, J=7.6 Hz, 1H) 7.41 (d, J=7.8 Hz, 1H); [α]$^{20}_D$=+59.2° (c 0.37, MeOH). The absolute configuration of (+)-Precursor 3 was established by comparison of the optical rotation ([α]$^{20}_D$=+45.8° (c 0.27, MeOH)) after reductive removal of the chlorine (hydrogen gas (1 atm), palladium on carbon as catalyst) with that of (+)-Precursor 2.

Example 3

Synthesis of (rac)-cis-4-amino-7-chlorochroman-3-ol ((rac)-Precursor 4)

(rac)-Precursor 4 was prepared starting from 3-chlorophenol using the procedures as exemplified for the preparation of (rac)-Precursor 3. $^1$H NMR (400 MHz, DMSO-d$_6$) δ ppm 1.83 (br. s., 2H) 3.79-3.89 (m, 2H) 4.03-4.12 (m, 2H) 5.12 (br. s., 1H) 6.76 (d, J=2.0 Hz, 1H) 6.90 (dd, J=8.2, 2.0 Hz, 1H) 7.44 (d, J=8.4 Hz, 1H)

Example 4

Synthesis of (3S,4S)-4-amino-6-chlorochroman-3-ol ((−)-Precursor 5)

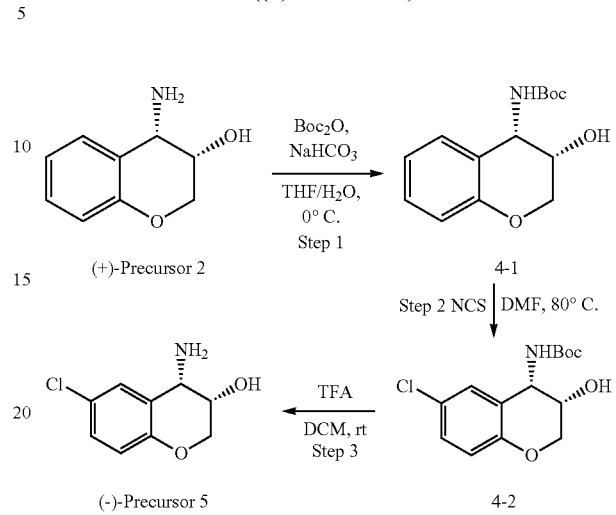

Step 1: Di-tert-butyl dicarbonate (14.5 g, 66.6 mmol, 1.1 eq.) was dissolved in THF (100 mL), the solution was cooled to 0° C. and stirred. (3S,4S)-4-Amino-chroman-3-ol ((+)-Precursor 2) (10 g, 60.5 mmol, 1.0 eq.) and NaHCO$_3$ (5.1 g, 60.5 mmol, 1.0 eq.) were added simultaneously while maintaining good stirring. The reaction mixture was stirred at room temperature for four hours. The solvent was partially evaporated, water was added and the resulting mixture was extracted with diethylether. The combined organic extracts were washed with a 10% citric acid solution and brine, dried with MgSO$_4$, filtered and evaporated to dryness to give 21 g of crude carbamate 4-1.

Step 2: The crude carbamate 4-1 was dissolved in DMF (100 mL) and N-chlorosuccinimide (NCS; 8.9 g, 66.6 mmol, 1.1 eq.) was added. The reaction mixture was stirred at 80° C. for one hour. The reaction mixture was cooled to room temperature, diluted with diethylether, washed with a saturated aqueous Na$_2$CO$_3$ solution and brine, dried with anhydrous MgSO$_4$ and concentrated under reduced pressure to give 16.3 g (82% over two steps) of crude Intermediate 4-2.

Step 3: A solution of 4-2 (16.3 g, 54.2 mmol, 1.0 eq.) and trifluoroacetic acid (TFA; 124 g, 1084 mmol, 20.0 eq.) in dichloromethane (100 mL) was stirred at room temperature for one hour. The reaction mixture was basified with a saturated Na$_2$CO$_3$ solution and extracted with dichloromethane. The combined organic phases were washed with water and brine, and dried with MgSO$_4$. The crude product was recrystallized form ethyl acetate to give 6.8 g (61%) of (−)-Precursor 5 (ee>95%). $^1$H NMR (400 MHz, DMSO-d$_6$) δ ppm 1.88 (br. s., 2H) 3.79-3.90 (m, 2H) 4.05 (dd, J=11.5, 2.5 Hz, 1H) 4.08 (dd, J=11.0, 4.8 Hz, 1H) 5.12 (br. s., 1H) 6.71 (d, J=8.5 Hz, 1H) 7.10 (dd, J=8.7, 2.6 Hz, 1H) 7.47 (d, J=2.3 Hz, 1H); [α]$^{20}_D$=−20.7° (c 0.36, MeOH).

Example 5

Synthesis of (3S,4S)-4-amino-8-fluorochroman-3-ol (H-Precursor 6)

(rac)-cis-4-amino-8-fluorochroman-3-ol was prepared starting from commercially available 8-fluorochroman-4-one [CAS No.: 11141-00-5] using the procedures as exemplified for the preparation of (rac)-Precursor 3. The racemic mixture was separated via preparative SFC on a Chiralpak Daicel® AD-H column (30×250 mm, mobile phase: isocratic 32% methanol (containing 0.2% isopropylamine)/68% $CO_2$, flow rate: 50 mL/min), the desired (3S,4S)-enantiomer ((+)-Precursor 6) was isolated as the first fraction (ee>95%). $^1$H NMR (400 MHz, DMSO-$d_6$) δ ppm 1.90 (br. s., 2H) 3.84-3.92 (m, 2H) 4.09 (dd, J=11.1, 2.7 Hz, 1H) 4.14 (dd, J=10.9, 5.5 Hz, 1H) 5.15 (br. s., 1H) 6.82 (td, J=7.9, 5.1 Hz, 1H) 7.01 (ddd, J=11.3, 8.2, 1.4 Hz, 1H) 7.24 (d, J=7.8 Hz, 1H); $[α]20_D$=+24.6° (c 0.43, MeOH). The absolute stereochemical configuration was determined using VCD.

Example 6

Synthesis of (3S,4S)-4-amino-7-fluorochroman-3-ol ((+)-Precursor 7)

(rac)-cis-4-Amino-7-fluorochroman-3-ol was prepared using the procedures as exemplified for the preparation of (rac)-Precursor 3. A mixture of (rac)-cis-4-amino-7-fluorochroman-3-ol (31.8 g, 174 mmol, 1.0 eq.) and (+)-(S)-mandelic acid (26.4 g, 174 mmol, 1.0 eq.) was refluxed in methanol (600 mL) until a clear solution was obtained. The mandelic acid salt, obtained after crystallization overnight, was collected by filtration and dissolved in a 3 M aqueous NaOH solution. The water layer was extracted with ethyl acetate, the combined organic phases were dried with anhydrous $MgSO_4$ and concentrated under reduced pressure to give 6.5 g (21%) of enantiomerically enriched (+)-Precursor 7 (ee>95%). $^1$H NMR (400 MHz, DMSO-$d_6$) δ ppm 2.03 (br. s., 2H) 3.81-3.86 (m, 2H) 4.01-4.10 (m, 2H) 5.09 (br. s., 1H) 6.53 (dd, J=10.6, 2.6 Hz, 1H) 6.68 (td, J=8.5, 2.6 Hz, 1H) 7.43 (dd, J=8.4, 7.2 Hz, 1H); $[α]^{20}_D$=+36.0° (c 0.42, MeOH). The absolute stereochemical configuration was determined using VCD.

Example 7

Synthesis of (3S,4S)-4-amino-6-fluorochroman-3-ol (H-Precursor 8)

(rac)-cis-4-Amino-6-fluorochroman-3-ol was prepared starting from the commercially available 6-fluorochroman-4-one [CAS No.: 66892-34-0] using the procedures as exemplified for the preparation of (rac)-Precursor 3. (rac)-cis-4-amino-6-fluorochroman-3-ol (7.63 g, 41.7 mmol, 1.0 eq.) was dissolved in ethanol (30 mL) while heating, (−)-(R)-mandelic acid (6.68 g, 45.8 mmol, 1.1 eq.) was added portion wise and the solution was heated to reflux temperature. Then, heptane (6 mL) was added dropwise. The formed suspension was allowed to cool to room temperature and was left to stand for 1 hour. Filtration gave the mandelic acid salt as a white solid which was recrystallized from ethanol. The obtained salt was dissolved in an aqueous 2 M NaOH solution. The water phase was extracted with ethyl acetate, the combined organic phases were dried with anhydrous $MgSO_4$ and concentrated under reduced pressure to give 2.0 g (26%) of enantiomerically enriched (+)-Precursor 8 (ee=82%). $^1$H NMR (400 MHz, DMSO-$d_6$) δ ppm 1.88 (br. s., 2H) 3.79-3.89 (m, 2H) 4.01 (ddd, J=11.1, 2.6, 1.0 Hz, 1H) 4.06 (dd, J=11.1, 5.1 Hz, 1H) 5.08 (d, J=3.5 Hz, 1H) 6.69 (dd, J=9.0, 4.9 Hz, 1H) 6.90 (td, J=8.6, 3.3 Hz, 1H) 7.24 (dd, J=9.7, 3.2 Hz, 1H); $[α]^{20}_D$=+25.8° (c 0.50, MeOH). The absolute stereochemical configuration was determined using VCD.

Example 8

Synthesis of (3S,4S)-4-amino-6,8-difluorochroman-3-ol ((+)-Precursor 9)

(rac)-cis-4-Amino-6,8-difluorochroman-3-ol was prepared starting from 2,4-difluorophenol [CAS No.: 367-27-1] using the procedures as exemplified for the preparation of (rac)-Precursor 3. The racemic mixture was separated via preparative SFC on a Chiralpak Daicel® AD-H column (30×250 mm, mobile phase: isocratic 50% methanol (containing 0.2% isopropylamine)/50% $CO_2$, flow rate: 50 mL/min), the desired (3S,4S)-enantiomer ((+)-Precursor 9) was isolated as the first fraction (ee>95%). $^1$H NMR (400 MHz, DMSO-$d_6$) δ ppm 1.92 (br. s., 2H) 3.84-3.90 (m, 2H) 4.11 (ddd, J=11.2, 2.2, 0.8 Hz, 1H) 4.16 (dd, J=11.1, 4.6 Hz, 1H) 5.19 (br. s., 1H) 7.06 (ddd, J=11.3, 8.5, 3.1 Hz, 1H) 7.14 (dm, J=9.7 Hz, 1H); $[α]^{20}_D$=+9.7° (c 0.41, MeOH). The absolute stereochemical configuration was determined using VCD.

Example 9a

Synthesis of (3S,4S)-4-amino-8-chloro-6-fluorochroman-3-ol ((+)-Precursor 10a)

(rac)-cis-4-Amino-8-chloro-6-fluorochroman-3-ol was prepared starting from 2-chloro-4-fluorophenol [CAS No.: 1996-41-4] using the procedures as exemplified for the preparation of (rac)-Precursor 3. The desired (3S,4S)-enantiomer ((+)-Precursor 10a) was isolated via preparative SFC on Chiralpak Daicel® AD-H column (30×250 mm, mobile phase: isocratic 40% methanol (containing 0.6% isopropylamine)/60% $CO_2$, flow rate: 50 mL/min), the desired (3S, 4S)-enantiomer ((+)-Precursor 10a) was isolated as the first fraction (ee>95%). $^1$H NMR (400 MHz, DMSO-$d_6$) δ ppm 2.03 (br. s., 2H) 3.84-3.91 (m, 2H) 4.15 (ddd, J=11.3, 2.5, 0.8 Hz, 1H) 4.20 (dd, J=11.3, 4.4 Hz, 1H) 5.21 (br. s., 1H) 7.20 (dd, J=8.2, 3.1 Hz, 1H) 7.30 (ddd, J=9.5, 3.1, 0.9 Hz, 1H); $[α]^{20}_D$=+39.7° (c 1.0, MeOH). The absolute stereochemical configuration was determined using VCD.

Example 9b

Synthesis of (3S,4S)-4-amino-6-fluoro-8-methyl-chroman-3-ol ((+)-Precursor 10b)

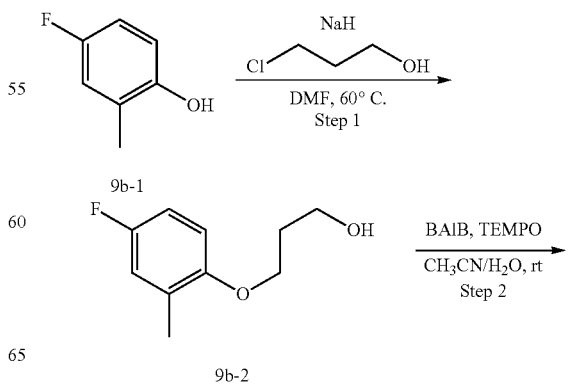

-continued

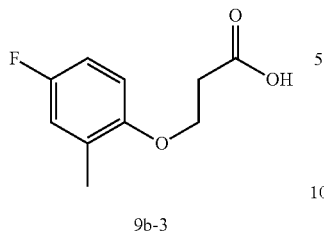

9b-3

(rac)-cis-4-amino-6-fluoro-8-methylchroman-3-ol was prepared starting from commercially available 2-methyl-4-fluorophenol [CAS No.: 452-72-2] (9b-1) using a slightly modified synthesis procedure as exemplified for the preparation of (rac)-Precursor 3.

Step 1: To a solution of NaH (9.1 g of a 60% dispersion in oil, 238 mmol, 1.2 eq.) in DMF (300 mL) at 0° C. was drop wise added a solution of 2-methyl-4-fluorophenol [CAS No.: 452-72-2]; 25.0 g, 198 mmol, 1.0 eq.) in DMF (40 mL). The suspension was stirred at room temperature for 30 minutes and cooled again to 0° C., a solution of 1-chloro-3-hydroxypropane (22.5 g, 238 mmol, 1.2 eq.) in DMF (40 mL) was added drop wise. The reaction was heated for two hours at 60° C. (an additional amount of NaH and 1-chloro-3-hydroxypropane may be needed to complete the reaction). The reaction mixture was cooled to room temperature and water was added, the water layer was extracted with diethyl ether, the combined organic phases were washed with an aqueous NaOH solution and brine, dried with anhydrous $MgSO_4$ and concentrated under reduced pressure. The crude product was used as such in the next step.

Step 2: Intermediate 9b-2 (12.9 g, 70 mmol) was dissolved in a 1:1 mixture of $CH_3CN/H_2O$ (425 mL). TEMPO (1094 mg, 7 mmol, 0.1 eq.) and bis(acetoxy)-iodobenzene (BAIB; 56.4 g, 175 mmol, 2.5 eq.) were added portion wise and the reaction mixture was stirred at room temperature overnight (additional TEMPO and BAIB may be required to complete the oxidation). The reaction was quenched by the addition of an aqueous $Na_2S_2O_3$ solution, the aqueous phase was extracted with DCM and the combined organic layers were subsequently extracted with an aqueous $Na_2CO_3$ solution. After acidification with a 1 M aqueous hydrochloric acid, the water phase was extracted with DCM. The combined organic layers were dried with anhydrous $MgSO_4$ and concentrated under reduced pressure to afford 13.2 g (96%) of Intermediate 9b-3. The latter was further converted to (rac)-cis-4-amino-6-fluoro-8-methylchroman-3-ol using the procedures as exemplified in Example 2. The desired (3S,4S)-enantiomer ((+)-Precursor 10b) was isolated as the first fraction via preparative HPLC on a Chiralpak Daicel® AD column (mobile phase: acetonitrile). $^1$H NMR (400 MHz, DMSO-$d_6$) δ ppm 1.89 (br. s., 2H) 2.08 (s, 3H) 3.83 (br. s., 2H) 4.04 (d, J=10.9 Hz, 1H) 4.09 (dd, J=11.5, 4.9 Hz, 1H) 5.07 (br. s., 1H) 6.82 (d, J=9.6 Hz, 1H) 7.07 (d, J=9.6 Hz, 1H); $[α]^{20}_D$=+50.3° (c 0.38, MeOH). The absolute stereochemical configuration was determined using VCD.

Example 10a

Synthesis of (3S,4S)-4-amino-6-chloro-8-fluorochroman-3-ol ((−)-Precursor 11a)

(rac)-cis-4-Amino-6-chloro-8-fluorochroman-3-ol was prepared starting from 4-chloro-2-fluorophenol [CAS No.: 348-62-9] using the procedures as exemplified for the preparation of (rac)-Precursor 3. The racemic mixture was separated via preparative SFC on Chiralpak Daicel® AD-H column (20×250 mm, mobile phase: isocratic 40% methanol (containing 0.2% isopropylamine)/60% $CO_2$, flow rate: 50 mL/min), the desired (3S,4S)-enantiomer ((−)-Precursor 11a) was isolated as the first fraction (ee>95%). $^1$H NMR (400 MHz, DMSO-$d_6$) δ ppm 1.93 (br. s., 2H) 3.88 (br. s., 2H) 4.11-4.16 (m, 1H) 4.18 (dd, J=11.3, 4.3 Hz, 1H) 5.22 (d, J=3.1 Hz, 1H) 7.22 (dd, J=10.7, 2.5 Hz, 1H) 7.35 (s, 1H); $[α]^{20}_D$=−32.0° (c 0.42, MeOH). The absolute stereochemical configuration was determined using VCD.

Example 10b

Synthesis of (3S,4S)-4-amino-8-fluoro-6-methylchroman-3-ol ((+)-Precursor 11b)

(rac)-cis-4-amino-8-fluoro-6-methylchroman-3-ol was prepared starting from 4 methyl-2-fluorophenol [CAS No.: 452-81-3] using the procedures as exemplified for the preparation of (rac)-Precursor 10b. The racemic mixture was separated via preparative SFC on Chiralpak Daicel® AD-H column (30×250 mm, mobile phase: isocratic 20% methanol (with 0.6% isopropylamine)/20% $CO_2$, flow rate: 50 mL/min), the desired (3S,4S)-enantiomer ((+)-Precursor 11b) was isolated as the first fraction (ee>95%). $^1$H NMR (400 MHz, DMSO-$d_6$) δ ppm 1.82 (br. s., 2H) 2.20 (s, 3H) 3.84 (br. s, 2H) 4.04-4.12 (m, 2H) 5.10 (br. s., 1H) 6.84 (dd, J=12.1, 2.0 Hz, 1H) 7.05 (br. s., 1H); $[α]^{20}_D$=+88.8° (c 0.18, MeOH). The absolute stereochemical configuration was determined using VCD.

Example 11

Synthesis of (3S,4S)-4-amino-6-methylchroman-3-ol ((−)-Precursor 12)

(rac)-cis-4-Amino-6-methylchroman-3-ol was prepared starting from 6-methyl-4-chromanone [CAS No.: 39513-75-2] using the procedures as exemplified for the preparation of (rac)-Precursor 3. The racemic mixture was separated via preparative SFC on Chiralpak Daicel® AD-H column (30×250 mm, mobile phase: isocratic 17% methanol (with 0.5% isopropylamine)/83% $CO_2$, flow rate: 50 mL/min), the desired (3S,4S)-enantiomer ((−)-Precursor 12) was isolated as the second fraction (ee>95%). $^1$H NMR (400 MHz, DMSO-$d_6$) δ ppm 1.78 (br. s., 2H) 2.20 (s, 3H) 3.77-3.84 (m, 2H) 3.94 (ddd, J=10.7, 2.4, 1.3 Hz, 1H) 3.96-4.03 (m, 1H) 5.00 (br. s., 1H) 6.58 (d, J=8.2 Hz, 1H) 6.88 (dd, J=8.2, 2.0 Hz, 1H) 7.19 (d, J=2.0 Hz, 1H); $[α]^{20}_D$=−18.7° (c 0.43, MeOH). The absolute stereochemical configuration was determined using VCD.

Example 12

Synthesis of (4S,5R)-4-amino-4,5,6,7-tetrahydrobenzo[b]thiophen-5-ol ((+)-Precursor 13)

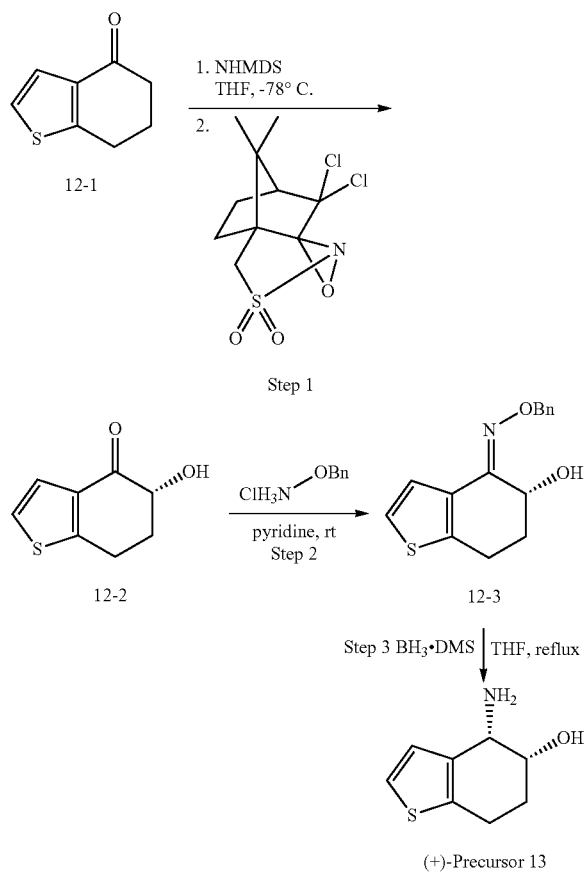

Step 1: A solution of 6,7-dihydro-5H-benzo[b]thiophen-4-one (starting material 12-1, [CAS No.: 13414-95-4]; 39 g, 256 mmol, 1.0 eq.) in THF (150 mL) was added dropwise to a mixture of sodium bis(trimethylsilyl)amide (NHMDS; 307 mL of a 1 M solution in THF, 307 mmol, 1.2 eq.) and THF (200 mL) at −78° C. under argon atmosphere, the reaction mixture was stirred for an additional 30 minutes at −78° C. A solution of (+)-(8,8-dichloro-camphorylsulfonyl)oxaziridine (94 g, 307 mmol, 1.2 eq.) in THF (300 mL) was added dropwise. After being stirred for two hours at −78° C., the reaction mixture was quenched by the addition of an excess of acetic acid and allowed to warm to room temperature. Water and ethyl acetate were added, and the water phase was separated and extracted with ethyl acetate. The combined organic phases were dried with anhydrous MgSO4 and concentrated under reduced pressure. The residue was re-dissolved in dichloromethane (300 mL) and triturated with heptane (500 mL), the precipitate was removed by filtration and washed with diisopropyl ether. The filtrate was concentrated under reduced pressure, the residue was purified by silica gel column chromatography (eluent: heptane heptane/ethyl acetate 4:6) to provide 50 g (116%) of impure Intermediate 12-2. The crude product was used as such in the next step.

Step 2: O-benzylhydroxylamine hydrochloride (41 g, 256 mmol, 1.0 eq.) was added to a solution of crude Intermediate 12-2 (50 g) in pyridine (500 mL). The reaction mixture was stirred at room temperature over weekend. The mixture was evaporated and co-evaporated two times with toluene. The residue was re-dissolved in ethyl acetate, the organic phase was washed with an aqueous 5% citric acid solution and brine, dried with anhydrous MgSO4 and concentrated under reduced pressure to give 72 g of crude Intermediate 12-3.

Step 3: Borane dimethyl sulfide complex (198 mL of a 1 M solution in THF 395 mmol, 1.54 eq.) was added dropwise to a solution of crude Intermediate 12-3 (72 g) in THF (1 L) at 0° C. The reaction mixture was stirred at reflux temperature overnight. After the solvent was partially removed by distillation (the reaction flask was equipped with a distillation condenser), the reaction was further stirred at reflux temperature until complete conversion. The reaction mixture was cooled in an ice bath and quenched by the cautious addition of water. The water phase was saturated with NaCl and several times extracted with methyltetrahydrofuran. The combined organic phases were dried with anhydrous MgSO4 and concentrated under reduced pressure to give an 8:2 cis/trans-isomeric mixture. The desired cis-isomer was isolated via silica gel column chromatography (eluent: dichloromethane dichloromethane/7 M ammonia in methanol 96:4), 17.8 g was obtained (40% over 3 steps, 60% ee (the ee was determined by liquid chromatography (LC) after amide formation with (+)-(S)-mandelic acid)). (+)-Precursor 13 (17.7 g, 105 mmol, 1.0 eq.) was recrystallized with (+)-(S)-mandelic acid (16 g, 105 mmol, 1.0 eq.) in methanol overnight. The white solid was filtered off. The filtrate was concentrated and the obtained residue was recrystallized again. Both batches were combined and dissolved in a 3 M aqueous NaOH solution. The water phase was extracted with dichloromethane, the combined organic layers were dried with anhydrous MgSO4 and concentrated under reduced pressure to give 11.5 g (65%) of enantiomerically pure (+)-Precursor 13 (ee>95%). $^1$H NMR (400 MHz, CHLOROFORM-d) δ ppm 1.78-2.03 (m, 2H) 2.20 (br. s., 3H) 2.76 (ddd, J=16.6, 9.4, 6.2 Hz, 1H) 2.93 (dd, J=16.6, 5.3 Hz, 1H) 3.80-4.00 (m, 2H) 6.94 (d, J=5.0 Hz, 1H) 7.13 (d, J=5.3 Hz, 1H); $[\alpha]^{20}_D$=+59.6° (c 0.49, MeOH). The absolute stereochemical configuration was determined using VCD.

Example 13

Synthesis of (1S,2R,6R)-2-hydroxy-6-methylcyclohexanamine hydrochloride ((−)-Precursor 14b)

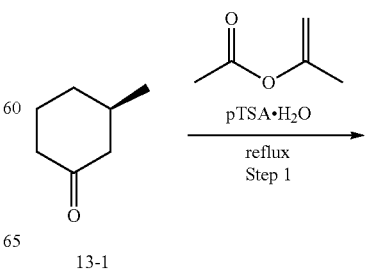

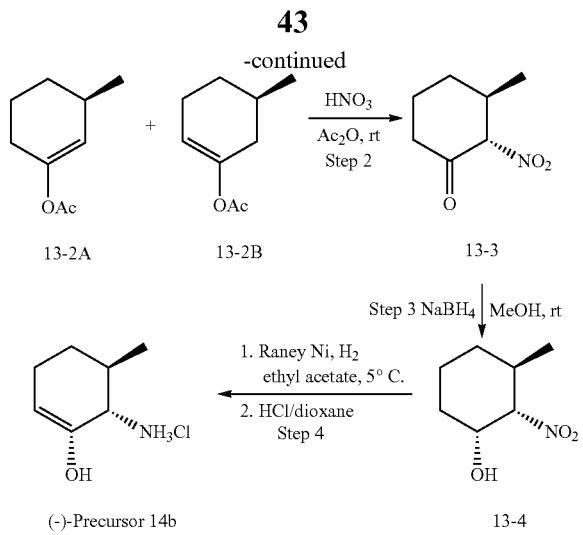

Step 1: Ketone 13-1 ([CAS No.: 13368-65-5]; 430 g, 3.83 mol, 1.0 eq.) and para-toluenesulfonic acid monohydrate (pTSA.H$_2$O; 72.9 g, 0.38 mol, 0.1 eq.) in isopropenyl acetate (2.5 L) were refluxed for 6 hours at 100° C. After the reaction mixture was cooled to room temperature, water was added. The organic layer was separated and washed with a saturated aqueous NaHCO$_3$ solution and brine, dried with anhydrous NaSO$_4$ and concentrated under vacuum to afford 530 g (90%) of a 7:10 mixture of the desired isomer 13-2A and the undesired isomer 13-2B (isomeric ratio was determined by $^1$H NMR). This mixture was used as such in the next step.

Step 2: The isomeric mixture 13-2A and 13-2B (106.2 g, 0.95 mol, 1.0 eq.) was dissolved in acetic acid anhydride (400 mL). Concentrated nitric acid (61 mL, 0.95 mol, 1.0 eq.) was added dropwise at such a rate that the reaction temperature was maintained between 30° C. and 40° C. After the addition was complete, the reaction was stirred at room temperature for two hours. TLC showed completion of the reaction (eluent: petroleum ether/ethyl acetate 5:1, R$_f$=0.4, two spots, closely). The reaction mixture was added dropwise to an aqueous saturated NaHCO$_3$ solution (79.8 g NaHCO$_3$ in water, 0.95 mol, 1.0 eq.). The mixture was extracted with ethyl acetate, the combined organic layers were washed with brine, dried with anhydrous Na$_2$SO$_4$ and concentrated under vacuum. The crude product was purified by silica gel column chromatography (eluent: petroleum ether/ethyl acetate 97:3→91:9) to afford 12.5 g (11%) of Intermediate 13-3 (the second spot).

Step 3: NaBH$_4$ (40 g, 1.03 mol, 1.3 eq.) was added in portions to a solution of Intermediate 13-3 (125 g, 795 mmol, 1.0 eq.) in dry methanol (3.0 L) at room temperature. The reaction mixture was stirred for 30 minutes at room temperature. The mixture was neutralized with an aqueous 10% KHSO$_4$ solution to pH~7 and concentrated under reduced pressure. Water was added and the mixture was extracted with ethyl acetate. The combined organic phases were washed with brine, dried with anhydrous MgSO$_4$ and concentrated under reduced pressure to give a 1:1 mixture of Intermediate 13-4 and its epimeric alcohol. Both epimers were separated via preparative SFC on a Chiralpak Daicel® AD-5 µm column (30×250 mm, mobile phase: isocratic 20% isopropanol/80% CO$_2$, flow rate 60 mL/min), 29 g (22%) of the desired isomer 13-4 was obtained as the first fraction. $^1$H NMR (400 MHz, CDCl$_3$) δ ppm 0.99 (d, J=6.8 Hz, 3H), 1.10 (m, 1H), 1.50 (m, 2H), 1.75-1.91 (m, 2H), 2.01 (m, 1H), 2.50 (m, 1H), 2.85 (br. s, 1H), 4.20 (dd, J=11.6, 2.0 Hz, 1H), 4.51 (s, 1H).

Step 4: A solution of 13-4 (29 g, 169.6 mmol, 1.0 eq.) in ethyl acetate (1.25 L) was hydrogenated at atmospheric pressure for five hours at 5° C. with Raney Ni (32 g) as catalyst. After uptake of hydrogen gas (3.0 eq.), the catalyst was filtered off. A hydrochloric acid solution in dioxane was added to the filtrate at 0° C., the resulting mixture was stirred for 30 minutes. The solvent was partially removed under reduced pressure, the precipitate was collected by filtration and washed with petroleum ether and diethyl ether to give 20.9 g (74%) of (−)-Precursor 14b (ee>95%, the ee was determined by LC after amide formation with (S)-(+)-α-methoxy-α-trifluoromethyl-phenylacetylchloride). $^1$H NMR (400 MHz, MeOD) δ ppm 1.01 (d, J=6.5 Hz, 3H) 1.04-1.19 (m, 1H) 1.42-1.60 (m, 2H) 1.70-1.81 (m, 1H) 1.81-2.01 (m, 1H) 1.81-2.01 (m, 1H) 2.79 (dd, J=10.8, 3.0 Hz, 1H) 4.02-4.06 (m, 1H); [α]$^{20}$$_D$=−0.53° (c 1.01, MeOH).

Mentioned below are the carboxylic acid and carbonate Precursors required as building blocks leading to the introduction of R$^3$ as defined hereinbefore. Those for which no commercial supply is available, can be synthesized according to literature procedures (Precursor 23 and 24) or through the procedure described in Example 14 (Precursor 22).

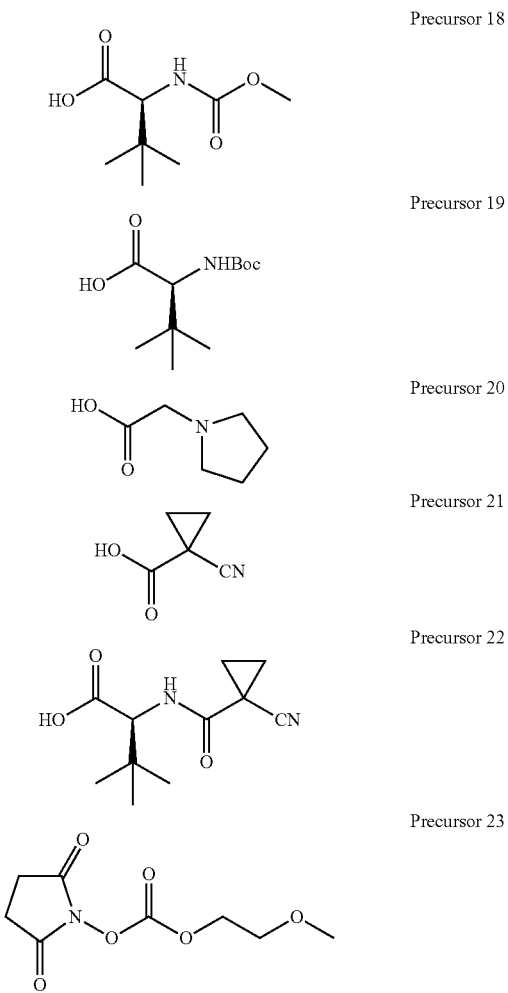

-continued

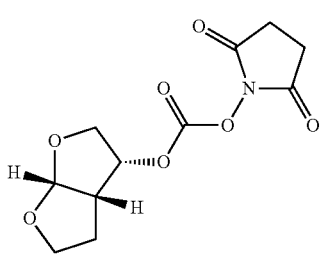

Precursor 24

Example 14

Synthesis of (S)-2-(1-cyanocyclopropanecarboxamido)-3,3-dimethylbutanoic acid (Precursor 22)

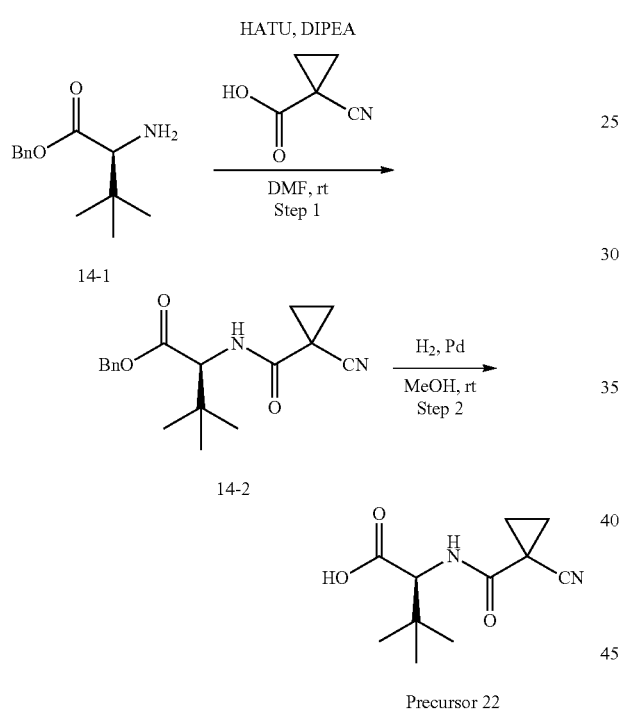

Amine 14-1 was synthesized according to literature procedures starting from Precursor 19.

Step 1: HATU (3.56 g, 9.35 mmol, 1.15 eq.) was added to a solution of amine 14-1 (1.8 g, 8.13 mmol, 1.0 eq.), 1-cyanocyclopropanecarboxylic acid (0.90 g, 8.13 mmol, 1.0 eq.) and N-ethyl-N-isopropylpropan-2-amine (DIPEA; 3.15 g, 8.13 mmol, 1.0 eq.) in DMF (80 mL) at −20° C. The reaction mixture was stirred at room temperature for one hour. Ethyl acetate was added, the organic phase was washed with a saturated NaHCO₃ solution, dried with anhydrous MgSO₄ and concentrated under reduced pressure to give 1.83 g (72%) of crude Intermediate 14-2. This was used as such in the next step.

Step 2: A solution of Intermediate 14-2 (1.83 g, 5.81 mmol, 1.0 eq.) in methanol was hydrogenated at atmospheric pressure at 25° C. for 3 hours with Pd (Pd/C 10%) as catalyst. The reaction mixture was filtered over Celite and the filtrate concentrated under reduced pressure. The residue was purified by silica gel column chromatography (eluent: dichloromethane/methanol/acetic acid 97:2:1) to give 0.75 g (58%) of Precursor 22. (It was observed that during the execution of the above mentioned synthesis sequence, extensive racemization had taken place!) $^1$H NMR (400 MHz, CHLOROFORM-d) δ ppm 1.07 (s, 9H) 1.56 (d, J=3.7 Hz, 2H) 1.63-1.79 (m, 2H) 4.41 (d, J=9.0 Hz, 1H) 6.87 (d, J=8.8 Hz, 1H) 11.12 (br. s., 1H)

Mentioned below are Precursors representing examples of formula $R^4$-M as defined hereinbefore which were used for Suzuki or Stille cross-coupling reactions. Those for which no commercial supply is available, can be synthesized according to literature procedures (Precursor 25 and 26) or by procedures described in Examples 15 and 16 (Precursors 27, 28, 36 and 37).

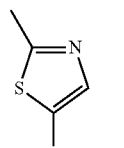

Precursor 25

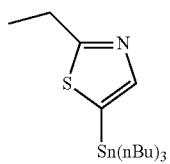

Precursor 26

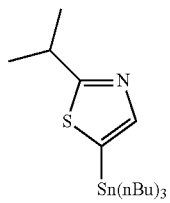

Precursor 27

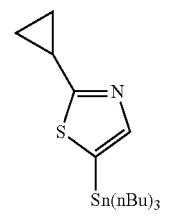

Precursor 28

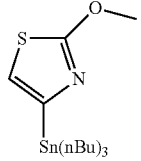

Precursor 29

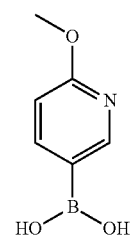

Precursor 30

Precursor 31
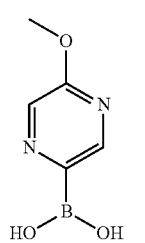
Precursor 32
Precursor 33
Precursor 34
Precursor 35
Precursor 36
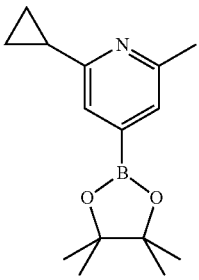
Precursor 37
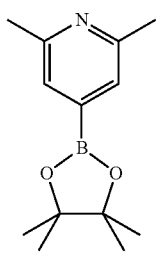
Precursor 38
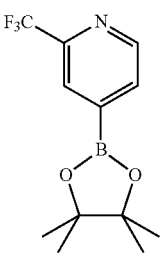
Precursor 39
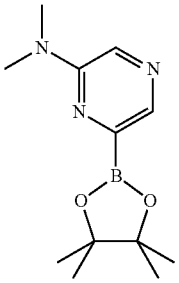
Precursor 40
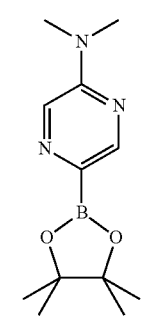
Precursor 41
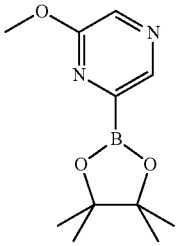

Precursor 42

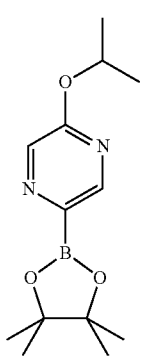

Precursor 43

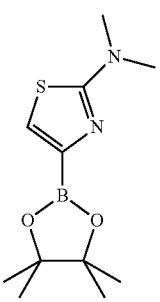

Precursor 44

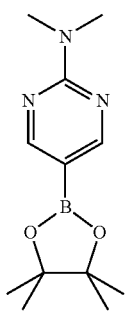

Example 15

Synthesis of 2-isopropyl-5-(tributylstannyl)thiazole (Precursor 27)

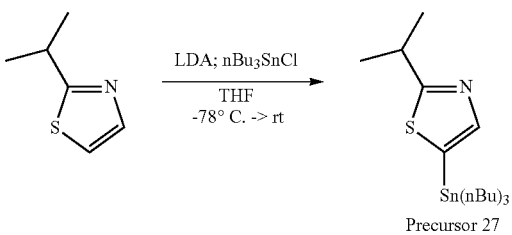

Lithium diisopropylamide (LDA; 245 mL of a 2.5 M solution, 613.2 mmol, 1.2 eq.) was added over a period of two hours to a solution of 2-isopropylthiazole ([CAS No.: 15679-10-4]; 65 g, 511 mmol, 1.0 eq.) in dry THF (1.3 L) at −78° C. After stirring for one hour at this temperature, tributyltin chloride (111 mL, 408.8 mmol, 0.8 eq.) was added dropwise. The reaction mixture was allowed to gradually warm to room temperature over about three hours, whereupon the mixture was quenched with a saturated aqueous NH$_4$Cl solution and diluted with diethyl ether. The organic layer was separated and the aqueous layer was extracted with diethyl ether. The combined organic layers were dried with MgSO$_4$ and concentrated under reduced pressure to afford 51 g (24%) of Precursor 27. $^1$H NMR (300 MHz, CHLOROFORM-d) δ ppm 0.90 (t, J=7.3 Hz, 9H) 1.06-1.16 (m, 6H) 1.25-1.39 (m, 6H) 1.42 (d, J=7.0 Hz, 6H) 1.48-1.61 (m, 6H) 3.38 (spt, J=6.9 Hz, 1H) 7.60 (s, 1H).

Precursor 28 was synthesized analogously to Precursor 27 starting from 2-cyclopropylthiazole [CAS No.: 1159821-56-3], but using n-butyllithium as a base.

Example 16

Synthesis of 2-cyclopropyl-6-methyl-4-(4,4,5,5-tetramethyl-1,3,2-dioxaborolan-2-yl)-pyridine (Precursor 36)

A mixture of 2-cyclopropyl-6-methylpyridine ([CAS No.: 41765-00-8]; 1.99 g, 14.9 mmol, 1.0 eq.), bis(pinacolato)diboron (Pin$_2$B$_2$; 3.79 g, 14.9 mmol, 1.0 eq.) and 4,4'-di-tertbutyl-2,2'-bipyridine (dtbpy; 0.08 g, 0.30 mmol, 0.02 eq.) in octane (25 mL) was flushed with nitrogen. Chloro-1,5-cyclooctadiene iridium(I) dimer ([IrCl(COD)]$_2$; 0.10 g, 0.149 mmol, 0.01 eq.) was added and the reaction mixture was stirred at 80° C. for 6 hours. The reaction mixture was cooled to room temperature and diluted with dichloromethane. Water was added and the mixture was stirred for 15 minutes. The water phase was extracted with dichloromethane (6 times), the combined organic phases were dried with anhydrous MgSO$_4$ and concentrated under reduced pressure to give 3.7 g (95%) of crude Precursor 36. The latter was used without further purification.

Precursor 37 was synthesized analogously to Precursor 36 starting from 2,6-dimethylpyridine [CAS No.: 108-48-5].

The following examples illustrate typical syntheses of the compounds of formula I. The corresponding NMR data and/or melting points are listed in table 2.

Example 17

Synthesis of Compound 7

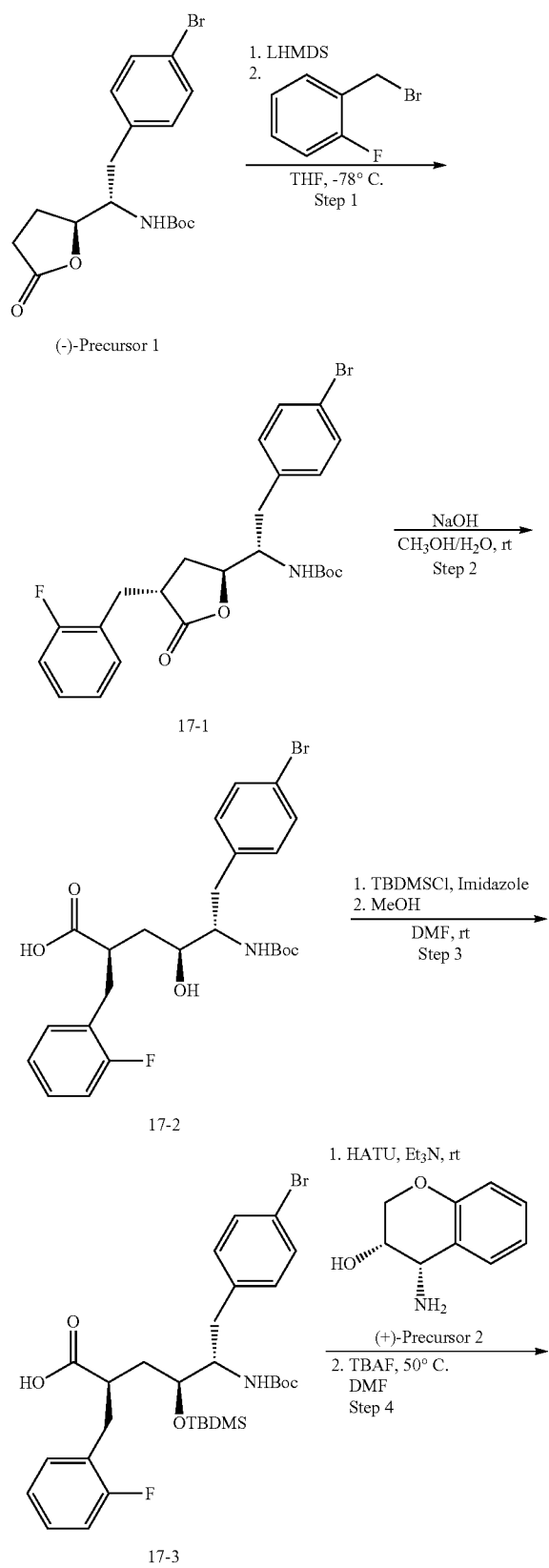

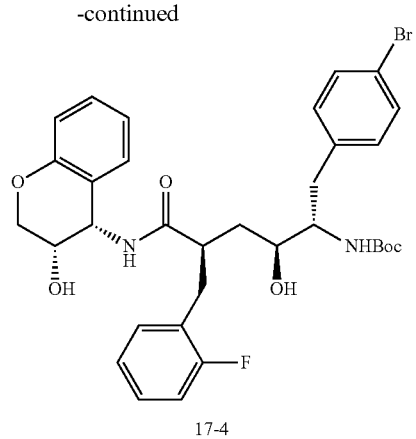

17-4

Step 1: A solution of (−)-Precursor 1 (12.5 g, 32.5 mmol, 1.0 eq.) in dry THF (100 mL) was cooled to −78° C. under nitrogen. Lithium bis(trimethylsilyl)amide (LHMDS; 68.3 mL of a 1 M solution in THF, 68.3 mmol, 2.1 eq.) was added slowly. After 30 minutes at −78° C., 2-fluorobenzyl bromide (4.19 mL, 34.2 mmol, 1.05 eq.) was added in one portion to the reaction mixture. Stirring was continued for 90 minutes at −78° C. Acetic acid (1 mL) and water were added, the mixture was allowed to warm to room temperature. Ethyl acetate was added, the organic phase was separated and successively washed with a 10% citric acid solution, a saturated aqueous NaHCO$_3$ solution and brine, dried with anhydrous MgSO$_4$ and concentrated under reduced pressure. The crude product was purified by silica gel column chromatography (eluent: heptane→heptane/ethyl acetate 7:3) to provide 10.7 g (67%) of Intermediate 17-1.

Step 2: NaOH (33.5 mL of a 1 M aqueous solution, 33.5 mmol, 5.0 eq.) was added to a solution of Intermediate 17-1 (3.3 g, 6.7 mmol, 1.0 eq.) in methanol (20 mL). The reaction mixture was stirred at room temperature for three hours. The reaction mixture was partially concentrated under reduced pressure and then acidified to pH~2-3 with a 10% citric acid solution. The white precipitate was filtered off, washed with water and dried under high vacuum. Crude Intermediate 17-2 (3.33 g, 96%) was used as such in the next step.

Step 3: Imidazole (3.08 g, 45.2 mmol, 7.0 eq.) and tert-butyldimethylsilyl-chloride (4.87 g, 32.4 mmol, 5.0 eq.) were added to a solution of Intermediate 17-2 (3.33 g, 6.47 mmol, 1.0 eq) in DMF (650 mL). The reaction was stirred at room temperature overnight. Methanol (30 mL) was added and stirring was continued until liquid chromatography-mass spectrometry (LCMS) showed complete TBDMS-deprotection of the carboxylic acid. Ethyl acetate and a 10% citric acid solution were added to the reaction mixture. The organic phase was separated, washed with brine, dried with anhydrous MgSO$_4$ and concentrated under reduced pressure. The crude product was purified by silica gel column chromatography (eluent: heptane heptane/ethyl acetate 7:4) to provide 3.7 g (91%) of pure Intermediate 17-3.

Step 4: Triethylamine (0.89 g, 8.83 mmol, 1.2 eq.), HATU (2.94 g, 7.73 mmol, 1.05 eq.) and (+)-Precursor 2 (1.54 g, 7.73 mmol, 1.05 eq.) were successively added to a solution of Intermediate 17-3 (4.60 g, 7.36 mmol, 1.0 eq.) in DMF (70 mL). The reaction mixture was stirred for one hour at room temperature. Tetrabutylammonium fluoride (TBAF, 73.64 mL of a 1 M solution in THF, 73.64 mmol, 10.0 eq.) was added and the reaction mixture was stirred at 50° C. until complete TBDMS-deprotection. Intermediate 17-4 was precipitated by the addition of a saturated aqueous Na₂CO₃ solution to the reaction mixture. The precipitate was filtered off, washed with water and dried under high vacuum. The crude product was used as such in the next step.

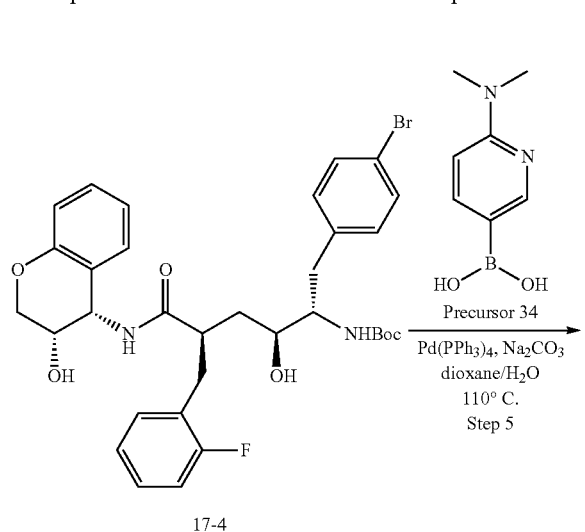

17-4

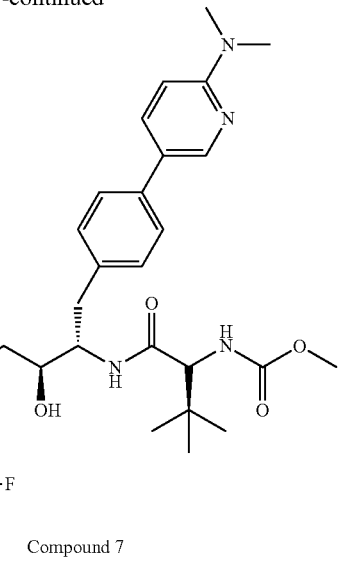

Compound 7

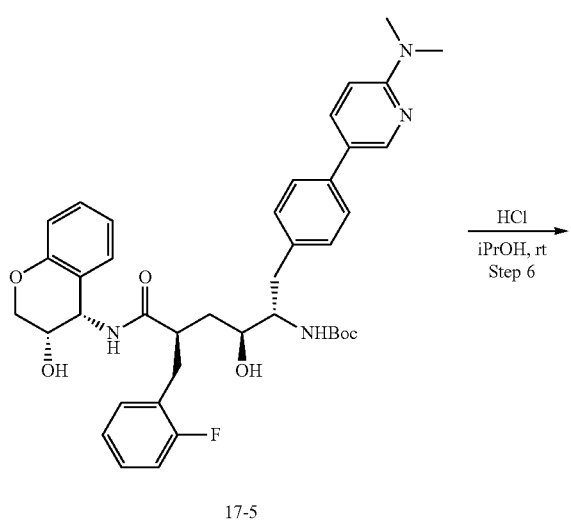

17-5

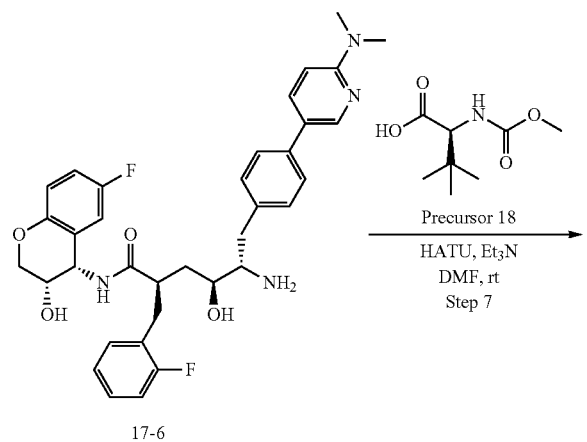

17-6

Step 5: A mixture of Intermediate 17-4 (400 mg, 0.61 mmol, 1.0 eq.), Precursor 34 (303 mg, 1.83 mmol, 3.0 eq.), tetrakis(triphenylphosphine)palladium (Pd(PPh₃)₄; 141 mg, 0.12 mmol, 0.2 eq.) and Na₂CO₃ (2.74 mL of a 2 M aqueous solution, 5.47 mmol, 9.0 eq.) in dioxane (3 mL) was stirred at 110° C. for 30 minutes (to prevent the formation of side-products short reaction times were applied) under argon. The reaction mixture was then rapidly cooled in an ice bath and a saturated aqueous Na₂CO₃ solution was added. The water layer was extracted with ethyl acetate, the combined organic phases were dried with anhydrous MgSO₄ and concentrated under reduced pressure. Crude Intermediate 17-5 was used as such in the next step.

Step 6: Crude Intermediate 17-5 was dissolved in a 5 to 6 M HCl solution in isopropanol and stirred at room temperature until complete deprotection (~30 minutes, to prevent the formation of side-products the reaction time has to be kept as short as possible). The reaction mixture was basified with a saturated aqueous Na₂CO₃ solution and extracted with ethyl acetate. The combined organic phases were washed with water, dried with anhydrous MgSO₄ and concentrated under reduced pressure to give crude Intermediate 17-6 which was used as such in the next step without purification.

Step 7: Triethylamine (246 mg, 2.43 mmol, 4.0 eq.) and HATU (266 mg, 0.69 mmol, 1.15 eq.) were successively added to a mixture of crude Intermediate 17-6 and Precursor 18 (132 mg, 0.69 mmol, 1.15 eq.) in DMF (8 mL). The reaction mixture was stirred for two hours at room temperature. Ethyl acetate was added, the organic phase was washed with a saturated Na₂CO₃ solution and water, dried with anhydrous MgSO₄ and concentrated under reduced pressure. The residue was purified by silica gel column chromatography (eluent: dichloromethane→dichloromethane/methanol 97:3) to give 144 mg (31% starting from Intermediate 17-4) of Compound 7.

Compounds 99 and 100 were prepared analogously to Compound 7. Compounds 8, 10, 13, 16, 26, and 27 were prepared analogously to Compound 7 but with Step 6 involving a TFA mediated Boc-deprotection step using the procedure as described for Step 2 in Example 27. Compound 11 was prepared analogously to Compound 7, but using a Stille cross-coupling reaction as described in Example 23 and a TFA mediated Boc-deprotection step as described for Step 2 in Example 27.

Example 18

Synthesis of Compound 33

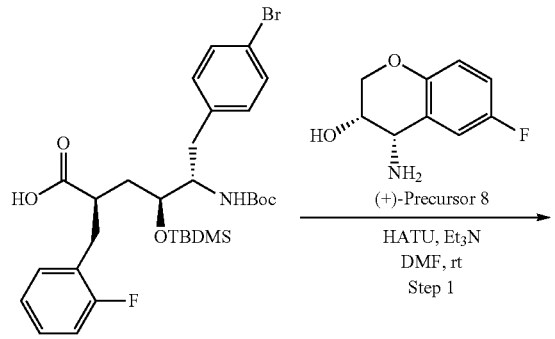

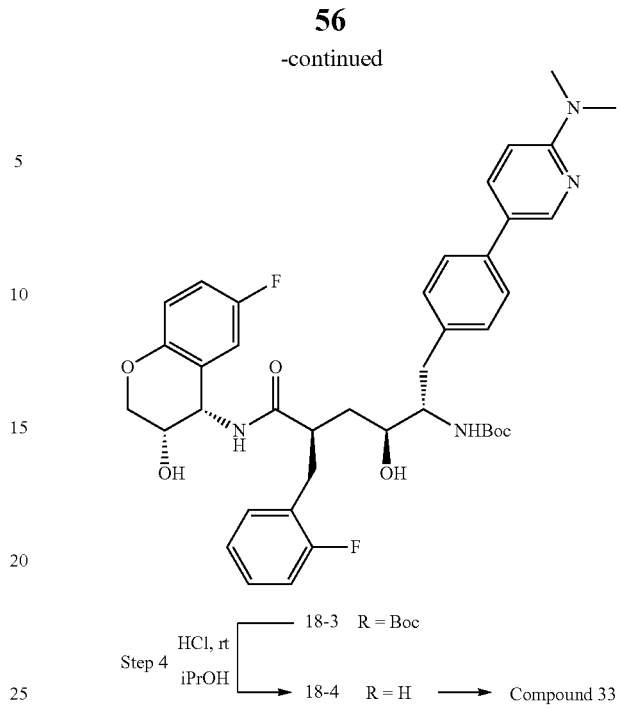

Step 1: HATU (2.36 g, 6.22 mmol, 1.1 eq.) was added to a solution of Intermediate 17-3 (3.53 g, 5.65 mmol, 1.0 eq.), (+)-Precursor 8 (1.04 g, 5.65 mmol, 1.0 eq.) and triethylamine (1.72 g, 16.95 mmol, 3.0 eq.) in DMF (25 mL). The reaction mixture was stirred for one hour at room temperature. The reaction mixture was diluted with ethyl acetate and washed a 10% citric acid solution, a saturated $Na_2CO_3$ solution and brine, dried with $MgSO_4$ and concentrated under reduced pressure to give 4.48 g (96%) of crude Intermediate 18-1. The crude product was used as such in the next step.

Step 2: A mixture of Intermediate 18-1 (4.33 g, 5.48 mmol, 1.0 eq.), Precursor 34 (1.82 g, 10.96 mmol, 2.0 eq.), $Pd(PPh_3)_4$ (0.63 g, 0.55 mmol, 0.1 eq.) and $Na_2CO_3$ (30 mL of a 2 M aqueous solution, 60.3 mmol, 11.0 eq.) in dioxane (100 mL) was stirred at 100° C. for 50 minutes (to prevent the formation of side-products the reaction time has to be kept as short as possible) under nitrogen. The reaction mixture was then rapidly cooled in an ice bath and a saturated aqueous $Na_2CO_3$ solution was added. The water layer was extracted with ethyl acetate, the combined organic phases were washed with brine, dried with anhydrous $MgSO_4$ and concentrated under reduced pressure. The residue was purified by silica gel column chromatography (eluent: dichloromethane→dichloromethane/methanol 95:5) to give 4.95 g (92%) of Intermediate 18-2.

Step 3: TBAF (10.9 mL of a 1 M solution in THF, 10.97 mmol, 2.0 eq.) was added to a solution of Intermediate 18-2 (4.56 g, 5.49 mmol, 1.0 eq.) in THF (30 mL). The reaction mixture was stirred at 50° C. until complete deprotection. Water was added, the precipitate was filtered off, thoroughly washed with water and dried under high vacuum to give 3.77 g (86%) of Intermediate 18-3.

Intermediate 18-3 was further converted to Compound 33 according to the procedures as described for Step 6 and Step 7 in Example 17.

Compound 35 was prepared analogously to Compound 33.

Example 19

Synthesis of Compound 66

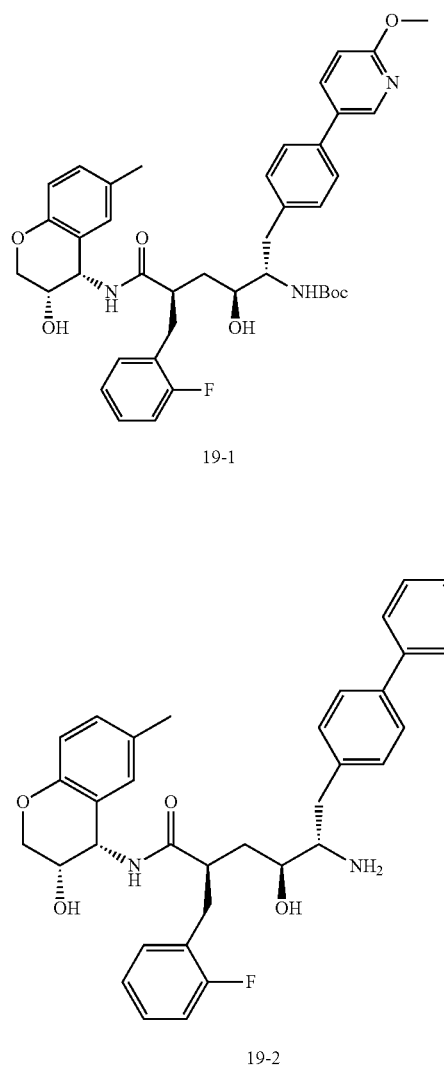

Intermediate 19-1 was prepared using the procedures as exemplified for the preparation of Intermediate 17-5.

NaI (984 mg, 6.56 mmol, 5.5 eq.) and chlorotrimethylsilane (TMSCl; 584 mg, 5.37 mmol, 4.5 eq.) were added to a solution of Intermediate 19-1 in acetonitrile (10 mL). The reaction mixture was stirred at room temperature for two hours. Methanol and an aqueous NaOH solution (12 mL of 1 M NaOH solution, 11.9 mmol, 10.0 eq.) were added, stirring was continued for an additional 30 minutes. The reaction mixture was partially concentrated under reduced pressure, ethyl acetate and water were added. The water layer was separated and extracted with ethyl acetate, the combined organic phases were dried with MgSO$_4$ and concentrated under reduced pressure. The residue was purified by silica gel column chromatography (eluent: dichloromethane→dichloromethane/methanol 93:7) to give 360 mg (50%) of Intermediate 19-2.

Intermediate 19-2 was converted to Compound 66 according to the procedure as described for Step 7 in Example 17.

Compounds 36, 40, 85 and 92 were prepared analogously to Compound 66.

Example 20

Synthesis of Compound 96

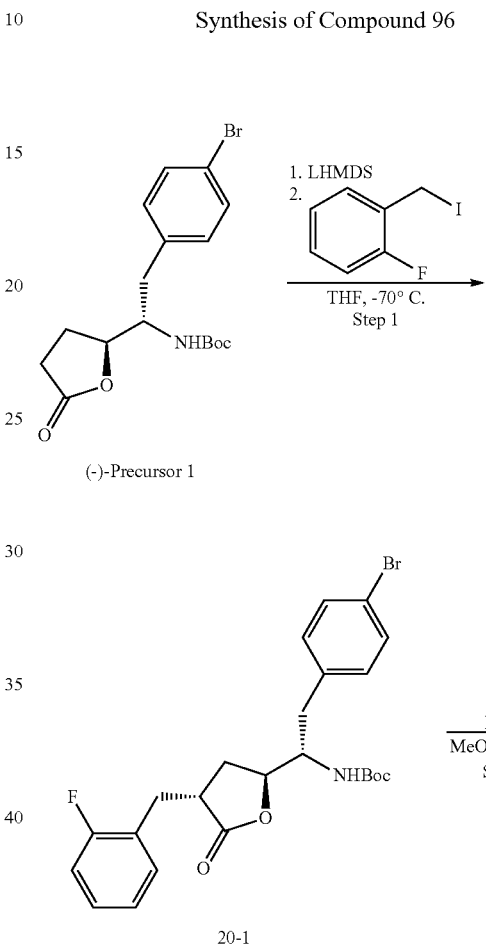

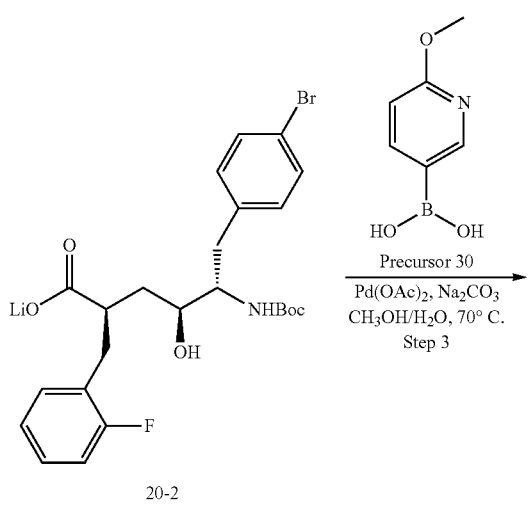

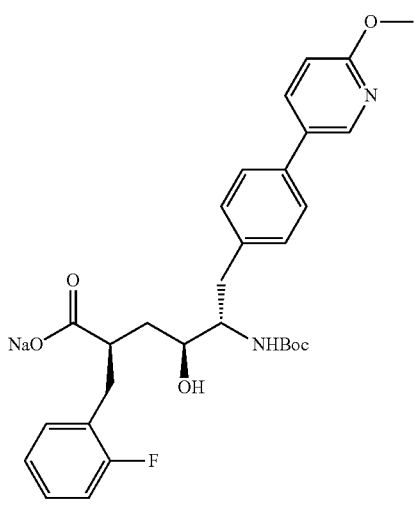

20-3

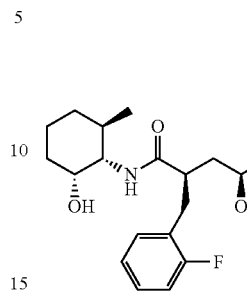

(−)-Precursor 14b

HATU, Et₃N
CH₃CN, rt
Step 5

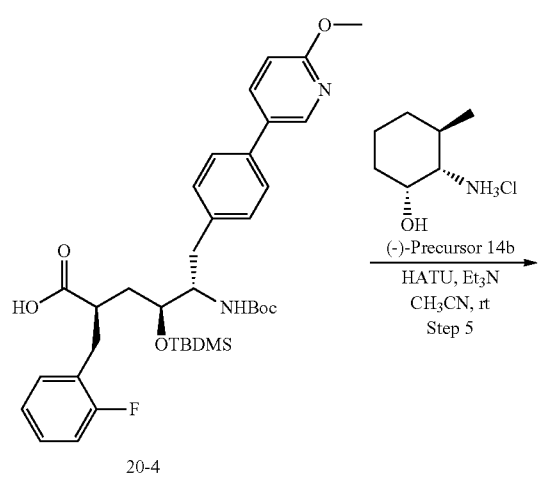

20-4

1. TMSCl, NaI
2. TBAF

CH₃CN, 5° C.
Step 6

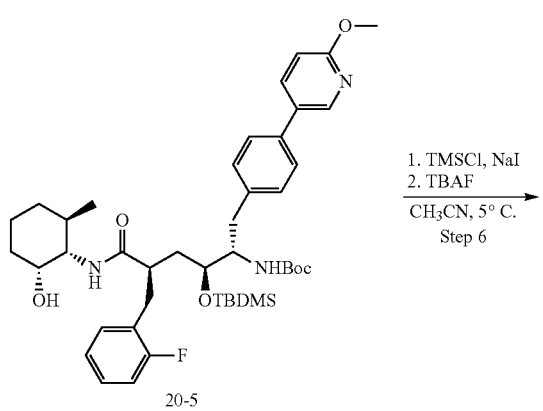

20-5

1. TBDMSCl, Imidazole
2. MeOH

DMF, rt
Step 4

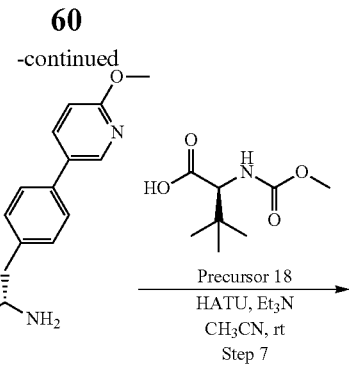

20-6

Precursor 18
HATU, Et₃N
CH₃CN, rt
Step 7

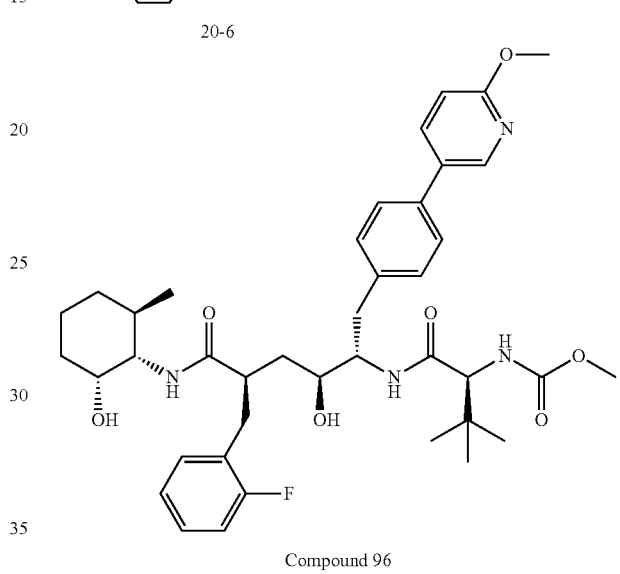

Compound 96

Step 1: A solution of (−)-Precursor 1 (54.0 g, 131 mmol, 1.0 eq.) in dry THF (1000 mL) was cooled to −70° C. under nitrogen. Lithium bis(trimethylsilyl)amide (306.8 mL of a 1 M solution in THF, 307 mmol, 2.35 eq.) was dropwise added over a period of one hour, after which the reaction mixture was stirred for an extra four hours. A solution of 2-fluorobenzyl iodide (34.0 g, 144 mmol, 1.1 eq.) in THF (100 mL) was added to the reaction mixture over one hour. Stirring was continued for 60 minutes at −70° C. Propionic acid and water were added, the mixture was allowed to warm to room temperature. The mixture was extracted with ethyl acetate, the organic phase was washed with water, dried with anhydrous Na₂SO₄ and concentrated under reduced pressure. The crude product was purified by silica gel column chromatography (eluent: petroleum ether/ethyl acetate 40:1) to provide 46.3 g (72%) of Intermediate 20-1.

Step 2: LiOH (1.4 L of a 1 M aqueous solution, 1.4 mol, 5.0 eq.) was dropwise added to a solution of Intermediate 20-1 (140 g, 284 mmol, 1.0 eq.) in methanol (3.5 L) at room temperature. The reaction mixture was stirred at room temperature until no more starting material was left. The reaction mixture was concentrated under reduced pressure and filtered. The precipitate was filtered off, washed with water and dried under vacuum at 50° C. to give 120 g (82%) of Intermediate 20-2.

Step 3: A 3 L reaction flask was charged with water and stirred at reflux temperature for 30 minutes under N₂. After the water was cooled to 40° C., methanol (300 mL), Intermediate 20-2 (100 g, 194 mmol, 1.0 eq.), Na₂CO₃ (83 g, 783 mmol, 4.0 eq.), Pd(OAc)₂ (661 mg, 2.9 mmol, 0.015 eq.) and Precursor 30 (60 g, 392 mmol, 2.0 eq.) were successively added. The reaction mixture was degassed with N₂ and heated to 75° C. over 10 minutes. The reaction mixture was stirred at 75° C. for 30 minutes and then cooled to room temperature. The precipitate was filtered off, washed with a water/methanol mixture (3:1, 100 mL) and dried under vacuum at 50° C. to give 108 g (99%) of Intermediate 20-3.

Step 4: Intermediate 20-3 was converted to Intermediate 20-4 with 70% yield using the procedure as described for Step 3 in Example 17.

Step 5: Triethylamine (2.67 g, 38.7 mmol, 3.0 eq.) was dropwise added to mixture of Intermediate 20-4 (8.45 g, 12.9 mmol, 1.0 eq.), HATU (5.15 g, 13.6 mmol, 1.05 eq.) and (−)-Precursor 14 (2.25 g, 13.6 mmol, 1.05 eq.) in acetonitrile (20 mL). After the reaction mixture was stirred at room temperature for one hour the pH of the reaction solution was adjusted to 8-9 by the addition of an aqueous Na₂CO₃/NaHCO₃ solution. Extraction was carried out with ethyl acetate, the combined organic phases were washed with water, dried with Na₂SO₄ and concentrated under reduced pressure to afford 12.4 g (86%) of Intermediate 20-5.

Step 6: A mixture of Intermediate 20-5 (12.44 g, 16.3 mmol, 1.0 eq.) and NaI (15.86 g, 105.8 mmol, 6.5 eq.) in acetonitrile (130 mL) was stirred at 0-5° C. A solution of TMSCl (9.76 g, 89.5 mmol, 5.5 eq.) in acetonitrile (20 mL) was dropwise added over a period of one hour. Stirring was continued until complete Boc-deprotection (~90 minutes). TBAF (163 mL of a 2 M solution in THF, 326 mmol, 20.0 eq.) was dropwise added over five hours to the reaction mixture at 0-5° C. The reaction mixture was stirred overnight at 30° C. The pH was adjusted to 8-9 by the addition of an aqueous Na₂CO₃/NaHCO₃ solution. Extraction was carried out with dichloromethane, the combined organic phases were washed with water, dried with Na₂SO₄ and concentrated under reduced pressure. The residue was purified by silica gel column chromatography (eluent: dichloromethane/methanol 50:1) to give 8.0 g (90%) of Intermediate 20-6.

Step 7: Intermediate 20-6 was converted to Compound 96 according to the procedure as described for Step 7 in Example 17.

Compounds 45, 52, 93 and 67 were prepared analogously to Compound 96.

For Compound 52 the structure is:

For Compound 93 its synthesis is the same as above mentioned up to Step 4, but as of Step 5, starting with Intermediate 20-4, the synthesis is as follows:

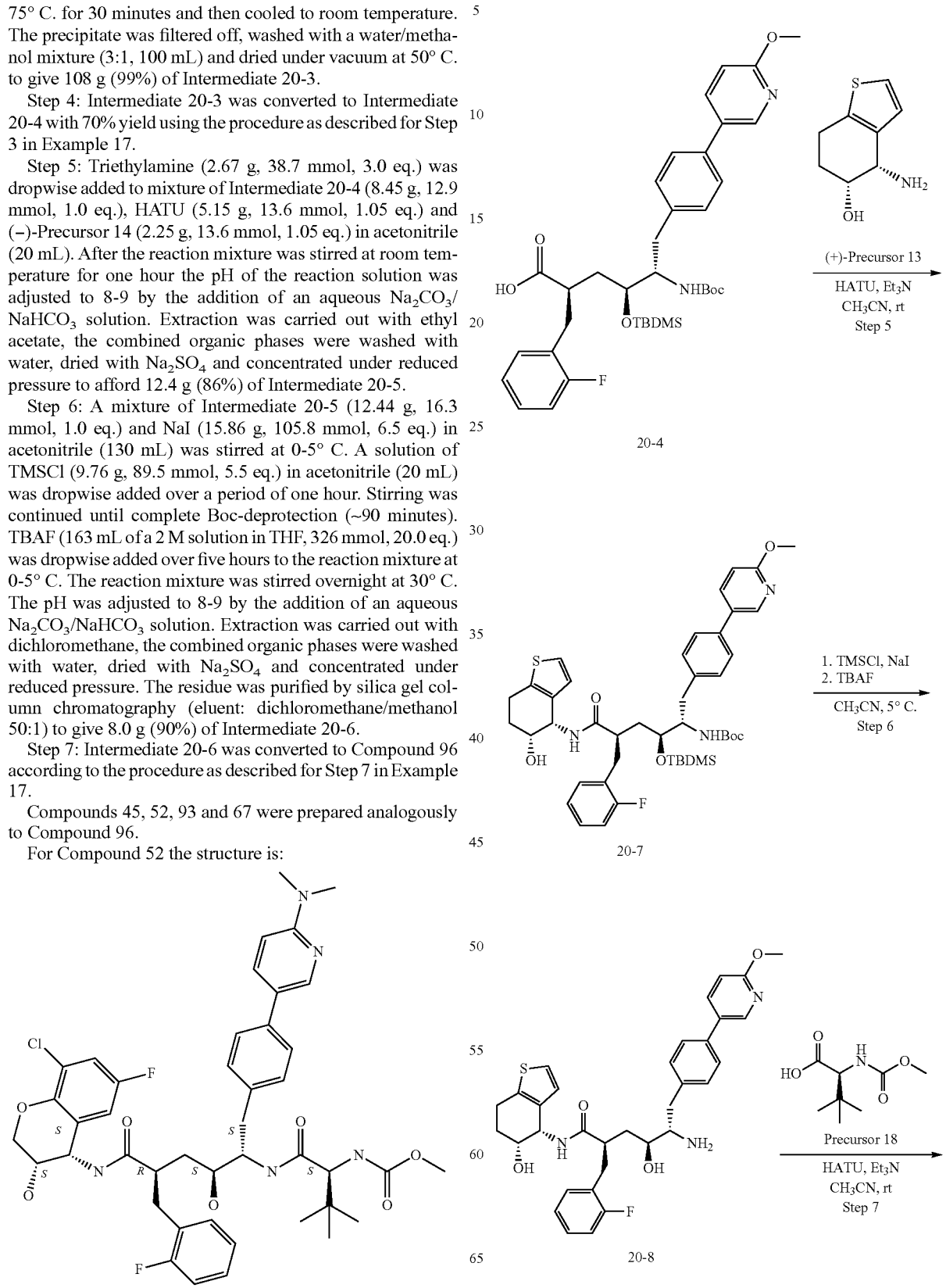

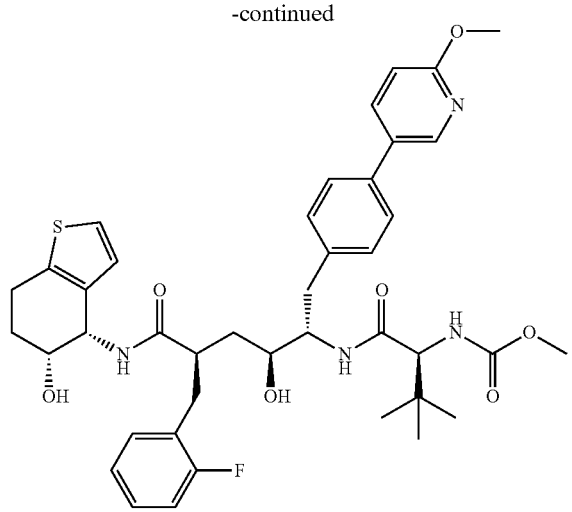

Compound 93

Step 5: Triethylamine (31 g, 306 mmol, 2.0 eq.) was dropwise added to mixture of Intermediate 20-4 (27.2 g, 153 mmol, 1.0 eq.), HATU (61.2 g, 161 mmol, 1.05 eq.) and (+)-Precursor 13 (2.25 g, 13.6 mmol, 1.05 eq.) in acetonitrile (700 mL). After the reaction mixture was stirred at room temperature for one hour the pH of the reaction solution was adjusted to 8-9 by the addition of an aqueous $Na_2CO_3$/$NaHCO_3$ solution. Extraction was carried out with ethyl methyl tert-butyl ether, the combined organic phases were washed with water, dried with $Na_2SO_4$ and concentrated under reduced pressure to afford 122 g (99%) of Intermediate 20-7.

Step 6: A mixture of Intermediate 20-7 (122 g, 152 mmol, 1.0 eq.) and NaI (149 g, 996 mmol, 6.5 eq.) in acetonitrile (1200 mL) was stirred at 0-5° C. A solution of TMSCl (91.5 g, 842 mmol, 5.5 eq.) in acetonitrile (200 mL) was dropwise added over a period of one hour. Stirring was continued until complete Boc-deprotection (~30 minutes). TBAF (1600 mL of a 2 M solution in THF, 3.04 mol, 20.0 eq.) was dropwise added over five hours to the reaction mixture at 0-5° C. The reaction mixture was stirred overnight at 25-30° C. The pH was adjusted to 8-9 by the addition of an aqueous $Na_2CO_3$/$NaHCO_3$ solution. Extraction was carried out with dichloromethane, the combined organic phases were washed with water, dried with $Na_2SO_4$ and concentrated under reduced pressure. The residue was purified by silica gel column chromatography (eluent: dichloromethane/methanol 50:1) to give 77 g (86%) of Intermediate 20-8.

Step 7: Triethylamine (26.4 g, 264 mmol, 2.0 eq.) was added to a mixture of HATU (52.2 g, 137 mmol, 1.05 eq.), Intermediate 20-8 (77 g, 131 mmol, 1.0 eq.) and Precursor 18 (25.9 g, 137 mmol, 1.05 eq.) in DMF (770 mL). The reaction mixture was stirred for one hour at room temperature. An aqueous $Na_2CO_3$ solution and water were added, the mixture was stirred for 30 minutes. The precipitate was filtered off, washed with water and dried under vacuum at 50° C. to give 83 g crude of Compound 93. After recrystallization in a water/ethanol mixture, 78 g (79%) of Compound 93 was obtained.

Example 21

Synthesis of Compound 64

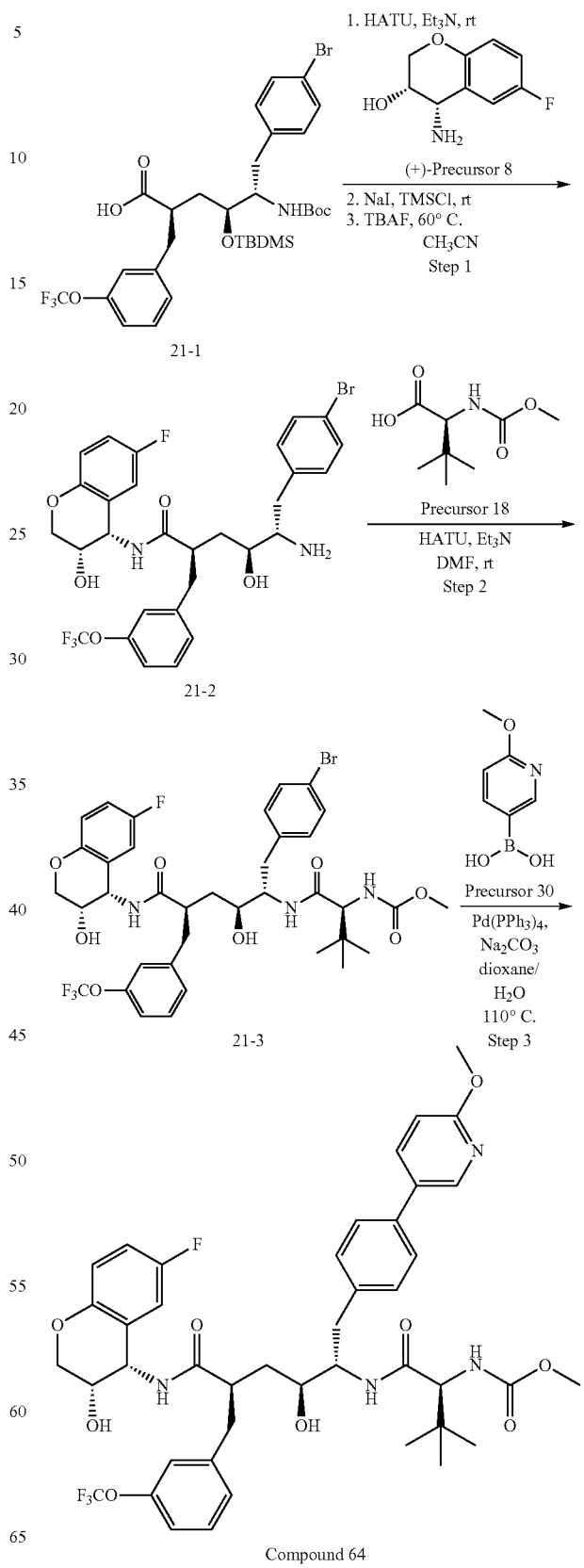

Compound 64

Intermediate 21-1 was prepared using the procedures as exemplified for the preparation of Intermediate 17-3.

Step 1: Triethylamine (119 mg, 1.18 mmol, 1.2 eq.), HATU (412 mg, 1.09 mmol, 1.1 eq.) and (+)-Precursor 8 (199 mg, 1.18 mmol, 1.1 eq.) were successively added to a solution of Intermediate 21-1 (681 mg, 0.99 mmol, 1.0 eq.) in acetonitrile (10 mL). The reaction mixture was stirred for one hour at room temperature. NaI (961 mg, 6.41 mmol, 6.5 eq.) and TMSCl (589 mg, 5.42 mmol, 5.5 eq.) were successively added to the reaction mixture, stirring was continued until complete Boc-deprotection (~2 hours). TBAF (11.8 mmol, 11.8 mL of a 1 M solution in THF, 12.0 eq.) was then added and the reaction mixture was stirred overnight at 60° C. A saturated aqueous $Na_2CO_3$ solution was added, the precipitate was filtered off and thoroughly washed with water. The crude product was purified by silica gel column chromatography (eluent: dichloromethane→dichloromethane/methanol 90:10) to give 288 mg (46%) of Intermediate 21-2.

Step 2: Triethylamine (91 mg, 0.90 mmol, 2.0 eq.) and HATU (179 mg, 0.47 mmol, 1.05 eq.) were successively added to a mixture of Intermediate 21-2 (288 mg, 0.45 mmol, 1.0 eq.) and Precursor 18 (89 mg, 0.47 mmol, 1.05 eq.) in DMF (4 mL). The reaction mixture was stirred for two hours at room temperature. Intermediate 21-3 was precipitated by the addition of a saturated aqueous $Na_2CO_3$ solution. The precipitate was filtered off, washed with water and dried under high vacuum to give 330 mg (90%) of crude Intermediate 21-3.

Step 3: A mixture of Intermediate 21-3 (165 mg, 0.203 mmol, 1.0 eq.), Precursor 30 (62 mg, 0.406 mmol, 2.0 eq.), $Pd(PPh_3)_4$ (23 mg, 0.020 mmol, 0.1 eq.) and $Na_2CO_3$ (0.91 mL of a 2 M aqueous solution, 1.83 mmol, 9.0 eq.) in dioxane (2 mL) was stirred at 110° C. for 15 minutes under argon. The reaction mixture was then rapidly cooled in an ice bath and a saturated aqueous $Na_2CO_3$ solution was added. The precipitate was filtered off, washed with water and dried under reduced pressure. The crude product was purified by silica gel column chromatography (eluent: dichloromethane→dichloromethane/methanol 95:5) to give 115 mg (67%) of Compound 64.

Compounds 41, 54, 62, 63, 65 and 94 were prepared analogously to Compound 64.

Example 22

Synthesis of Compound 44

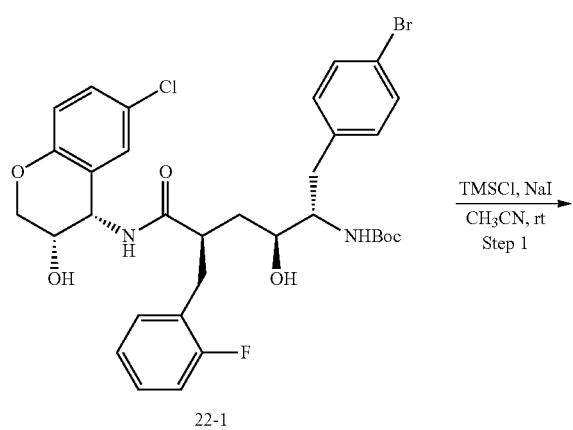

22-1

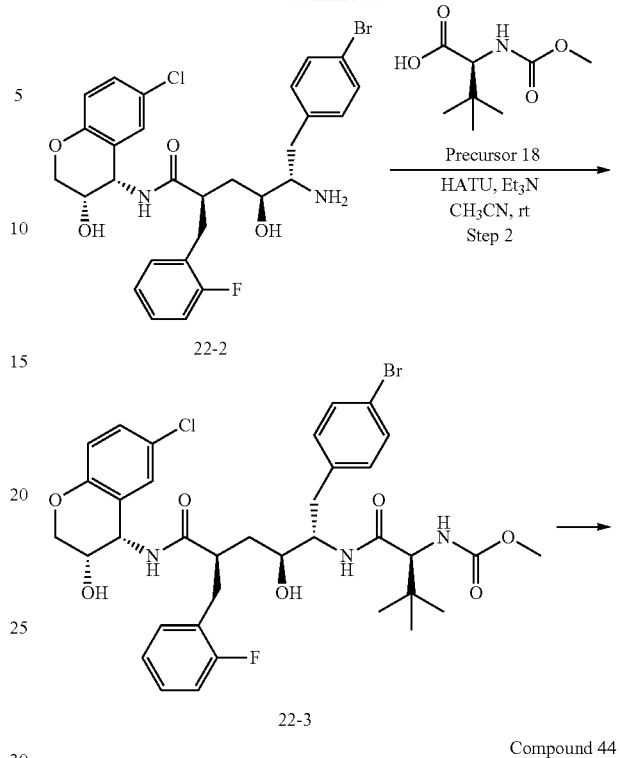

Intermediate 22-1 was prepared using the procedures as exemplified for the preparation of Intermediate 17-4. Intermediate 22-1 was converted to Intermediate 22-2 using the Boc-deprotection procedure as described in Example 19. The latter was converted to Compound 44 via intermediate 22-3 using respectively the procedures from Step 2 and Step 3 as described in Example 21.

Compounds 12, 18, 20, 21, 22, 23, 24, 25, 29, 30, 31, 39, 42, 43, 46, 48, 49 and 91 were prepared analogously to Compound 44.

Example 23

Synthesis of Compound 32

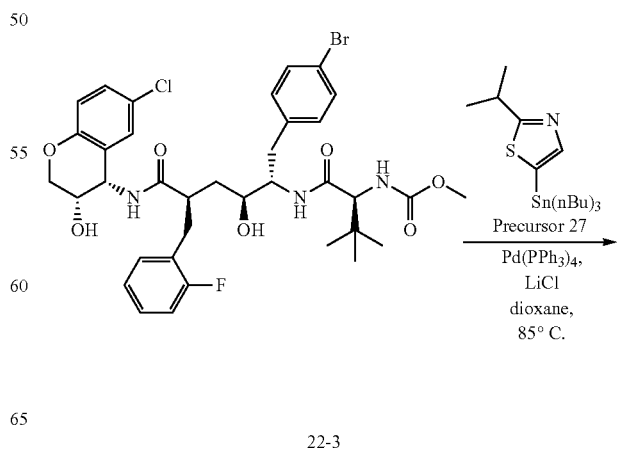

22-3

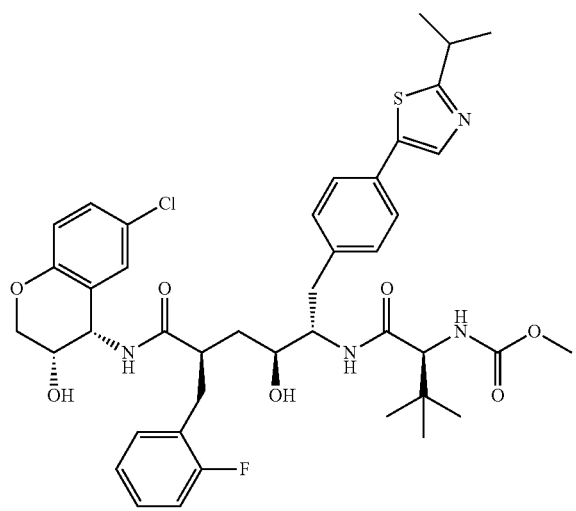

Compound 32

A mixture of Intermediate 22-3 (230 mg, 0.301 mmol, 4.0 eq.), Precursor 27 (501 mg, 1.21 mmol, 4.0 eq.), Pd(PPh$_3$)$_4$ (35 mg, 0.030 mmol, 0.1 eq.) and LiCl (26 mg, 0.603 mmol, 2.0 eq.) in dioxane (3 mL) was stirred at 85° C. for 40 minutes under argon. The reaction mixture was cooled in an ice bath and an excess of water was added. The precipitate was filtered off, washed with water and dried under reduced pressure. The crude product was purified by silica gel column chromatography (eluent: dichloromethane→dichloromethane/methanol 96:4) to give 137 mg (56%) of Compound 32.

Compounds 14, 28, and 29 were prepared analogously to Compound 32.

Example 24

Synthesis of Compound 38

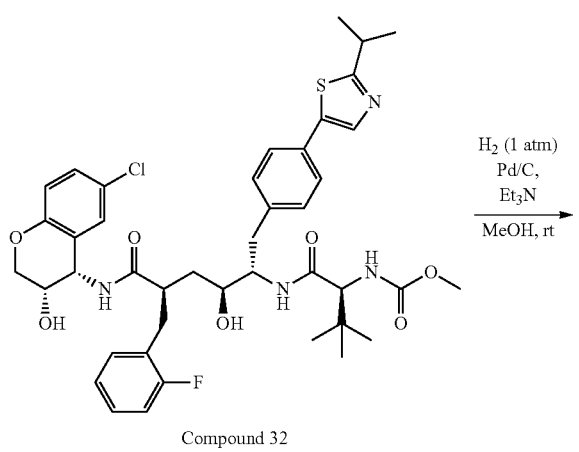

Compound 32

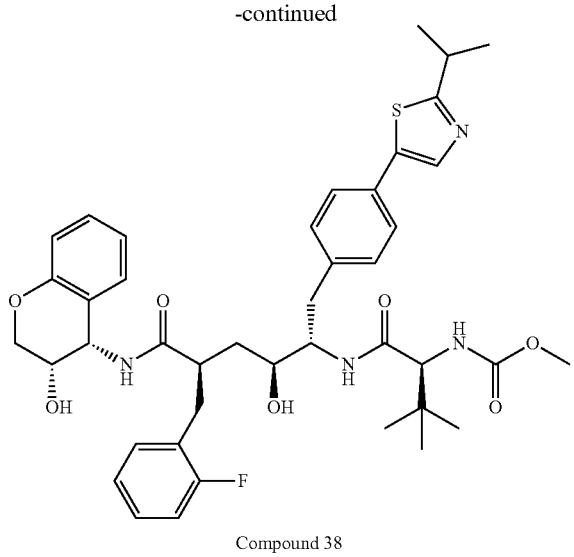

Compound 38

A solution of Compound 32 (50 mg, 0.06 mmol, 1.0 eq.) in methanol (6 mL) was hydrogenated (1.0 atm of hydrogen) at 25° C. for 90 minutes with Pd (Pd/C 10%, 50 mg) as catalyst. The reaction mixture was filtered over Celite, the filtrate was concentrated under reduced pressure to give 31 mg (61%) of Compound 38.

Example 25

Synthesis of Compound 17

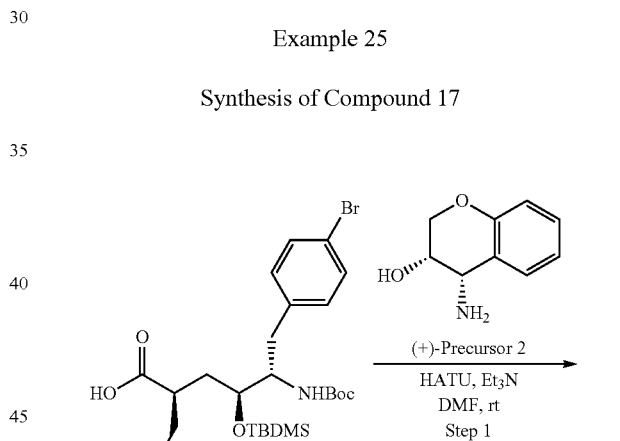

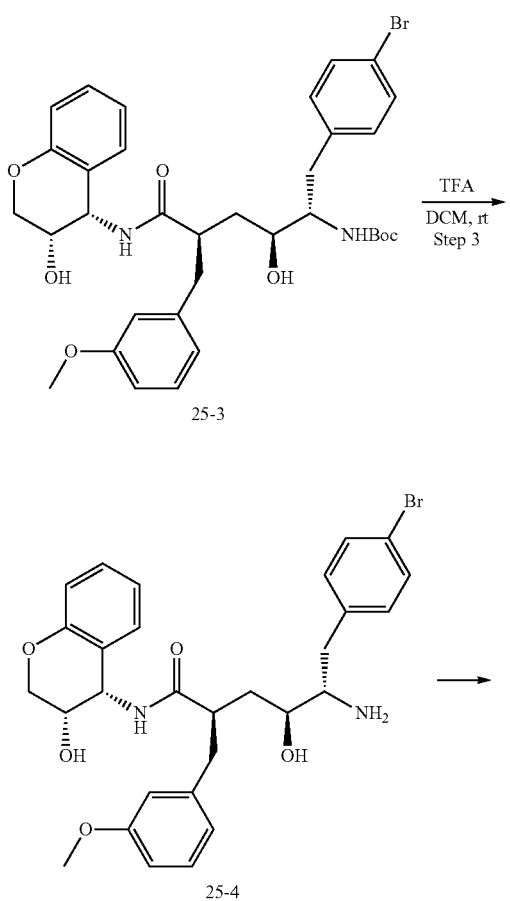

Compound 17

Intermediate 25-1 was prepared using the procedures as exemplified for the preparation of Intermediate 17-3.

Step 1: HATU (1.25 g, 3.30 mmol, 1.05 eq.) was added to a mixture of triethylamine (954 mg, 9.42 mmol, 3.0 eq.), (+)-Precursor 2 (519 mg, 3.14 mmol, 1.0 eq.) and Intermediate 25-1 (2.0 g, 3.14 mmol, 1.0 eq.) in DMF (10 mL). The reaction mixture was stirred for 30 minutes at room temperature. Ethyl acetate was added, the organic phase was washed with a saturated aqueous $Na_2CO_3$ solution and brine, dried with $MgSO_4$ and concentrated under reduced pressure. The crude product was purified by silica gel column chromatography (eluent: dichloromethane→dichloromethane/methanol 99:3) to give 1.67 g (68%) of Intermediate 25-2.

Step 2: A mixture of Intermediate 25-2 (1.67 g, 2.13 mmol, 1.0 eq.) and TBAF (32.0 mL of a 1 M solution in THF, 32.0 mmol, 15.0 eq.) in THF (40 mL) was stirred at room temperature overnight. Ethyl acetate and brine were added to the reaction mixture. The organic layer was separated, thoroughly washed with water and dried to give 1.47 g (100%) of crude Intermediate 25-3. The crude product was used as such in the next step.

Step 3: Intermediate 25-3 was converted to Intermediate 25-4 involving a TFA mediated Boc-deprotection step using the procedure as described for Step 2 in Example 27. The latter was converted to Compound 17 using respectively the procedures from Step 2 and Step 3 as described in Example 21.

Compounds 15 and 87 and were prepared analogously to Compound 17. Compound 37 was prepared analogously to Compound 17, but involving a HCl mediated Boc-deprotection step as described for Step 6 in Example 17.

Example 26

Synthesis of Compound 51

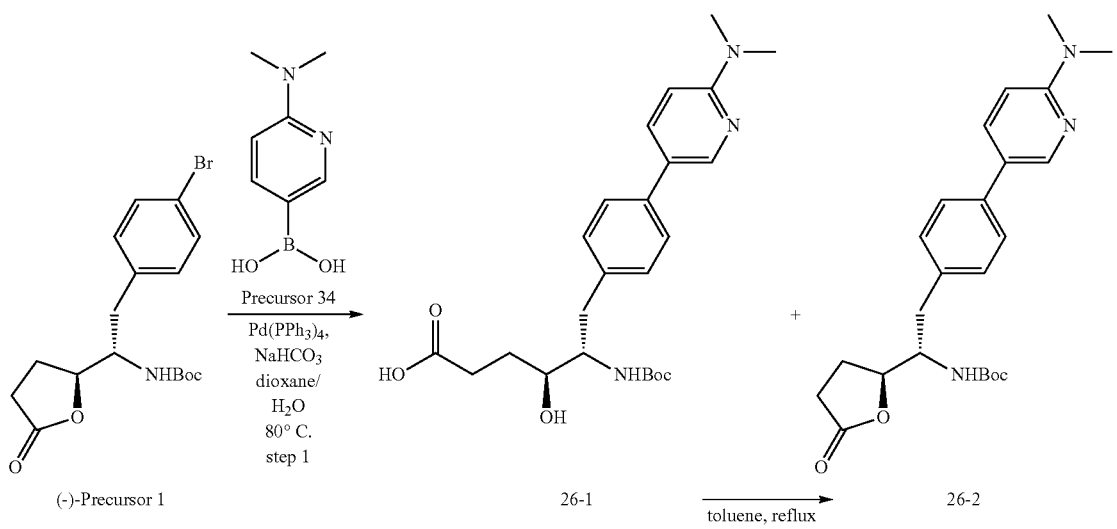

Step 1: A mixture of (−)-Precursor 1 (10.0 g, 26.0 mmol, 1.0 eq.), Precursor 34 (6.5 g, 39.0 mmol, 1.5 eq.) and an aqueous NaHCO₃ solution (21.9 g in 50 mL of water, 260.2 mmol, 10 eq.) in dioxane (200 mL) was stirred at room temperature under argon. Pd(PPh₃)₄ (1.5 g, 1.3 mmol, 0.05 eq.) was added and the reaction mixture was stirred at 80° C. for one hour and then cooled to room temperature. Ethyl acetate was added, followed by the addition of a saturated aqueous Na₂CO₃ solution. The organic and the water layer were separated, the organic layer was washed with brine and dried with anhydrous MgSO₄ to give a first batch of crude Intermediate 26-2. The water layer was acidified with a 2 M HCl solution to pH~2 and washed with ethyl acetate. Subsequently, the pH was adjusted to pH~6 with Na₂CO₃ powder and an extraction was carried out with ethyl acetate. The combined organic phases were dried with anhydrous MgSO₄ and concentrated under reduced pressure to give a crude lactone hydrolyzed side-product (Intermediate 26-1). This was refluxed in toluene under Dean-Stark conditions until re-lactonization was complete. After removal of the solvent under reduced pressure, a second bath of crude Intermediate 26-2 was obtained. Both batches were combined and purified by silica gel column chromatography (eluent: heptane/ethyl acetate 90:10→30:70) to give 7.9 g (71%) of pure Intermediate 26-2.

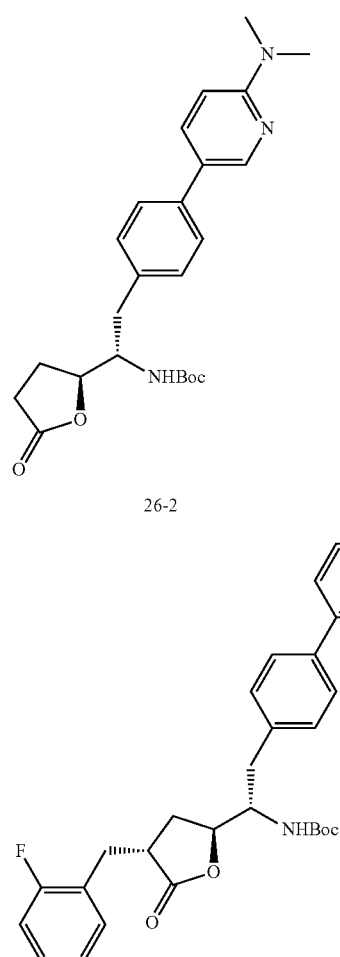

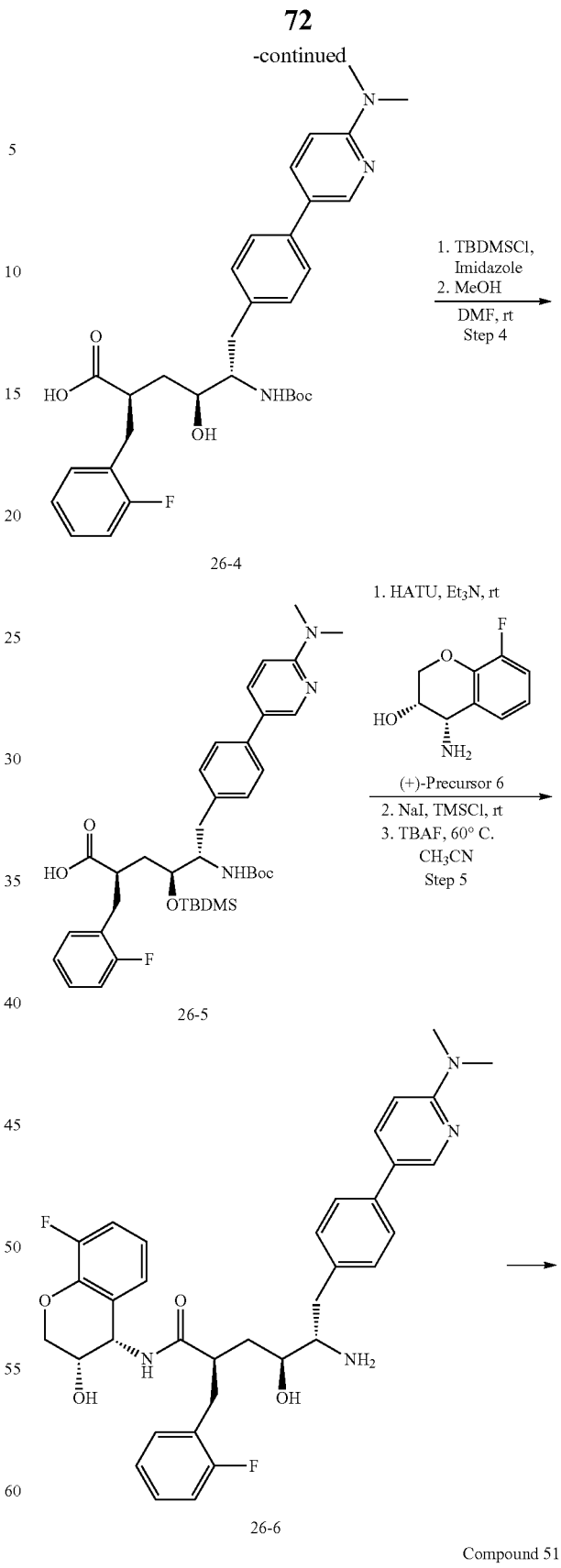

Step 2: Lactone 26-2 was converted to Intermediate 26-3 according to the procedure as described for Step 1 in Example 17. Purification by silica gel column chromatography (eluent: heptane→heptane/ethyl acetate 5:5) gave Intermediate 26-3 with 73% yield.

Step 3: NaOH (124.5 mL of a 1 M aqueous solution, 124.5 mmol, 9.3 eq.) was added to a solution of Intermediate 26-3 (7.18 g, 13.5 mmol, 1.0 eq.) in THF (120 mL). The reaction mixture was stirred at room temperature for one hour. The reaction mixture was partially concentrated under reduced pressure and then acidified with an aqueous 10% citric acid solution until pH~6. The water phase was extracted with dichloromethane, the combined organic phases were dried with anhydrous $MgSO_4$ and concentrated under reduced pressure to give 7.40 g (99%) of Intermediate 26-4.

Step 4: Intermediate 26-4 was converted to Intermediate 26-5 according to the procedure as described for Step 3 in Example 17. Purification by silica gel column chromatography (eluent: dichloromethane→dichloromethane/methanol 96:4) gave Intermediate 26-5 with 84% yield.

Step 5: Intermediate 26-5 was converted to Intermediate 26-6 using the procedure as described for Step 1 in Example 21. The latter was converted to Compound 51 using the procedure as described for Step 7 in Example 17.

Compounds 50, 58, 59, 80, 89 and 95 were prepared analogously to Compound 51. Chlorination of Compound 51 according to the procedure as described in Example 33 gave Compound 60.

Example 27

Synthesis of Compound 86

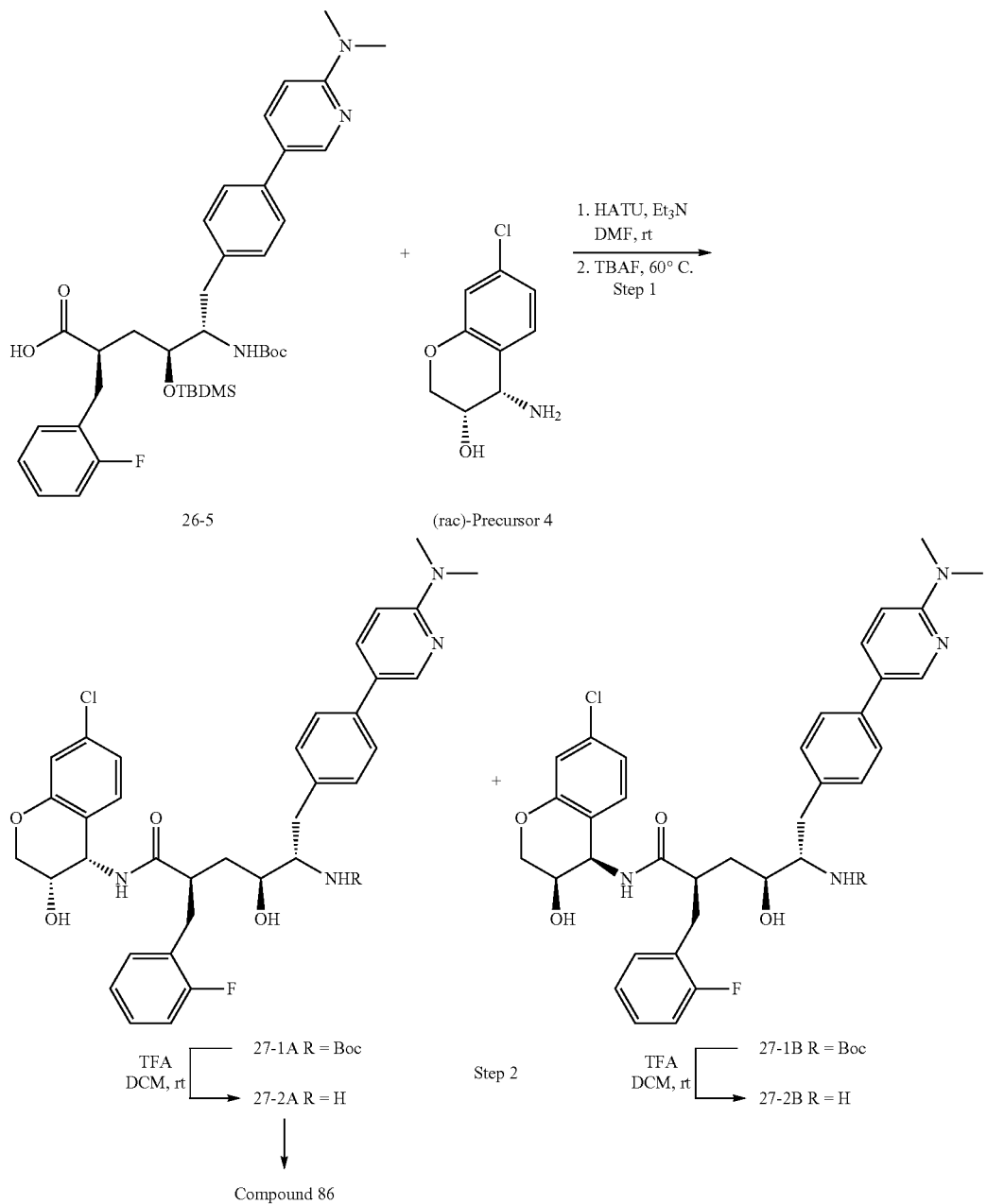

Step 1: Intermediate 26-5 was reacted with racemic (rac)-Precursor 4 using the procedure as described for Step 4 in Example 17. The crude reaction product was suspended in a mixture of acetonitrile and methanol (1:1) at reflux temperature. After cooling down to 0° C., the precipitate was filtered off to give a 1:1 mixture of Intermediate 27-1A and Intermediate 27-1B as a white powder (71%). This mixture was used as such in the next step.

Step 2: TFA (10 mL, 135 mmol, 129 eq.) was added to a 1:1 mixture of Intermediate 27-1A and Intermediate 27-1B (765 mg, 1.04 mmol, 1.0 eq.) in dichloromethane (200 mL). The reaction mixture was stirred at room temperature until LCMS showed complete conversion (~30 minutes, to prevent the formation of side-products the reaction time has to be kept as short as possible). A saturated aqueous Na$_2$CO$_3$ solution was added, the layers were separated, the water layer was extracted with dichloromethane. The combined organic phases were washed with brine, dried with anhydrous MgSO$_4$ and concentrated under reduced pressure. Both isomers were separated by silica gel column chromatography (eluent: dichloromethane→dichloromethane/methanol 93:7) to provide 320 mg (48%) of Intermediate 27-2A (first fraction) and 298 mg (45%) of Intermediate 27-2B (second fraction).

Intermediate 27-2A was converted to Compound 86 using the procedure as described for Step 7 in Example 17.

Example 28

Synthesis of Compound 61

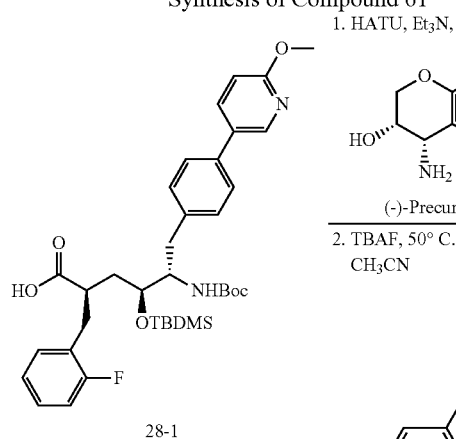

28-1

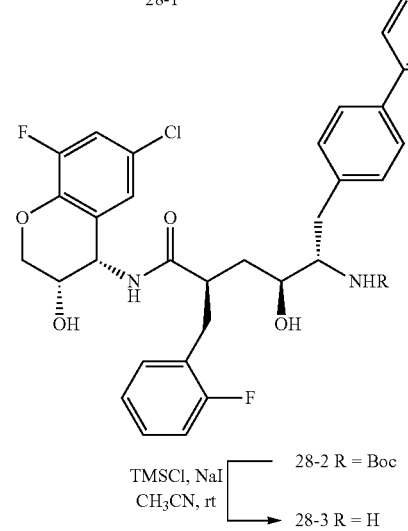

Compound 61

Intermediate 28-1, prepared analogously to Intermediate 26-5, was reacted with (−)-Precursor 11a according to the procedure as described for Step 4 in Example 17, to give Intermediate 28-2. Subsequent Boc-deprotection was accomplished applying the procedure as described in Example 19. Intermediate 28-3 was further converted to Compound 61 using the procedure as described for Step 7 in Example 17.

Compound 56, 98, 101 and 102 were prepared analogously to Compound 61.

Example 29

Synthesis of Compound 90

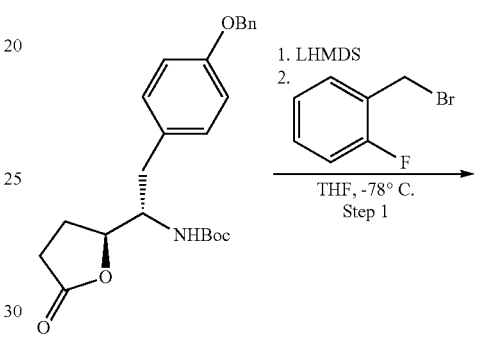

29-1

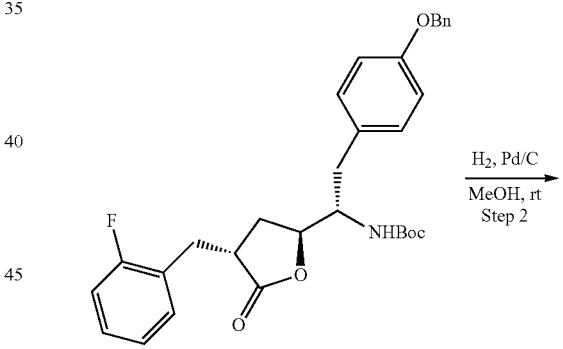

29-2

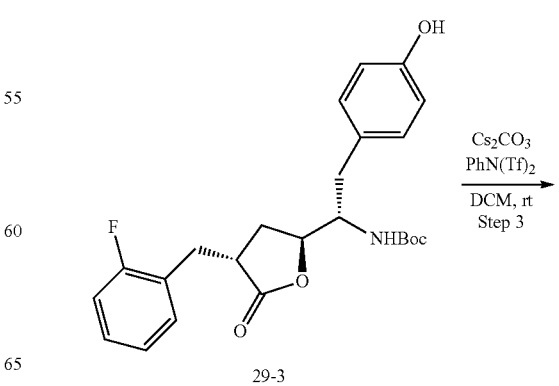

29-3

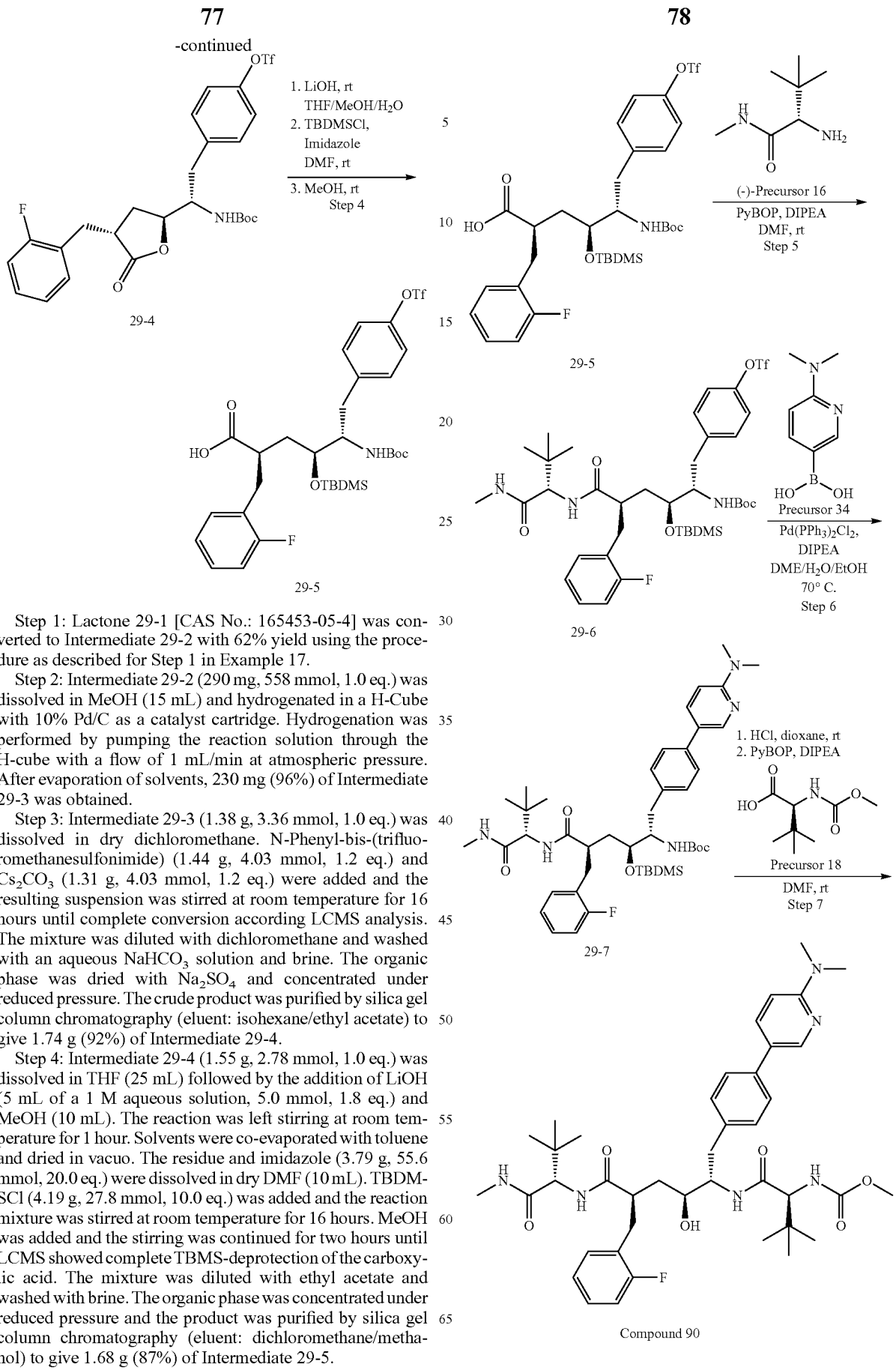

Step 1: Lactone 29-1 [CAS No.: 165453-05-4] was converted to Intermediate 29-2 with 62% yield using the procedure as described for Step 1 in Example 17.

Step 2: Intermediate 29-2 (290 mg, 558 mmol, 1.0 eq.) was dissolved in MeOH (15 mL) and hydrogenated in a H-Cube with 10% Pd/C as a catalyst cartridge. Hydrogenation was performed by pumping the reaction solution through the H-cube with a flow of 1 mL/min at atmospheric pressure. After evaporation of solvents, 230 mg (96%) of Intermediate 29-3 was obtained.

Step 3: Intermediate 29-3 (1.38 g, 3.36 mmol, 1.0 eq.) was dissolved in dry dichloromethane. N-Phenyl-bis-(trifluoromethanesulfonimide) (1.44 g, 4.03 mmol, 1.2 eq.) and $Cs_2CO_3$ (1.31 g, 4.03 mmol, 1.2 eq.) were added and the resulting suspension was stirred at room temperature for 16 hours until complete conversion according LCMS analysis. The mixture was diluted with dichloromethane and washed with an aqueous $NaHCO_3$ solution and brine. The organic phase was dried with $Na_2SO_4$ and concentrated under reduced pressure. The crude product was purified by silica gel column chromatography (eluent: isohexane/ethyl acetate) to give 1.74 g (92%) of Intermediate 29-4.

Step 4: Intermediate 29-4 (1.55 g, 2.78 mmol, 1.0 eq.) was dissolved in THF (25 mL) followed by the addition of LiOH (5 mL of a 1 M aqueous solution, 5.0 mmol, 1.8 eq.) and MeOH (10 mL). The reaction was left stirring at room temperature for 1 hour. Solvents were co-evaporated with toluene and dried in vacuo. The residue and imidazole (3.79 g, 55.6 mmol, 20.0 eq.) were dissolved in dry DMF (10 mL). TBDMSCl (4.19 g, 27.8 mmol, 10.0 eq.) was added and the reaction mixture was stirred at room temperature for 16 hours. MeOH was added and the stirring was continued for two hours until LCMS showed complete TBMS-deprotection of the carboxylic acid. The mixture was diluted with ethyl acetate and washed with brine. The organic phase was concentrated under reduced pressure and the product was purified by silica gel column chromatography (eluent: dichloromethane/methanol) to give 1.68 g (87%) of Intermediate 29-5.

Step 5: DIPEA (1.5 mL, 8.65 mmol, 4.0 eq.) was added to a stirred solution of Intermediate 29-5 (1.5 g, 2.16 mmol, 1.0 eq.), (−)-Precursor 16 (437 mg, 3.03 mmol, 1.4 eq.) and (benzotriazol-1-yloxy)tripyrrolidinophosphonium hexafluorophosphate (PyBOP, 1.35 g, 2.59 mmol) in dry DMF (15 mL). After two hours the mixture was diluted with dichloromethane (50 mL) and washed with aqueous $NaHCO_3$, dried and concentrated to dryness to give crude Intermediate 29-6 which was used as such in the next step.

Step 6: A suspension of crude Intermediate 29-6, the HCl salt of Precursor 34 (109 mg, 0.55 mmol), $Pd(PPh_3)_2Cl_2$ (35 mg, 0.055 mmol) and DIPEA (288 mg, 2.23 mmol) in a dimethoxyethane/water/ethanol 7:3:1 mixture was stirred at 70° C. for 16 hours. The reaction mixture was concentrated under reduced pressure, the residue was purified by silica gel column chromatography (eluent: hexane/ethyl acetate 93:7→40:60) to give 360 mg (21% over two steps) of Intermediate 29-7.

Step 7: HCl (1.25 mL of a 4 M solution in dioxane) was added to a solution of Intermediate 29-7 (180 mg, 0.23 mmol, 1.0 eq.) in dioxane (5 mL) and methanol (1 mL). After 40 minutes stirring at room temperature, the mixture was concentrated to dryness and the residue dried under vacuum. The residue was redissolved in DMF (10 mL), Precursor 18 (51 mg, 0.27 mmol, 1.2 eq.), PyBOP (142 mg, 0.27 mmol, 1.2 eq.) and DIPEA (121 mg, 0.94 mmol, 4.0 eq.) were added. The reaction mixture was stirred for four hours at room temperature. Dichloromethane was added, the organic layer was washed with aqueous $NaHCO_3$, dried with $MgSO_4$ and concentrated under reduced pressure. Purification by preparative reversed phase HPLC gave 79 mg (46%) of Compound 90.

Example 30

Synthesis of Compound 84

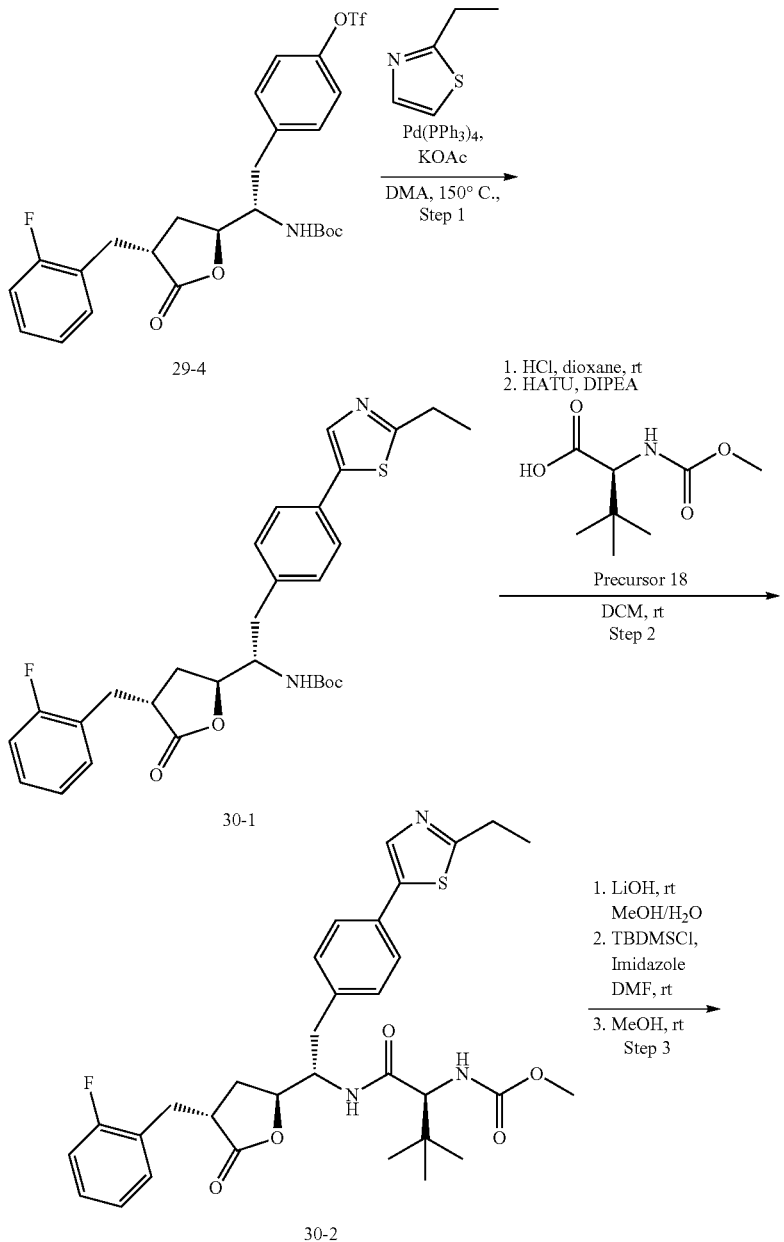

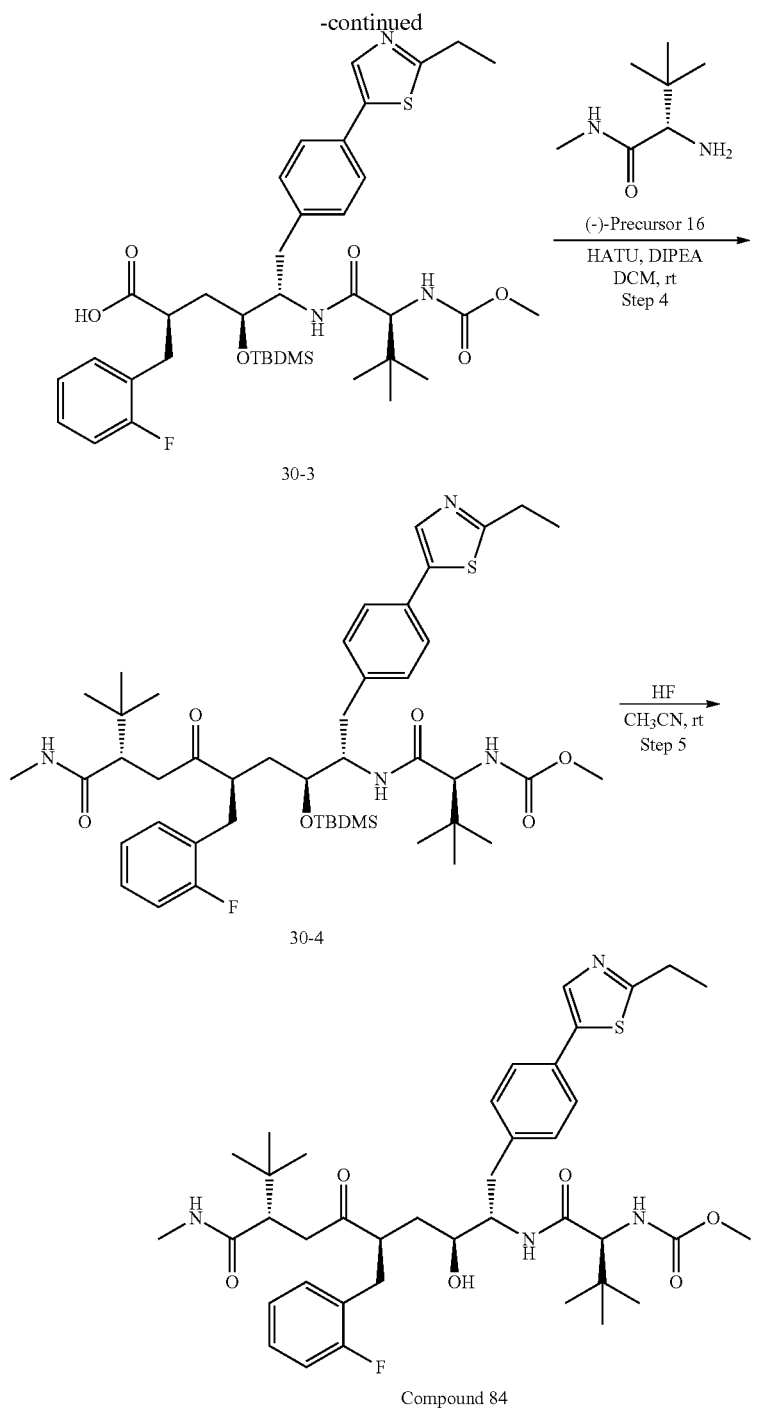

Compound 84

Step 1: Intermediate 29-4 (430 mg, 0.765 mmol) dissolved in N,N-dimethylacetamide (DMA; 11 mL) was loaded in a microwave vial together with 2-ethylthiazole ([CAS No.: 15679-09-1]; 433 mg, 3.83 mmol, 5.0 eq.), KOAc (113 mg, 1.17 mmol, 1.5 eq.) and Pd(PPh$_3$)$_4$ (44 mg, 38.3 µmol, 0.05 eq.). The reaction mixture was degassed with N$_2$ and then heated in a microwave at 150° C. for one hour. The reaction mixture was diluted with dichloromethane and washed with aqueous 1 M HCl, a saturated NaHCO$_3$ solution and brine. The organic phase was dried with Na$_2$SO$_4$ and concentrated under reduced pressure. The residue was purified by silica gel column chromatography (eluent: heptane/ethyl acetate) to give 169 mg (42%) of Intermediate 30-1.

Step 2: HCl (10 mL of a 4 M solution in dioxane) was added to Intermediate 30-1 (169 mg, 0.323 mmol, 1.0 eq.), the mixture was stirred at room temperature for one hour. The reaction mixture was freeze dried over night. The residue was redissolved in dichloromethane (10 mL), followed by the addition of Precursor 18 (67 mg, 0.355 mmol, 1.1 eq.) and DIPEA (281 µL, 1.62 mmol, 5.0 eq.). The reaction mixture was cooled to 0° C., HATU (129 mg, 0.339 mmol, 1.05 eq.) was added and stirring was continued at room temperature for three hours. The reaction mixture was washed with 1 M HCl, a saturated aqueous NaHCO$_3$ solution and brine. The organic phase was dried with Na$_2$SO$_4$ and concentrated under reduced pressure to give 185 mg (96%) of Intermediate 30-2.

Step 3: Intermediate 30-2 was converted to Intermediate 30-3 according to the procedure as described for Step 4 in Example 29 (49% yield).

Step 4: HATU (74 mg, 194 μmol, 1.1 eq.) was added to a solution of Intermediate 30-3 (128 mg, 176 μmol, 1.0 eq.), (−)-Precursor 16 (38 mg, 264 μmol, 1.5 eq.) and DIPEA (153 μL, 880 μmol, 5.0 eq.) in DCM (5 mL) at 0° C. The reaction mixture was stirred to room temperature for two hours. The reaction mixture was diluted with DCM and washed with an aqueous 1 M HCl solution, saturated aqueous NaHCO$_3$ and brine. The organic phase was dried with Na$_2$SO$_4$ and concentrated under reduced pressure. The residue was purified by silica gel column chromatography (eluent: heptane/ethyl acetate) to give 35 mg (23%) of Intermediate 30-4.

Step 5: A solution of Intermediate 30-4 (35 mg, 41 μmol, 1.0 eq.) in CH$_3$CN (3 mL) was cooled to 0° C. HF (170 μL) was dropwise added and stirring was continued at room temperature for two hours. The reaction was quenched by careful addition of a saturated aqueous NaHCO$_3$ solution, followed by ethyl acetate. Both phases were separated, the organic phase was washed with saturated aqueous NaHCO$_3$, dried with anhydrous Na$_2$SO$_4$ and evaporated under reduced pressure. The residue was purified by reversed phase preparative HPLC affording 10 mg (31%) of Compound 84.

Example 31

Synthesis of Compound 87

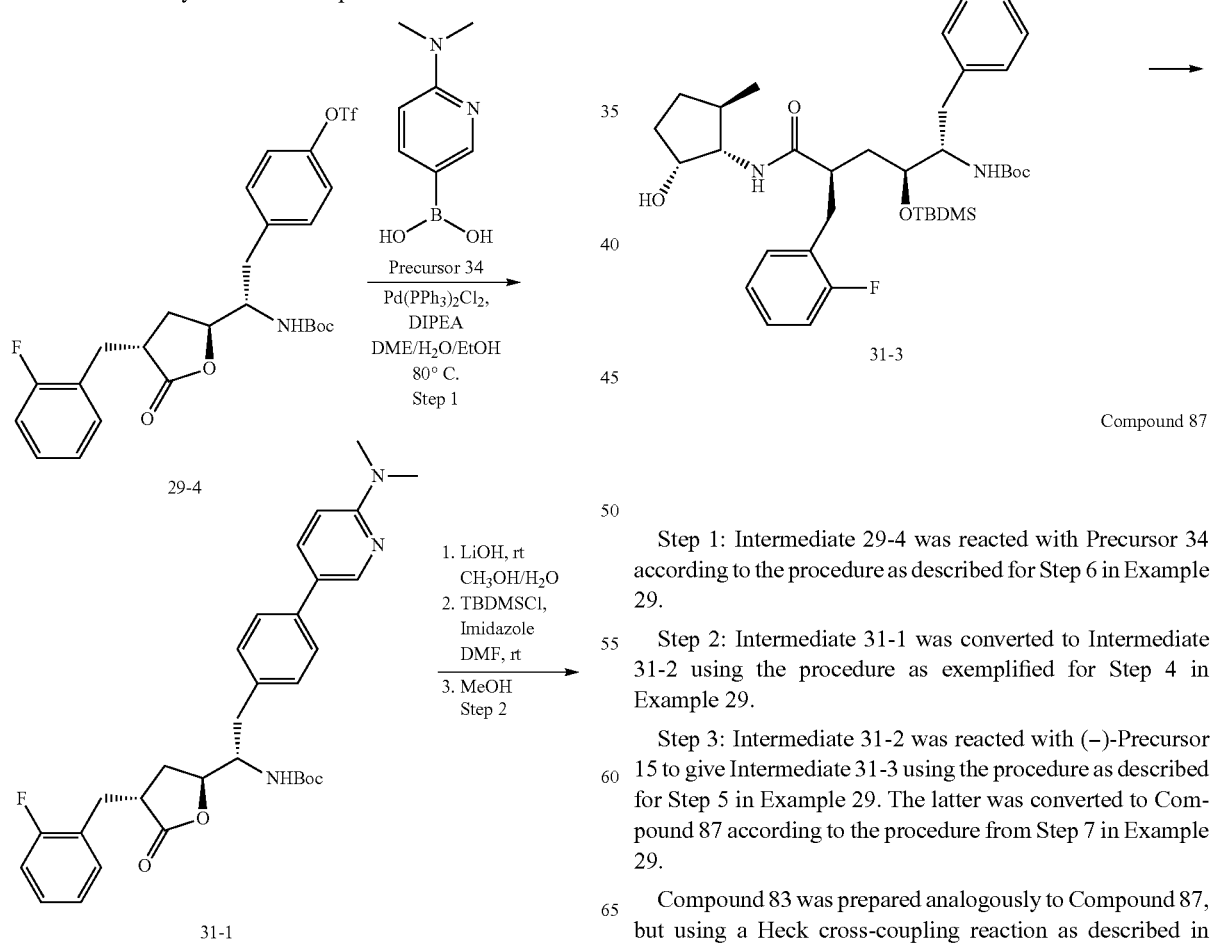

Step 1: Intermediate 29-4 was reacted with Precursor 34 according to the procedure as described for Step 6 in Example 29.

Step 2: Intermediate 31-1 was converted to Intermediate 31-2 using the procedure as exemplified for Step 4 in Example 29.

Step 3: Intermediate 31-2 was reacted with (−)-Precursor 15 to give Intermediate 31-3 using the procedure as described for Step 5 in Example 29. The latter was converted to Compound 87 according to the procedure from Step 7 in Example 29.

Compound 83 was prepared analogously to Compound 87, but using a Heck cross-coupling reaction as described in Example 30, Step 1.

Example 32

Synthesis of Compound 4

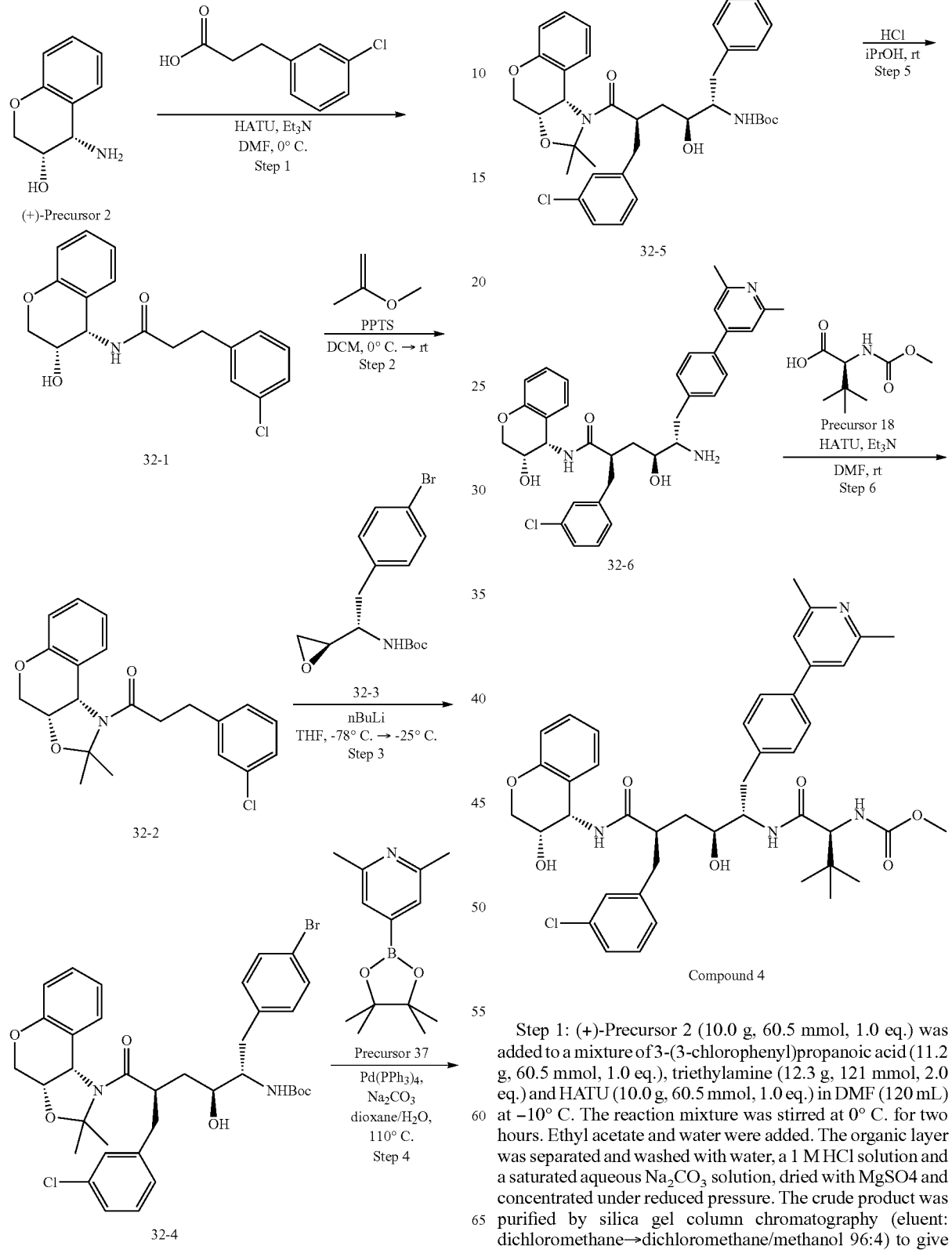

Step 1: (+)-Precursor 2 (10.0 g, 60.5 mmol, 1.0 eq.) was added to a mixture of 3-(3-chlorophenyl)propanoic acid (11.2 g, 60.5 mmol, 1.0 eq.), triethylamine (12.3 g, 121 mmol, 2.0 eq.) and HATU (10.0 g, 60.5 mmol, 1.0 eq.) in DMF (120 mL) at −10° C. The reaction mixture was stirred at 0° C. for two hours. Ethyl acetate and water were added. The organic layer was separated and washed with water, a 1 M HCl solution and a saturated aqueous Na₂CO₃ solution, dried with MgSO4 and concentrated under reduced pressure. The crude product was purified by silica gel column chromatography (eluent: dichloromethane→dichloromethane/methanol 96:4) to give 15.8 g (79%) of Intermediate 32-1.

Step 2: 2-Methoxypropene (34.3 g, 476 mmol, 10.0 eq.) was dropwise added over a period of 30 minutes to a solution of intermediate 32-1 (15.8 g, 47.6 mmol, 1.0 eq.) and pyridinium p-toluenesulfonate (PPTS, 1.2 g, 4.8 mmol, 0.1 eq.) in dichloromethane at 0° C. The reaction mixture was stirred at room temperature for 24 hours. Ethyl acetate and water were added. The organic layer was separated, washed with water, a 1 M HCl solution and a saturated aqueous $Na_2CO_3$ solution, dried with $MgSO_4$ and concentrated under reduced pressure. The crude product was purified by silica gel column chromatography (eluent: heptane/ethyl acetate 80:20→40:60) to give 10.1 g (57%) of Intermediate 32-2.

Step 3: n-Butyllithium (17.4 mL of a 2.5 M solution in hexane, 43.6 mmol, 2.05 eq.) was dropwise added to a solution of Intermediate 32-2 (7.9 g, 21.2 mmol, 1.0 eq.) and epoxide 32-3 ([CAS No.: 1003871-37-1]; 7.2 g, 21.2 mmol, 1.0 eq.) in THF (200 mL) at −78° C. The reaction mixture was stirred at −25° C. for two hours. Water was dropwise added, followed by the addition of ethyl acetate. The organic layer was separated, dried with $MgSO_4$ and concentrated under reduced pressure. The crude product was purified by silica gel column chromatography (eluent: heptane/ethyl acetate 12:88→40:60) to give 5.0 g (33%) of Intermediate 32-4.

The latter was converted to Compound 4 using the procedures of Step 5, Step 6 and Step 7 as described in Example 17.

Example 33

Synthesis of Compound 5

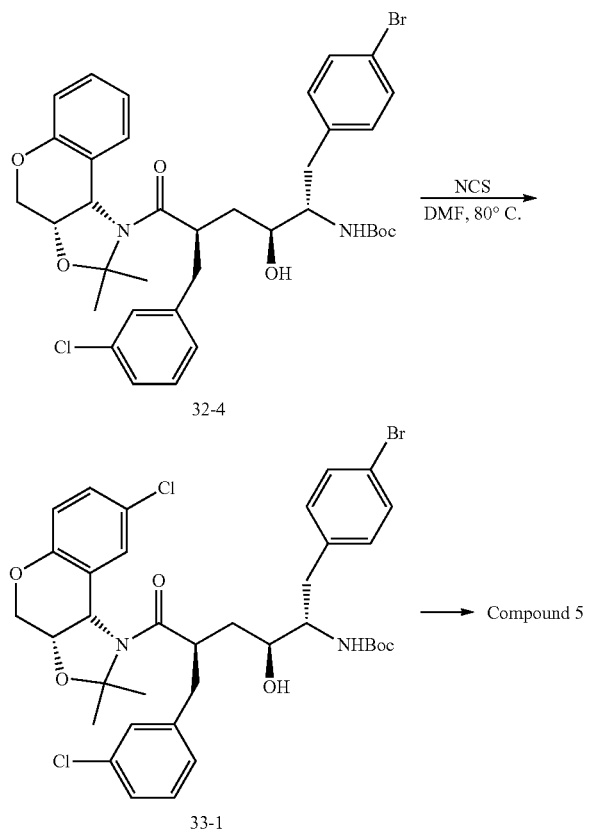

A solution of Intermediate 32-4 (3.6 g, 5.0 mmol, 1.0 eq.) and N-chlorosuccinimide (NCS; 806 mg, 6.0 mmol, 1.2 eq.) in DMF was stirred at 80° C. until no more starting material was left. After the reaction mixture was allowed to cool to room temperature, water was added. The water phase was extracted with ethyl acetate, the combined organic phases were washed with a 1 M NaOH solution, dried with $MgSO_4$ and concentrated under reduced pressure. The residue was purified by silica gel column chromatography (eluent: dichloromethane→dichloromethane/methanol 97.5:2.5) to give 3.1 g (82%) of Intermediate 33-1. The latter was converted to Compound 5 using respectively the procedures as described for Step 4, Step 5 and Step 6 in Example 32.

Compound 6 was prepared similarly to Compound 5, but using a Stille cross-coupling reaction as described in Example 23 and a TFA mediated deprotection step as described in Example 27, Step 2.

Example 34

Synthesis of Compound 1

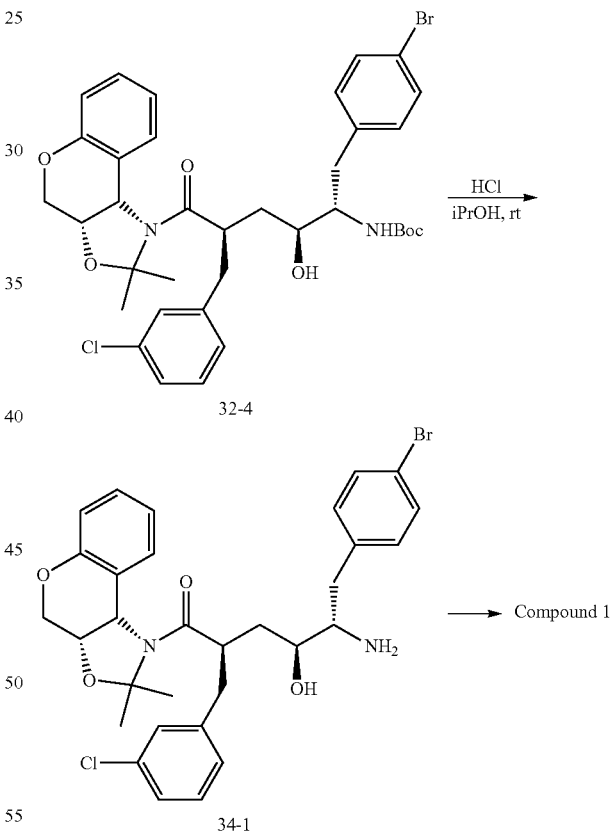

Intermediate 32-4 was treated with HCl using the procedure as described for Step 6 in Example 17. The crude reaction product was purified by silica gel column chromatography (eluent: dichloromethane→dichloromethane/methanol 93:7) to give Intermediate 34-1 (42%). The latter was converted to Compound 1 using the procedures from Step 2 and Step 3 as described in Example 21.

Compounds 2 and 3 were prepared analogously to Compound 1.

Example 35

Synthesis of Compound 79

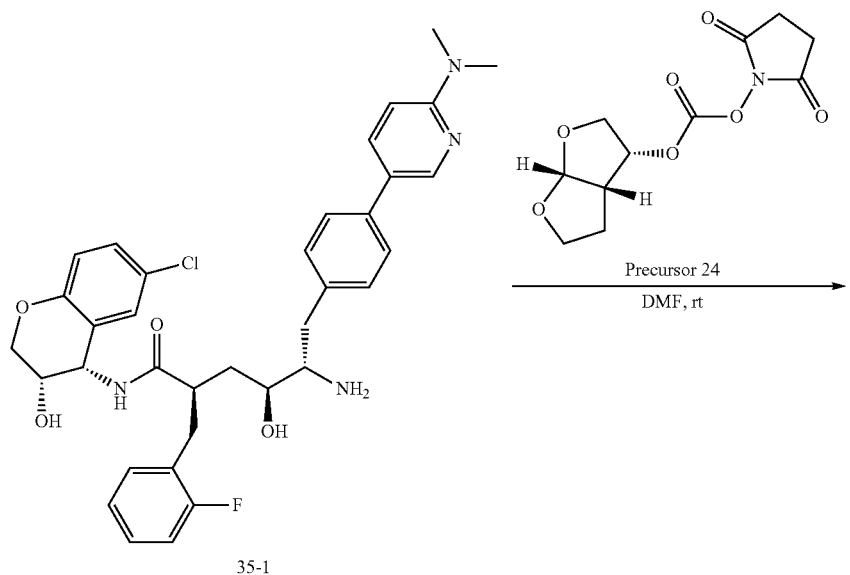

35-1

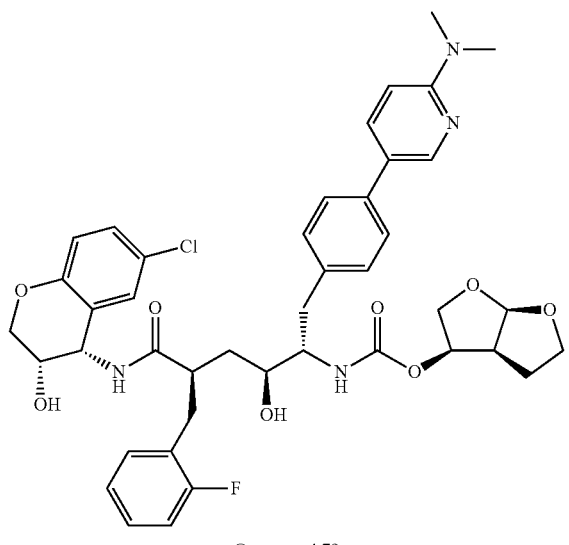

Compound 79

Amine 35-1 was prepared using the procedures as exemplified for the preparation of Intermediate 28-3. A solution of Intermediate 35-1 (250 mg, 0.39 mmol, 1.0 eq.) and Precursor 24 (150 mg, 0.55 mmol, 1.4 eq.) in DMF (4 mL) was stirred for one hour at room temperature. Water and a saturated aqueous $Na_2CO_3$ solution were added to the reaction mixture, the precipitate was filtered off and washed with water. The crude product was suspended in boiling acetonitrile and subsequently allowed to cool to room temperature, 236 mg (73%) of Compound 79 was obtained as a white powder.

Compound 81 was prepared analogously to Compound 79. Compound 68 was prepared analogously to Compound 79, but starting from amine 18-4. In case of Compounds 70, 71, 72, 73 and 76 the appropriate amine was prepared according to the synthesis of Intermediate 19-2 as described in Example 19. In case of Compounds 74, 74, 76, 77 and 81 the appropriate amine was prepared according to the synthesis of Intermediate 26-6 as described in Example 26. In case of Compound 69 the appropriate amine (hydrochloride salt) was prepared as described in Example 29.

Example 36
Synthesis of Compound 57
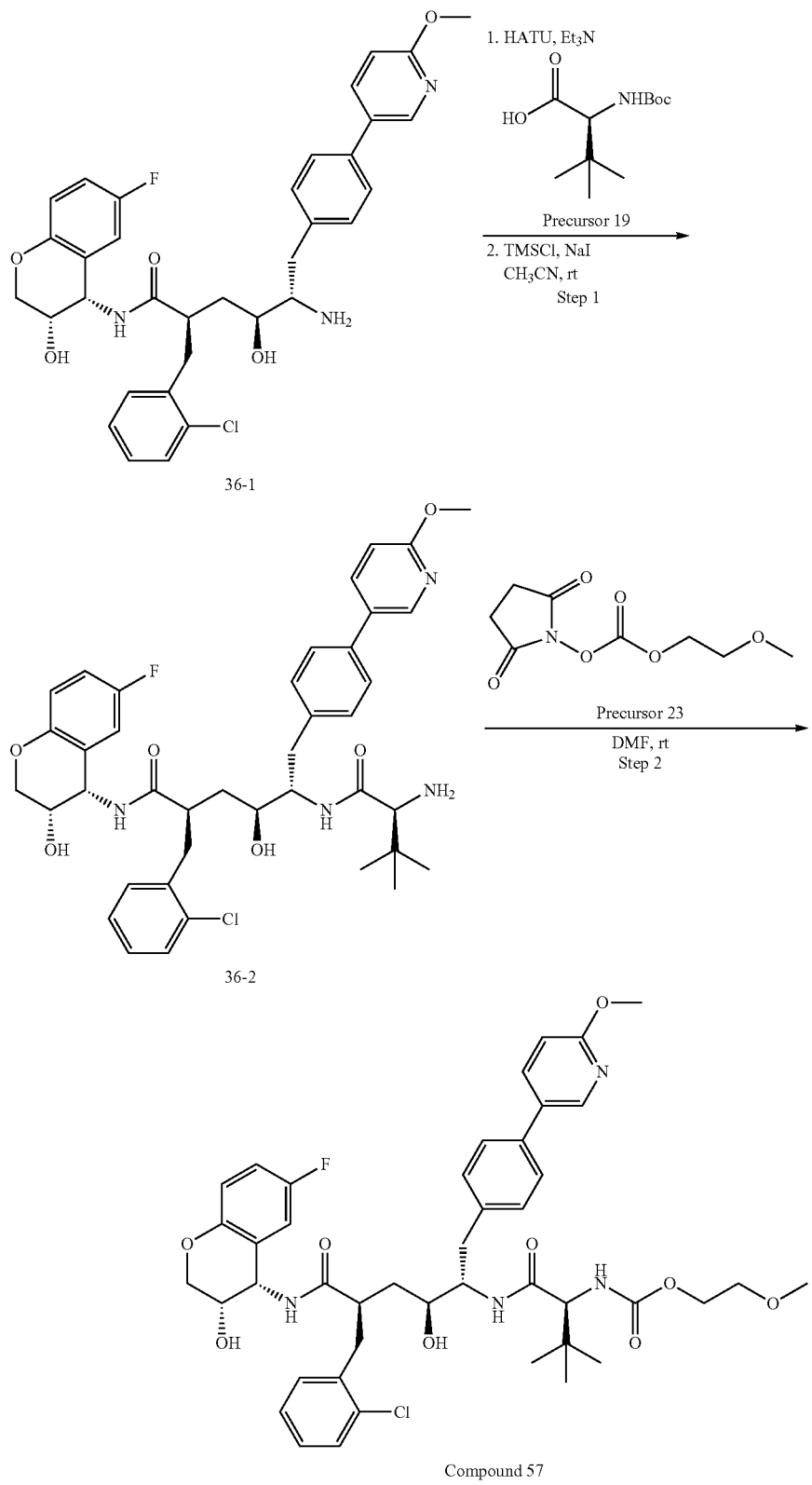 [SMILES: COc1ccc(-c2ccc(C[C@H](N)[C@@H](O)C[C@@H](Cc3ccccc3Cl)C(=O)N[C@H]3c4cc(F)ccc4OC[C@H]3O)cc2)cn1 ; CC(C)(C)OC(=O)N[C@H](C(=O)O)C(C)(C)C ; COc1ccc(-c2ccc(C[C@H](NC(=O)[C@@H](N)C(C)(C)C)[C@@H](O)C[C@@H](Cc3ccccc3Cl)C(=O)N[C@H]3c4cc(F)ccc4OC[C@H]3O)cc2)cn1 ; COCCOC(=O)ON1C(=O)CCC1=O ; COCCOC(=O)N[C@H](C(=O)N[C@@H](Cc1ccc(-c2ccc(OC)nc2)cc1)[C@@H](O)C[C@@H](Cc1ccccc1Cl)C(=O)N[C@H]1c2cc(F)ccc2OC[C@H]1O)C(C)(C)C]

Amine 36-1 was prepared using the procedures as exemplified for the preparation of Intermediate 26-6.

Step 1: Amine 36-1 (164 mg, 0.26 mmol, 1.0 eq.) and Precursor 19 (67 mg, 0.29 mmol, 1.1 eq.) were dissolved in acetonitrile (15 mL). Triethylamine (55 µL, 0.40 mmol, 1.5 eq.) and HATU (111 mg, 0.29 mmol, 1.1 eq.) were successively added. The reaction mixture was stirred for 30 minutes at room temperature. NaI (436 mg, 2.91 mmol, 11.0 eq.) and TMSCl (287 mg, 2.65 mmol, 10.0 eq.) were added and stirring was continued for one hour. Methanol (10 mL) and an aqueous NaOH solution (10 mL of 1 M NaOH solution, 10.0 mmol, 38.0 eq.) were added, the reaction mixture was stirred for an additional 30 minutes. An excess of water was added, the precipitate was filtered off, washed with water and dried under high vacuum to give 149 mg (69%) of crude Intermediate 36-2.

Step 2: A solution of Intermediate 36-2 (149 mg, 0.20 mmol, 1.0 eq.), Precursor 23 (66 mg, 0.31 mmol, 1.5 eq.) and triethylamine (41 mg, 0.41 mmol, 2.0 eq.) in DMF (15 mL) was stirred at room temperature for one hour. Water and a saturated aqueous $Na_2CO_3$ solution were added to the reaction mixture, the precipitate was filtered off and washed with water. After purification by silica gel column chromatography (eluent: dichloromethane→dichloromethane/methanol 96:4) 62 mg (36%) of Compound 57 was obtained.

Compound 55 was prepared analogously to Compound 57. Compound 34 was prepared analogously to Compound 57 but starting from amine 18-4.

Example 37

Synthesis of Compound 97

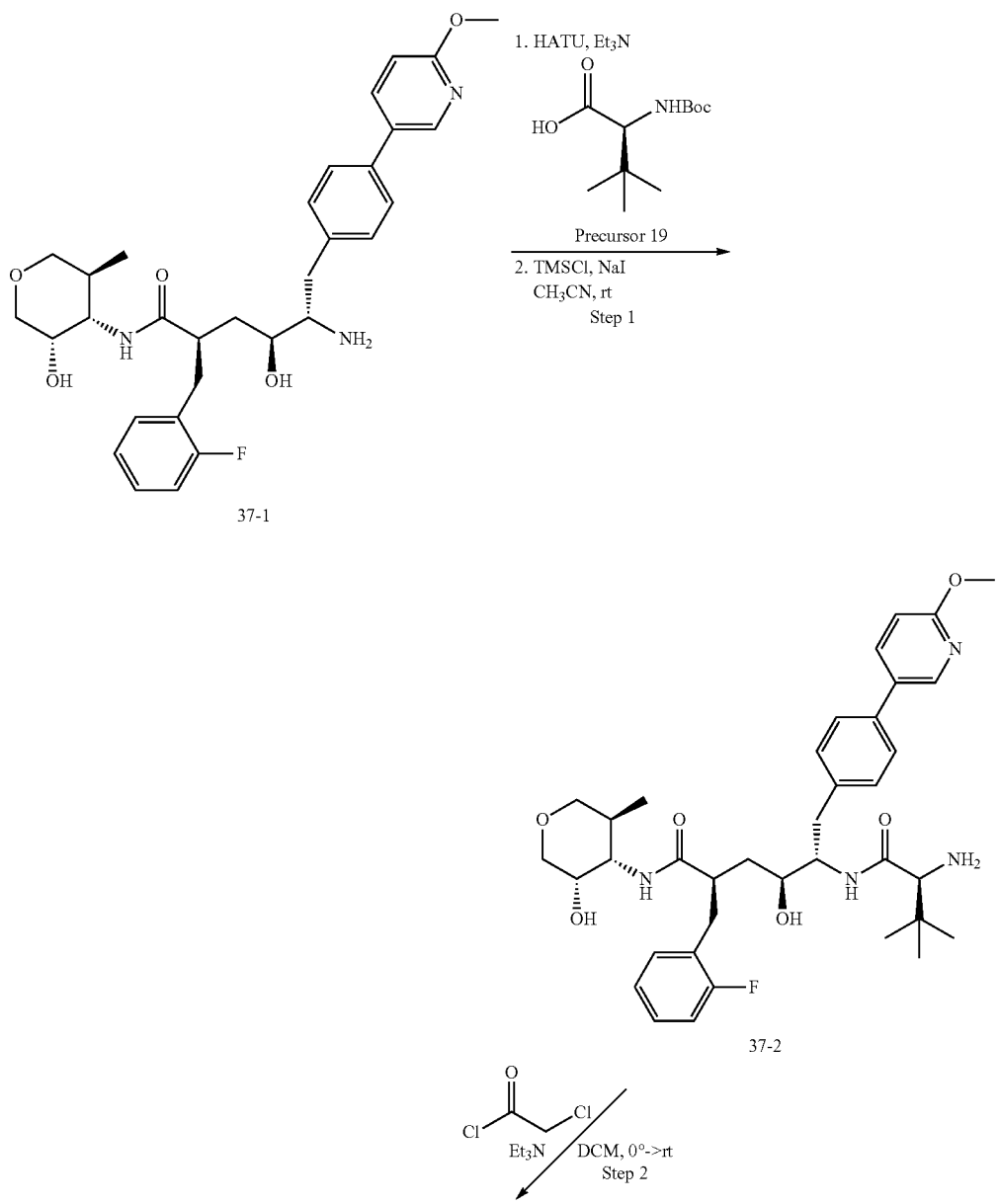

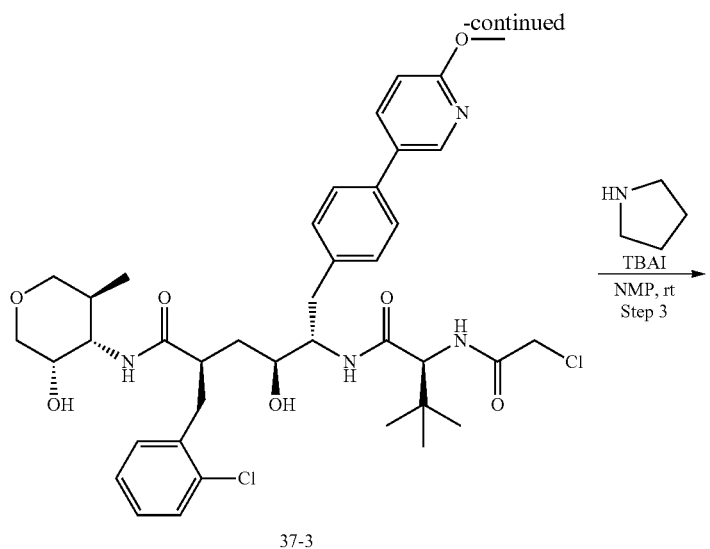
37-3

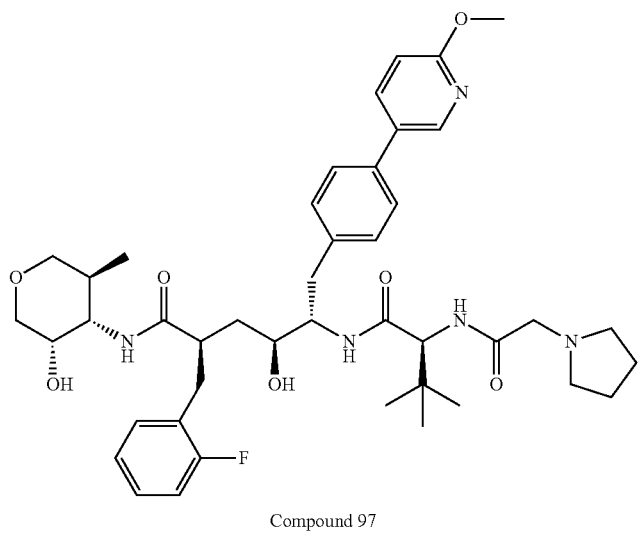 [SMILES: COc1ccc(-c2ccc(C[C@H](NC(=O)[C@@H](NC(=O)CN3CCCC3)C(C)(C)C)[C@@H](O)C[C@@H](Cc3ccccc3F)C(=O)N[C@H]3[C@H](C)COC[C@H]3O)cc2)cn1]
Compound 97

Intermediate 37-1 was prepared analogously to Intermediate 26-5 as exemplified in Example 26.

Step 1: Intermediate 37-1 was converted to Intermediate 37-2 using the procedure as described for Step 1 in Example 36.

Step 2: A solution of Intermediate 37-2 (287 mg, 0.43 mmol, 1.0 eq.) in dichloromethane (4 mL) was slowly added to a mixture of chloroacetyl chloride (73 mg, 0.65 mmol, 1.5 eq.) and triethylamine (0.18 mL, 1.30 mmol, 3.0 eq.) in dichloromethane (4 mL) at 0° C. The reaction mixture was stirred at room temperature until complete conversion and then washed with a saturated aqueous NH$_4$Cl solution, dried with anhydrous MgSO$_4$ and concentrated under reduced pressure to give 240 mg (77%) of crude Intermediate 37-3.

Step 3: A mixture of Intermediate 37-3 (240 mg, 0.33 mmol, 1.0 eq.), pyrrolidine (0.286 mL, 3.25 mmol, 10 eq.) and tetrabutylammonium iodide (TBAI; 12 mg, 0.03 mmol, 0.1 eq.) in N-methylpyrrolidinone (NMP; 3 mL) was stirred at room temperature until complete conversion. Water was added to the reaction mixture, the precipitate was filtered off, washed with water and dried under high vacuum. The crude product was purified by silica gel column chromatography (eluent: dichloromethane→dichloromethane/methanol 95:5) to give 216 mg (85%) of Compound 97.

Example 38

Synthesis of Compound 9

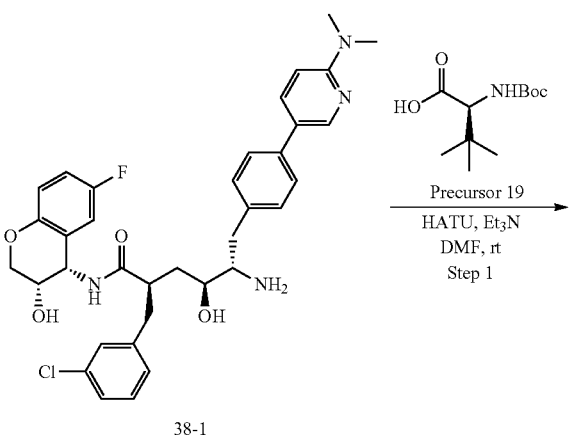
38-1

-continued

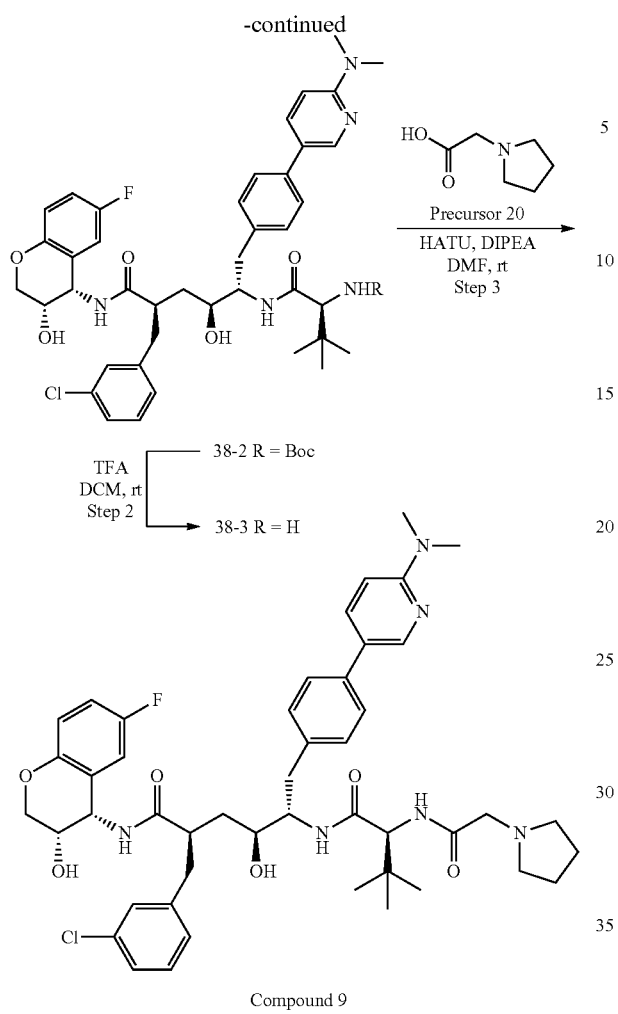

Compound 9

Intermediate 38-1 was prepared analogously to Intermediate 17-6 with Step 6 involving a TFA mediated Boc-deprotection step as described for Step 2 in Example 27.

Step 1: Intermediate 38-1 (610 mg, 0.96 mmol, 1.0 eq.) and Precursor 19 (223 mg, 0.96 mmol, 1.0 eq.) were dissolved in DMF (4 mL). DIPEA (374 mg, 2.89 mmol, 3.0 eq.) and HATU (385 mg, 1.01 mmol, 1.05 eq.) were successively added. The reaction mixture was stirred for 30 minutes at room temperature. A saturated aqueous $Na_2CO_3$ solution was added, the water phase was extracted with ethyl acetate. The combined organic phases were washed with brine, dried with $MgSO_4$ and concentrated under reduced pressure. The crude product was purified by silica gel column chromatography (eluent: dichloromethane→dichloromethane/methanol 93:7) to give 207 mg (25%) of Intermediate 38-2.

Step 2: Intermediate 38-2 was converted to Intermediate 38-3 according to the TFA mediated Boc-deprotection procedure as described for Step 2 in Example 27.

Step 3: DIPEA (74 mg, 0.57 mmol, 3.0 eq.) and HATU (76 mg, 0.20 mmol, 1.05 eq.) were successively added to a solution of Intermediate 38-3 (142 mg, 0.19 mmol, 1.0 eq.) and Precursor 20 (25 mg, 0.19 mmol, 1.0 eq.) in DMF (3 mL). The reaction mixture was stirred for 30 minutes at room temperature. A saturated aqueous $Na_2CO_3$ solution was added, the water phase was extracted with ethyl acetate. The combined organic phases were washed with brine and concentrated under reduced pressure. The crude product was purified by preparative HPLC to give 45 mg (26% over two steps) of Compound 9.

Compound 19 was synthesized starting from Intermediate 35-1 using the reaction sequence as exemplified for Example 38, but Step 2 involving a HCl mediated Boc-deprotection step as described in Example 17, Step 6.

Example 39

Synthesis of Compound 53

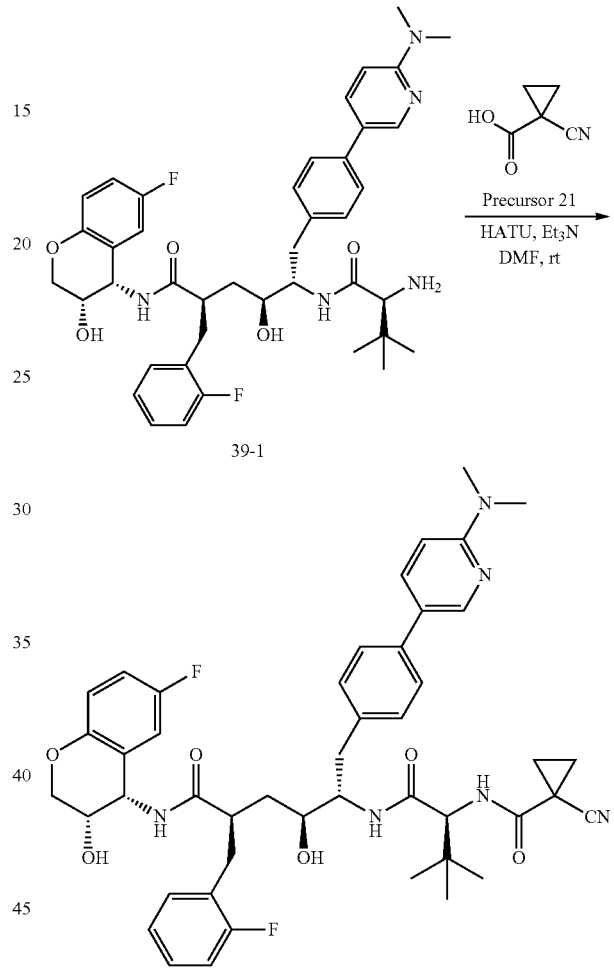

Compound 53

Amine 39-1 was prepared starting from Intermediate 18-4 using the procedure as described for Step 1 in Example 36. Intermediate 39-1 (210 mg, 0.29 mmol, 1.0 eq.) and Precursor 21 (32 mg, 0.29 mmol, 1.0 eq.) were dissolved in DMF (10 mL). Triethylamine (58 mg, 0.58 mmol, 2.0 eq.) and HATU (115 mg, 0.30 mmol, 1.05 eq.) were successively added. The reaction mixture was stirred for one hour at room temperature. A saturated aqueous $Na_2CO_3$ solution was added, the precipitate was filtered off, washed with water and dried under high vacuum. The crude product was purified by silica gel column chromatography (eluent: dichloromethane→dichloromethane/methanol 97:3) to give 143 mg (59%) of Compound 53.

In case of Compound 47 the amine used for amide coupling was prepared via a synthesis sequence analogously to the one as described for the preparation of Intermediate 38-3, but in which Boc-deprotection was carried out according to the procedure as described in Example 19.

TABLE 1

| Comp. Nº | R¹ | R⁶ | R⁵ | R³ | R⁴ |
|---|---|---|---|---|---|
| 1 | m-Cl | H | H | OCH₃ | 2-methylpyridin-4-yl |
| 2 | m-Cl | H | H | OCH₃ | 6-(dimethylamino)pyridin-3-yl |
| 3 | m-Cl | H | H | OCH₃ | 6-methoxypyridin-3-yl |
| 4 | m-Cl | H | H | OCH₃ | 2,6-dimethylpyridin-4-yl |
| 5 | m-Cl | Cl | H | OCH₃ | 6-(dimethylamino)pyridin-3-yl |
| 6 | m-Cl | Cl | H | OCH₃ | 2-methylthiazol-5-yl |
| 7 | o-F | H | H | OCH₃ | 6-(dimethylamino)pyridin-3-yl |
| 8 | o-F | Cl | H | OCH₃ | 6-(dimethylamino)pyridin-3-yl |

TABLE 1-continued
| # | | | | | |
|---|---|---|---|---|---|
| 9 | m-Cl | F | H | 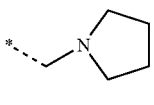 | 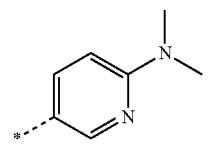 |
| 10 | o-F | F | F | OCH₃ | 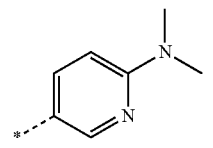 |
| 11 | o-F | Cl | H | OCH₃ | 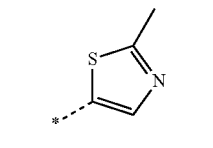 |
| 12 | o-F | Cl | H | OCH₃ | 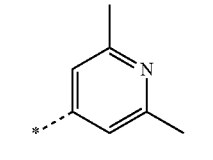 |
| 13 | m-Cl | F | H | OCH₃ | 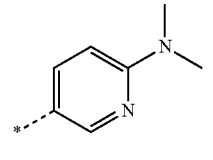 |
| 14 | o-F | Cl | H | OCH₃ | 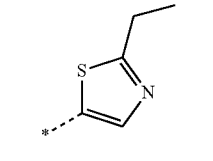 |
| 15 | m-O—CH₃ | H | H | OCH₃ | 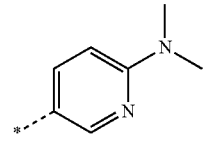 |
| 16 | o-F | H | H | OCH₃ | 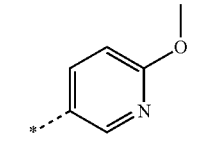 |
| 17 | m-O—CH₃ | H | H | OCH₃ | 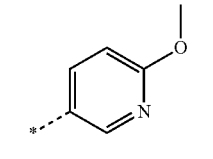 |
| 18 | o-F | Cl | H | OCH₃ | 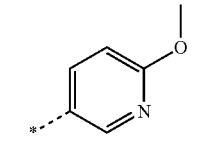 |
| 19 | o-F | Cl | H | 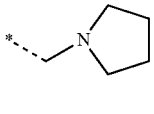 | 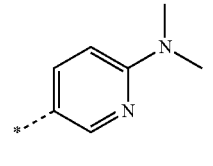 |

TABLE 1-continued

| 20 | o-F | Cl | H | OCH₃ | (2-dimethylamino-thiazol-4-yl) |
| 21 | o-F | Cl | H | OCH₃ | (2-cyclopropyl-6-methyl-pyridin-4-yl) |
| 22 | o-F | Cl | H | OCH₃ | (5-dimethylamino-pyrazin-2-yl) |
| 23 | o-F | Cl | H | OCH₃ | (5-methoxy-pyrazin-2-yl) |
| 24 | o-F | Cl | H | OCH₃ | (6-methoxy-pyrazin-2-yl) |
| 25 | o-F | Cl | H | OCH₃ | (6-dimethylamino-pyrazin-2-yl) |
| 26 | m-O—CH₃ | F | H | OCH₃ | (6-dimethylamino-pyridin-3-yl) |
| 27 | m-O—CH₃ | Cl | H | OCH₃ | (6-methoxy-pyridin-3-yl) |
| 28 | o-F | Cl | H | OCH₃ | (2-cyclopropyl-thiazol-5-yl) |
| 29 | o-F | Cl | H | OCH₃ | (2-methoxy-thiazol-4-yl) |

TABLE 1-continued
| 30 | o-F | Cl | H | OCH₃ | 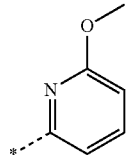 |
| 31 | o-F | Cl | H | OCH₃ | 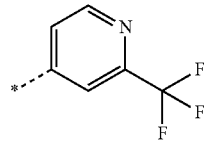 |
| 32 | o-F | Cl | H | OCH₃ | 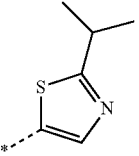 |
| 33 | o-F | F | H | OCH₃ | 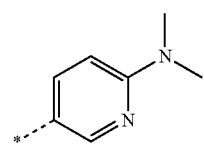 |
| 34 | o-F | F | H | O—(CH₂)₂OCH₃ | 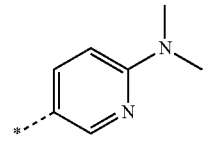 |
| 35 | o-F | F | H |  | 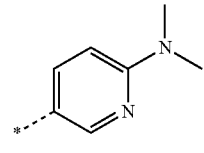 |
| 36 | m-F | H | H | OCH₃ | 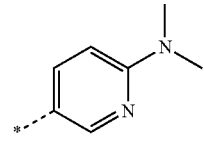 |
| 37 | o-Cl | H | H | OCH₃ | 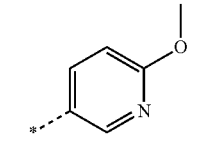 |
| 38 | o-F | H | H | OCH₃ | 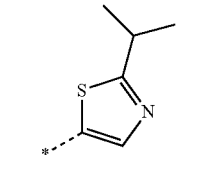 |
| 39 | m-F | Cl | H | OCH₃ | 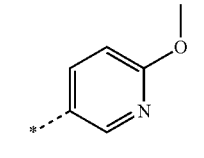 |

TABLE 1-continued
| | | | | | |
|---|---|---|---|---|---|
| 40 | m-F | H | F | OCH₃ | 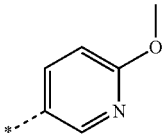 |
| 41 | m-O—CF₃ | H | H | OCH₃ | 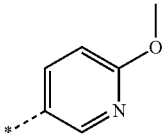 |
| 42 | m-O—CF₃ | Cl | H | OCH₃ | 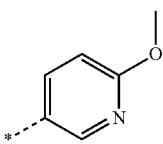 |
| 43 | o-F | Cl | H | OCH₃ | 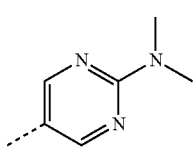 |
| 44 | o-F | Cl | H | OCH₃ | 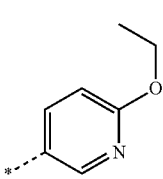 |
| 45 | o-F | H | Cl | OCH₃ | 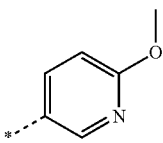 |
| 46 | m-F | Cl | H | OCH₃ | 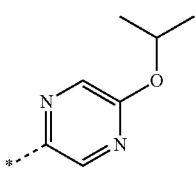 |
| 47 | o-F | Cl | H | 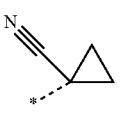 | 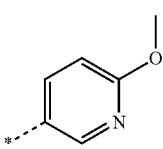 |
| 48 | o-F | Cl | H | OCH₃ | 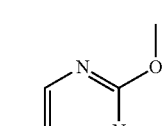 |
| 49 | m-O—CF₃ | Cl | H | OCH₃ | 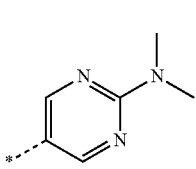 |

TABLE 1-continued
| | | | | | |
|---|---|---|---|---|---|
| 50 | o-F | H | F | OCH₃ | 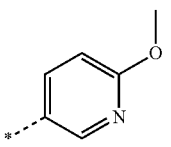 |
| 51 | o-F | H | F | OCH₃ | 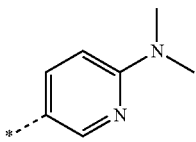 |
| 52 | o-F | F | Cl | OCH₃ | 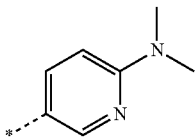 |
| 53 | o-F | F | H | 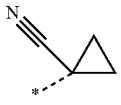 | 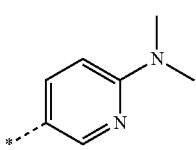 |
| 54 | o-F | H | Cl | OCH₃ | 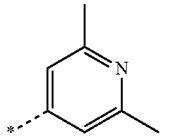 |
| 55 | o-F | Cl | H | —O(CH₂)₂OCH₃ | 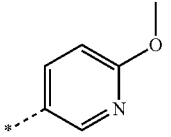 |
| 56 | o-F | F | Cl | OCH₃ | 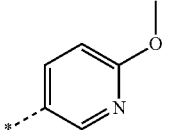 |
| 57 | o-Cl | F | H | —O(CH₂)₂OCH₃ | 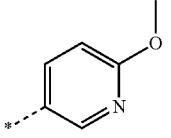 |
| 58 | o-Cl | Cl | H | OCH₃ | 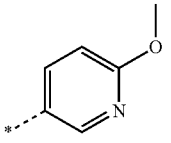 |
| 59 | o-F | F | H | OCH₃ | 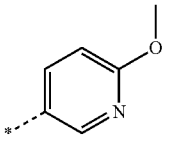 |
| 60 | o-F | Cl | F | OCH₃ | 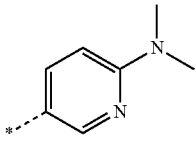 |

TABLE 1-continued
| | | | | | |
|---|---|---|---|---|---|
| 61 | o-F | Cl | F | OCH₃ | 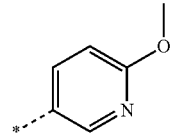 |
| 62 | m-F | F | H | OCH₃ | 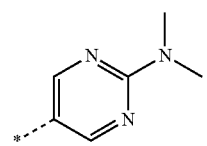 |
| 63 | o-Cl | F | H | OCH₃ | 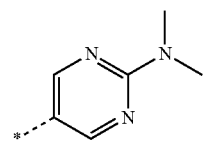 |
| 64 | m-O—CF₃ | F | H | OCH₃ | 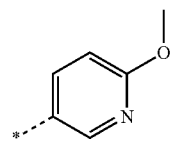 |
| 65 | m-F | F | H | OCH₃ | 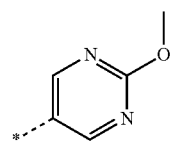 |
| 66 | o-F | CH₃ | H | OCH₃ | 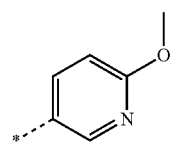 |
| 67 | o-Cl | F | H | OCH₃ | 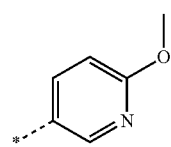 |

TABLE 1-continued

| Comp. N° | R¹ | R² | R⁴ |
|---|---|---|---|
| 68 | o-F | 6-fluoro-4-methyl-chroman-3-ol | 6-(dimethylamino)pyridin-3-yl |
| 69 | o-F | N-methyl-3,3-dimethyl-2-butanamide | 6-(dimethylamino)pyridin-3-yl |
| 70 | m-O—CH₃ | 6-chloro-4-methyl-chroman-3-ol | 6-methoxypyridin-3-yl |
| 71 | m-O—CH₃ | 6-chloro-4-methyl-chroman-3-ol | 2-(dimethylamino)thiazol-4-yl |
| 72 | o-F | 6-chloro-4-methyl-chroman-3-ol | 6-methoxypyridin-3-yl |
| 73 | m-O—CF₃ | 6-chloro-4-methyl-chroman-3-ol | 6-methoxypyridin-3-yl |
| 74 | o-F | 4-methyl-4,5,6,7-tetrahydrobenzothiophen-5-ol | 6-methoxypyridin-3-yl |

TABLE 1-continued
| | | | |
|---|---|---|---|
| 75 | o-F | 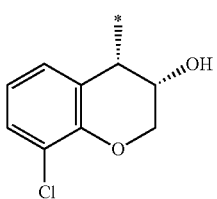 [SMILES: *[C@H]1c2cccc(Cl)c2OC[C@H]1O] | 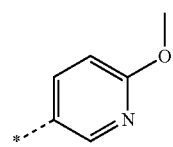 |
| 76 | o-F | 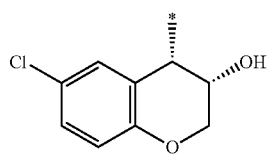 [SMILES: *[C@H]1c2cc(Cl)ccc2OC[C@H]1O] | 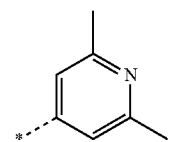 |
| 77 | o-Cl | 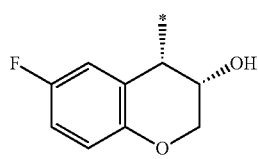 | 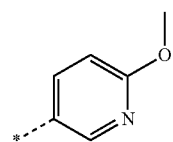 |
| 78 | o-Cl | 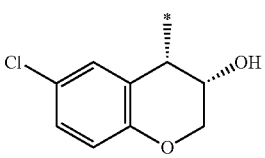 [SMILES: *[C@H]1c2cc(Cl)ccc2OC[C@H]1O] | 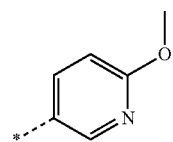 |
| 79 | o-F | 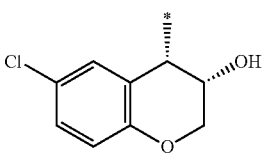 [SMILES: *[C@H]1c2cc(Cl)ccc2OC[C@H]1O] | 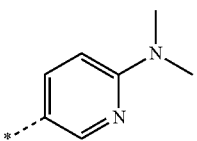 |
| 80 | o-F | 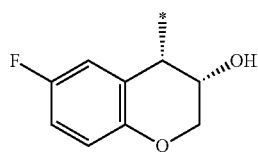 [SMILES: *[C@H]1c2cc(F)ccc2OC[C@H]1O] | 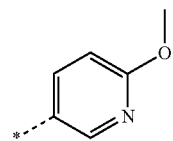 |
| 81 | o-F | 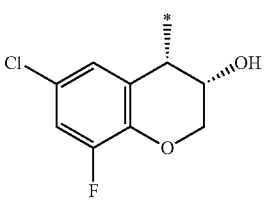 [SMILES: *[C@H]1c2cc(Cl)cc(F)c2OC[C@H]1O] | 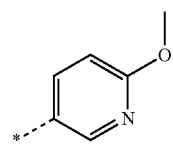 |
| 82 | o-F | 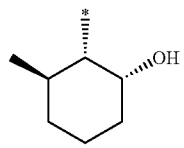 | 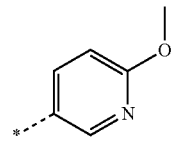 |

TABLE 1-continued
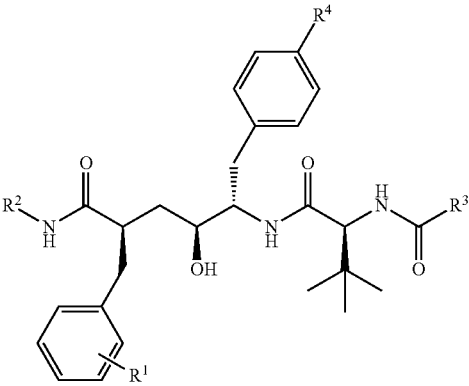
| Comp. N° | R¹ | R² | R³ | R⁴ |
|---|---|---|---|---|
| 83 | o-F | 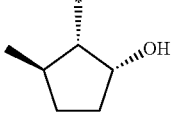 | OCH₃ | 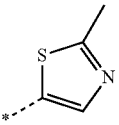 |
| 84 | o-F | 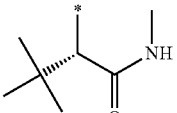 | OCH₃ | 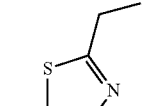 |
| 85 | m-F | 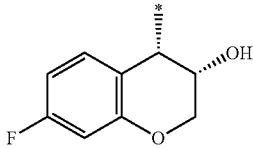 | OCH₃ | 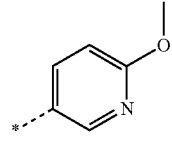 |
| 86 | o-F | 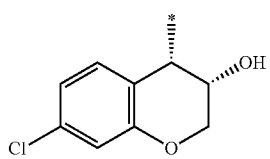 | OCH₃ | 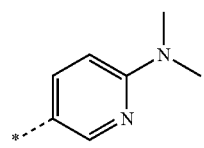 |

TABLE 1-continued

| Comp. N° | R¹ | R² | R³ | R⁴ᵃ |
|---|---|---|---|---|
| 87 | o-F | (2-methyl-cyclopentanol) | OCH₃ | —N(CH₃)₂ |
| 88 | o-F | (tert-butyl-N-methyl amide) | OCH₃ | OCH₃ |
| 89 | o-F | (2-methyl-cyclohexanol) | OCH₃ | —N(CH₃)₂ |
| 90 | o-F | (tert-butyl-N-methyl amide) | OCH₃ | —N(CH₃)₂ |
| 91 | o-Cl | (2-methyl-cyclohexanol) | OCH₃ | OCH₃ |
| 92 | m-F | (tert-butyl-N-(2-methoxyethyl) amide) | OCH₃ | OCH₃ |
| 93 | o-F | (4,5,6,7-tetrahydrobenzothiophen-5-ol) | OCH₃ | OCH₃ |

TABLE 1-continued

| | | | | |
|---|---|---|---|---|
| 94 | m-O—CF$_3$ | (trans-2-methylcyclohexan-1-ol) | OCH$_3$ | OCH$_3$ |
| 95 | o-Cl | (4-methyl-4,5,6,7-tetrahydrobenzothiophen-5-ol) | OCH$_3$ | OCH$_3$ |
| 96 | o-F | (trans-2-methylcyclohexan-1-ol) | OCH$_3$ | OCH$_3$ |
| 97 | o-F | (trans-2-methylcyclohexan-1-ol) | (pyrrolidinylmethyl) | OCH$_3$ |
| 98 | o-Cl | (N-(2-methoxyethyl)-3,3-dimethylbutanamide) | OCH$_3$ | OCH$_3$ |
| 99 | o-F | (trans-2-methylcyclopentan-1-ol) | OCH$_3$ | OCH$_3$ |
| 100 | o-F | (2-methylcyclohexan-1-ol) | OCH$_3$ | OCH$_3$ |
| 101 | o-F | (6-methyl-8-fluorochroman-3-ol) | OCH3 | OCH3 |
| 102 | o-F | (6-fluoro-8-methylchroman-3-ol) | OCH3 | OCH3 |

Retention time ($R_t$) are given in minutes and were determined via Reversed phase HPLC (Ultra Performance Liquid Chromatography) on a BEH C18 column (1.7 μm, 2.1×50 mm, Waters Acquity) with a flow rate of 0.7 ml/min and column temperature of 70° C. Two mobile phases (mobile phase A: MeOH; mobile phase B: 10 mM NH$_4$OAc in 90% H$_2$O and 10% CH$_3$CN) were used to run a gradient condition starting from 5% A and 95% B to 95% A and 5% B in 1.3 minutes, hold for 0.2 minutes, then back to 5% A and 95% B in 0.2 minutes and finally hold these conditions for 0.3 minutes. An injection volume of 0.75 μl was used.

Melting points (m.p.) were determined with a DSC1 STAR$^e$ (Mettler-Toledo). Melting points were measured with a temperature gradient of 10° C./min. The starting temperature was 30° C., the maximum temperature 300° C. Values are peak values.

TABLE 2

Retention time ($R_t$) are given in minutes and were determined via Reversed phase UPLC (Ultra Performance Liquid Chromatography) on a BEH C18 column (1.7 μm, 2.1 × 50 mm. Waters Acquity) with a flow rate of 0.7 ml/min and column temperature of 70° C. Two mobile phases (mobile phase A: MeOH; mobile phase B: 10 mM NH$_4$OAc in 90% H$_2$O and 10% CH$_3$CN) were used to run a gradient condition starting from 5% A and 95% B to 95% A and 5% B in 1.3 minutes, hold for 0.2 minutes, then back to 5% A and 95% B in 0.2 minutes and finally hold these conditions for 0.3 minutes. An injection volume of 0.75 μl was used. Melting points (m.p.) were determined with a DSC1 STAR$^e$ (Mettler-Toledo). Melting points were measured with a temperature gradient of 10° C./min. The starting temperature was 30° C., the maximum temperature 300° C. Values are peak values.

| Comp. N° | $R_t$ (min) | MW | m.p. (° C.) |
|---|---|---|---|
| 1 | 1.33 | 756.33 | |
| 2 | 1.41 | 786.36 | |
| 3 | 1.38 | 772.32 | |
| 4 | 1.36 | 770.35 | 229.07 |
| 5 | 1.44 | 819.32 | 239.39 |
| 6 | 1.40 | 796.25 | |
| 7 | 1.36 | 769.39 | 228.12 |
| 8 | 1.40 | 803.35 | 271.61 |
| 9 | 1.46 | 856.41 | |
| 10 | 1.37 | 805.37 | |
| 11 | 1.36 | 780.28 | 255.90 |
| 12 | 1.38 | 788.34 | 253.22 |
| 13 | 1.38 | 803.35 | 252.99 |
| 14 | 1.39 | 794.29 | |
| 15 | 1.35 | 781.41 | 214.14 |
| 16 | 1.35 | 756.35 | |
| 17 | 1.35 | 768.37 | 221.37 |
| 18 | 1.39 | 790.32 | |
| 19 | 1.43 | 856.41 | |
| 20 | 1.41 | 809.30 | |
| 21 | 1.43 | 814.35 | 237.24 |
| 22 | 1.36 | 804.34 | |
| 23 | 1.39 | 791.31 | |
| 24 | 1.38 | 791.31 | 240.69 |
| 25 | 1.37 | 804.34 | |
| 26 | 1.35 | 799.40 | |
| 27 | 1.38 | 802.34 | |
| 28 | 1.41 | 806.29 | 239.55 |
| 29 | 1.40 | 796.27 | |
| 30 | 1.42 | 790.32 | |
| 31 | 1.39 | 828.29 | |
| 32 | 1.43 | 808.31 | 236.06 |
| 33 | 1.36 | 787.38 | 258.20 |
| 34 | 1.33 | 831.40 | 244.49 |
| 35 | 1.39 | 822.39 | 238.80 |
| 36 | 1.39 | 769.39 | 226.05 |
| 37 | 1.41 | 772.32 | |
| 38 | 1.43 | 774.35 | |
| 39 | 1.43 | 790.32 | 243.66 |
| 40 | 1.36 | 774.34 | 222.56 |
| 41 | 1.43 | 822.35 | 228.45 |
| 42 | 1.47 | 856.31 | 237.32 |
| 43 | 1.41 | 804.34 | 271.32 |
| 44 | 1.46 | 804.33 | 265.19 |
| 45 | 1.38 | 790.32 | 235.74 |
| 46 | 1.47 | 819.34 | 244.40 |
| 47 | 1.39 | 825.33 | 226.41 |
| 48 | 1.33 | 791.31 | 246.19 |
| 49 | 1.46 | 870.33 | 256.86 |
| 50 | 1.32 | 774.34 | 219.44 |
| 51 | 1.35 | 787.38 | 207.05 |
| 52 | 1.40 | 821.34 | 255.44 |
| 53 | 1.33 | 822.39 | 239.87 |
| 54 | 1.34 | 788.34 | |
| 55 | 1.37 | 834.34 | 228.27 |
| 56 | 1.38 | 808.31 | |
| 57 | 1.36 | 834.34 | |
| 58 | 1.40 | 806.29 | |
| 59 | 1.33 | 774.34 | 254.86 |
| 60 | 1.42 | 821.34 | |
| 61 | 1.37 | 808.31 | 265.41 |
| 62 | 1.35 | 788.37 | 244.51 |
| 63 | 1.37 | 804.34 | |
| 64 | 1.41 | 840.34 | |
| 65 | 1.28 | 775.34 | |
| 66 | 1.42 | 770.37 | |
| 67 | 1.41 | 790.32 | |
| 68 | 1.33 | 772.33 | |
| 69 | 1.28 | 733.39 | |
| 70 | 1.35 | 787.29 | |
| 71 | 1.37 | 806.28 | 262.44 |
| 72 | 1.35 | 775.27 | 234.86 |
| 73 | 1.41 | 841.26 | |
| 74 | 1.29 | 745.28 | |
| 75 | 1.29 | 775.27 | 228.26 |
| 76 | 1.29 | 773.29 | 290.48 |
| 77 | 1.30 | 775.27 | 205.21 |
| 78 | 1.34 | 791.24 | |
| 79 | 1.32 | 788.30 | |
| 80 | 1.27 | 759.30 | 239.42 |
| 81 | 1.33 | 793.26 | 254.01 |
| 82 | 1.30 | 705.34 | |
| 83 | 1.31 | 696.34 | |
| 84 | 1.35 | 739.38 | |
| 85 | 1.39 | 774.34 | 215.00 |
| 86 | 1.38 | 803.35 | 237.42 |
| 87 | n.d. | n.d. | |
| 88 | 1.35 | 735.40 | |
| 89 | 1.37 | 733.42 | |
| 90 | 1.35 | 748.43 | |
| 91 | 1.39 | 736.36 | 215.60 |
| 92 | 1.39 | 779.43 | |
| 93 | 1.40 | 760.33 | 219.41 |
| 94 | 1.42 | 786.38 | |
| 95 | 1.39 | 776.30 | 234.17 |
| 96 | 1.35 | 720.39 | |
| 97 | 1.42 | 773.45 | 127.74 |
| 98 | 1.39 | 795.40 | |
| 99 | 1.38 | 706.37 | |
| 100 | 1.35 | 706.37 | |
| 101 | 1.38 | 788.36 | 254.88 |
| 102 | 1.39 | 788.36 | 236.58 |

(n.d. means not determined)

TABLE 3

| Comp. N° | ¹H NMR (δ ppm) |
|---|---|
| 1 | (400 MHz, DMSO-d$_6$) 0.80 (s, 9H) 1.34-1.43 (m, 1H) 1.64-1.73 (m, 1H) 2.50 (s, 3H) 2.56-2.63 (m, 1H) 2.69-2.74 (m, 1H) 2.80-2.97 (m, 3H) 3.49 (s, 3H) 3.55-3.62 (m, 1H) 3.72-3.77 (m, 1H) 3.89 (d, J = 10.4 Hz, 1H) 3.95 (br. s., 1H) 4.06 (dd, J = 11.5, 4.3 Hz, 1H) 4.13 (d, J = 11.5 Hz, 1H) 4.83 (d, J = 3.9 Hz, 1H) 5.07 (dd, J = 8.4, 3.7 Hz, 1H) 5.12 (d, J = 2.7 Hz, 1H) 6.71 (d, J = 8.0 Hz, 2H) 6.80 (t, J = 7.6 Hz, 1H) 7.00 (d, J = 7.2 Hz, 1H) 7.04-7.15 (m, 2H) 7.22-7.28 (m, 3H) 7.34 (d, J = 8.0 Hz, 2H) 7.41 (d, J = 5.3 Hz, 1H) 7.48 (s, 1H) 7.59 (d, J = 7.6 Hz, 2H) 7.66 (d, J = 8.6 Hz, 1H) 7.89 (d, J = 9.0 Hz, 1H) 8.45 (d, J = 5.3 Hz, 1H) |
| 6 | (400 MHz, DMSO-d$_6$) 0.76 (s, 9H) 1.33-1.42 (m, 1H) 1.59-1.70 (m, 1H) 2.54-2.61 (m, 1H) 2.64 (s, 3H) 2.69-2.80 (m, 2H) 2.85-3.05 (m, 2H) 3.50 (s, 3H) 3.58 (br. s., 1H) 3.76 (br. s., 1H) 3.87 (d, J = 10.2 Hz, 1H) 3.89-3.95 (m, 1H) 4.10 (d, J = 11.9 Hz, 1H) 4.15-4.22 (m, J = 11.3 Hz, 1H) 4.84 (d, J = 3.1 Hz, 1H) 5.09 (d, J = 6.8 Hz, 1H) 5.32 (br. s., 1H) 6.64 (d, J = 9.6 Hz, 1H) 6.76 (d, J = 8.6 Hz, 1H) 7.07 (br. s., 1H) 7.12 (d, J = 6.8 Hz, 1H) 7.15 (d, J = 8.6 Hz, 1H) 7.19-7.30 (m, 5H) 7.37 (d, J = 7.2 Hz, 2H) 7.61 (d, J = 10.0 Hz, 1H) 7.89 (s, 1H) 8.02 (d, J = 9.0 Hz, 1H) |
| 7 | (400 MHz, DMSO-d$_6$) 0.80 (s, 9H) 1.37-1.49 (m, 1H) 1.65-1.76 (m, 1H) 2.60-2.88 (m, 4H) 2.90-2.99 (m, 1H) 3.05 (s, 6H) 3.50 (s, 3H) 3.61 (br. s., 1H) 3.64-3.69 (m, 1H) 3.91 (d, J = 9.5 Hz, 1H) 3.94 (br. s., 1H) 4.00-4.07 (m, J = 11.8, 4.0 Hz, 1H) 4.11 (d, J = 11.3 Hz, 1H) 4.88 (d, J = 5.0 Hz, 1H) 5.06 (dd, J = 9.0, 3.8 Hz, 1H) 5.12 (d, J = 3.3 Hz, 1H) 6.70 (d, J = 8.5 Hz, 2H) 6.79 (t, J = 7.5 Hz, 1H) 6.76 (d, J = 8.3 Hz, 1H) 6.99 (d, J = 7.5 Hz, 1H) 7.03-7.14 (m, 3H) 7.20-7.29 (m, 2H) 7.25 (d, J = 8.0 Hz, 2H) 7.41 (d, J = 8.0 Hz, 2H) 7.65 (d, J = 8.0 Hz, 1H) 7.74 (dd, J = 8.8, 2.5 Hz, 1H) 7.79 (d, J = 9.3 Hz, 1H) 8.35 (d, J = 2.5 Hz, 1H) |
| 8 | (400 MHz, DMSO-d$_6$) 0.77 (s, 9H) 1.36-1.51 (m, 1H) 1.61-1.75 (m, 1H) 2.68-2.89 (m, 4H) 2.90-3.01 (m, 1H) 3.05 (s, 6H) 3.49 (s, 3H) 3.62 (br. s., 1H) 3.69 (br. s., 1H) 3.88 (d, J = 9.4 Hz, 1H) 3.91-4.01 (m, 1H) 4.08 (dd, J = 11.1, 3.5 Hz, 1H) 4.17 (d, J = 11.1 Hz, 1H) 4.89 (d, J = 3.7 Hz, 1H) 5.08 (dd, J = 7.4, 2.2 Hz, 1H) 5.29 (br. s., 1H) 6.69 (d, J = 8.8 Hz, 1H) 6.68 (d, J = 9.2 Hz, 1H) 6.76 (d, J = 8.6 Hz, 1H) 7.03-7.13 (m, 4H) 7.15 (d, J = 8.4 Hz, 1H) 7.19-7.28 (m, 4H) 7.37 (d, J = 7.6 Hz, 2H) 7.58 (d, J = 8.4 Hz, 0H) 7.72 (d, J = 8.8 Hz, 1H) 7.91 (d, J = 7.8 Hz, 1H) 8.33 (s, 1H) |
| 10 | (400 MHz, DMSO-d$_6$) 0.78 (s, 9H) 1.40-1.49 (m, 1H) 1.64-1.75 (m, 1H) 2.62-2.88 (m, 4H) 2.92-3.01 (m, 1H) 3.04 (s, 6H) 3.50 (s, 3H) 3.59 (br. s., 1H) 3.70 (br. s., 1H) 3.89 (d, J = 9.4 Hz, 1H) 3.92 (br. s., 1H) 4.15 (dd, J = 11.7, 2.9 Hz, 1H) 4.22 (d, J = 11.5 Hz, 1H) 4.88 (d, J = 4.7 Hz, 1H) 5.10 (dd, J = 8.0, 2.0 Hz, 1H) 5.33 (br. s., 1H) 6.69 (d, J = 8.4 Hz, 3H) 7.05-7.18 (m, 3H) 7.18-7.28 (m, 4H) 7.37 (d, J = 7.6 Hz, 2H) 7.64 (d, J = 8.8 Hz, 1H) 7.72 (dd, J = 8.9, 1.9 Hz, 1H) 7.92 (d, J = 8.8 Hz, 1H) 8.32 (s, 1H) |
| 16 | (400 MHz, DMSO-d$_6$) 0.80 (s, 9H) 1.35-1.49 (m, 1H) 1.63-1.78 (m, 1H) 2.67-2.77 (m, 2H) 2.76-2.88 (m, 2H) 2.88-3.02 (m, 1H) 3.49 (s, 3H) 3.61 (br. s., 1H) 3.67 (br. s., 1H) 3.88 (s, 3H) 3.91 (br. s., 1H) 3.96 (br. s., 1H) 4.04 (dd, J = 11.9, 4.1 Hz, 1H) 4.12 (d, J = 11.5 Hz, 1H) 4.89 (d, J = 4.5 Hz, 1H) 5.06 (dd, J = 7.7, 3.2 Hz, 1H) 5.13 (br. s., 1H) 6.69 (d, J = 8.2 Hz, 2H) 6.75 (d, J = 9.4 Hz, 1H) 6.78 (t, J = 7.4 Hz, 1H) 6.89 (d, J = 8.6 Hz, 1H) 6.99 (d, J = 7.2 Hz, 1H) 7.02-7.15 (m, 3H) 7.19-7.34 (m, 4H) 7.46 (d, J = 7.6 Hz, 2H) 7.66 (d, J = 8.8 Hz, 1H) 7.80 (d, J = 8.4 Hz, 1H) 7.92 (dd, J = 8.4, 2.5 Hz, 1H) 8.40 (d, J = 1.8 Hz, 1H) |
| 18 | (400 MHz, DMSO-d$_6$) 0.76 (s, 9H) 1.39-1.50 (m, 1H) 1.63-1.75 (m, 1H) 2.63-2.90 (m, 4H) 2.92-3.03 (m, 1H) 3.47 (s, 3H) 3.62 (br. s., 1H) 3.70 (br. s., 1H) 3.88 (s, 3H) 3.88 (d, J = 10.0 Hz, 1H) 3.92-4.02 (m, 1H) 4.08 (dd, J = 11.9, 3.5 Hz, 1H) 4.13-4.22 (m, J = 11.3 Hz, 2H) 4.90 (d, J = 5.1 Hz, 1H) 5.09 (dd, J = 8.6, 3.3 Hz, 1H) 5.29 (br. s., 1H) 6.69 (d, J = 9.6 Hz, 1H) 6.76 (d, J = 8.6 Hz, 1H) 6.88 (d, J = 8.6 Hz, 1H) 7.05-7.13 (m, 3H) 7.16 (dd, J = 8.6, 2.3 Hz, 1H) 7.21-7.30 (m, 4H) 7.43 (d, J = 7.8 Hz, 2H) 7.60 (d, J = 9.2 Hz, 1H) 7.91 (dd, J = 8.5, 1.9 Hz, 1H) 8.38 (d, J = 2.2 Hz, 1H) |
| 19 | (400 MHz, DMSO-d$_6$) 0.78 (s, 9H) 1.38-1.47 (m, 1H) 1.55-1.63 (m, 4H) 1.67-1.77 (m, 1H) 2.23-2.39 (m, 4H) 2.65-2.77 (m, 3H) 2.78-2.89 (m, 2H) 2.92-3.00 (m, 1H) 3.04 (s, 6H) 3.62 (br. s., 1H) 3.71 (br. s., 1H) 3.90-3.99 (m, 1H) 4.09 (dd, J = 11.9, 3.5 Hz, 1H) 4.18 (d, J = 11.9 Hz, 1H) 4.22 (d, J = 10.0 Hz, 1H) 4.86 (d, J = 4.7 Hz, 1H) 5.09 (dd, J = 9.0, 2.7 Hz, 1H) 5.30 (d, J = 3.1 Hz, 1H) 6.69 (d, J = 9.0 Hz, 1H) 6.76 (d, J = 8.8 Hz, 1H) 7.05-7.28 (m, 9H) 7.37 (d, J = 8.0 Hz, 2H) 7.73 (dd, J = 9.0, 2.0 Hz, 1H) 7.81 (d, J = 9.0 Hz, 1H) 7.91 (d, J = 8.4 Hz, 1H) 8.34 (d, J = 2.3 Hz, 1H) |
| 20 | (400 MHz, DMSO-d$_6$) 0.77 (s, 9H) 1.33-1.46 (m, 1H) 1.57-1.70 (m, 1H) 2.59 (dd, J = 12.9, 7.2 Hz, 1H) 2.68-2.83 (m, 2H) 2.84-3.02 (m, 2H) 3.06 (s, 6H) 3.53 (s, 3H) 3.55-3.64 (m, 1H) 3.73 (br. s., 1H) 3.89 (d, J = 9.8 Hz, 1H) 3.91 (br. s., 1H) 4.06-4.13 (m, J = 11.7, 3.1 Hz, 1H) 4.18 (d, J = 11.5 Hz, 1H) 4.80 (d, J = 5.3 Hz, 1H) 5.09 (dd, J = 8.3, 3.6 Hz, 1H) 5.29 (br. s., 1H) 6.64 (d, J = 9.8 Hz, 1H) 6.76 (d, J = 8.6 Hz, 1H) 6.96-7.04 (m, 4H) 7.08 (s, 1H) 7.18 (d, J = 8.0 Hz, 2H) 7.16 (dd, J = 8.6, 2.0 Hz, 1H) 7.23-7.32 (m, 1H) 7.65 (d, J = 8.0 Hz, 2H) 7.62 (d, J = 10.6 Hz, 1H) 7.96 (d, J = 8.6 Hz, 1H) |
| 22 | (400 MHz, DMSO-d$_6$) 0.75 (s, 9H) 1.35-1.44 (m, 0H) 1.60-1.70 (m, 1H) 2.55-2.64 (m, 1H) 2.68-2.83 (m, 2H) 2.87-3.01 (m, 2H) 3.09 (s, 6H) 3.49 (s, 3H) 3.60 (br. s., 1H) 3.73 (br. s., 1H) 3.88 (d, J = 9.4 Hz, 1H) 3.92 (br. s., 1H) 4.08 (d, J = 11.3 Hz, 1H) 4.17 (d, J = 11.2 Hz, 1H) 4.83 (d, J = 3.7 Hz, 1H) 5.08 (d, J = 8.4 Hz, 1H) 5.30 (br. s., 1H) 6.64 (d, J = 9.0 Hz, 1H) 6.75 (d, J = 8.6 Hz, 1H) 6.96-7.02 (m, 4H) 7.07 (s, 1H) 7.15 (d, J = 8.6 Hz, 1H) 7.20-7.31 (m, 1H) 7.23 (d, J = 7.2 Hz, 2H) 7.61 (d, J = 8.4 Hz, 1H) 7.74 (d, J = 7.2 Hz, 2H) 7.97 (d, J = 8.4 Hz, 1H) 8.17 (s, 1H) 8.55 (s, 1H) |
| 23 | (400 MHz, DMSO-d$_6$) 0.76 (s, 9H) 1.34-1.45 (m, 1H) 1.60-1.71 (m, 1H) 2.55-2.64 (m, 1H) 2.70-2.85 (m, 2H) 2.87-3.01 (m, 2H) 3.48 (s, 3H) 3.60 (br. s., 1H) 3.74 (br. s., 1H) 3.93 (br. s., 1H) 3.89 (d, J = 10.0 Hz, 1H) 3.94 (s, 3H) 4.09 (d, J = 11.5 Hz, 1H) 4.18 (d, J = 11.2 Hz, 1H) 4.85 (d, J = 4.3 Hz, 1H) 5.09 (d, J = 8.4 Hz, 1H) 5.31 (s, 1H) 6.64 (d, J = 9.6 Hz, 1H) 6.76 (d, J = 8.6 Hz, 1H) 6.96-7.03 (m, 3H) 7.07 (s, 1H) 7.15 (d, J = 8.8 Hz, 1H) 7.24-7.33 (m, 3H) 7.63 (d, J = 9.0 Hz, 1H) 7.82 (d, J = 7.4 Hz, 2H) 7.98 (d, J = 8.4 Hz, 1H) 8.35 (s, 1H) 8.70 (s, 1H) |

TABLE 3-continued

| Comp. N° | ¹H NMR (δ ppm) |
|---|---|
| 25 | (400 MHz, DMSO-d$_6$) 0.77 (s, 9H) 1.35-1.45 (m, 1H) 1.60-1.69 (m, 1H) 2.56-2.64 (m, 1H) 2.71-2.87 (m, 2H) 2.88-3.03 (m, 2H) 3.12 (s, 6H) 3.48 (s, 3H) 3.56-3.64 (m, 1H) 3.70-3.77 (m, 1H) 3.88 (d, J = 9.8 Hz, 1H) 3.92-3.99 (m, 1H) 4.09 (dd, J = 11.4, 2.9 Hz, 1H) 4.18 (d, J = 11.5 Hz, 1H) 4.83 (d, J = 5.3 Hz, 1H) 5.08 (dd, J = 8.0, 2.7 Hz, 1H) 5.29 (d, J = 2.5 Hz, 1H) 6.67 (d, J = 9.6 Hz, 1H) 6.76 (d, J = 8.8 Hz, 1H) 6.96-7.03 (m, 3H) 7.08 (s, 1H) 7.15 (d, J = 8.6 Hz, 1H) 7.24-7.32 (m, 3H) 7.64 (d, J = 9.0 Hz, 1H) 7.87 (d, J = 7.6 Hz, 2H) 7.98 (d, J = 8.6 Hz, 1H) 8.06 (s, 1H) 8.28 (s, 1H) |
| 27 | (400 MHz, DMSO-d$_6$) 0.76 (s, 9H) 1.39-1.48 (m, 1H) 1.60-1.71 (m, 1H) 2.64-3.04 (m, 5H) 3.47 (s, 3H) 3.61 (br. s., 1H) 3.72 (s, 3H) 3.75 (br. s., 1H) 3.87 (d, J = 10.0 Hz, 1H) 3.88 (s, 3H) 3.95 (br. s., 1H) 4.10 (dd, J = 11.9, 3.5 Hz, 1H) 4.19 (d, J = 11.5 Hz, 1H) 4.82 (d, J = 5.3 Hz, 1H) 5.10 (dd, J = 9.0, 3.5 Hz, 1H) 5.26 (d, J = 3.3 Hz, 1H) 6.66 (d, J = 10.0 Hz, 1H) 6.70-6.79 (m, 4H) 6.88 (d, J = 8.6 Hz, 1H) 7.08 (br. s., 1H) 7.11-7.19 (m, 2H) 7.27 (d, J = 8.2 Hz, 2H) 7.43 (d, J = 8.2 Hz, 2H) 7.59 (d, J = 9.2 Hz, 1H) 7.91 (dd, J = 8.6, 2.5 Hz, 1H) 7.92 (d, J = 8.2 Hz, 1H) 8.38 (d, J = 2.1 Hz, 1H) |
| 29 | (400 MHz, DMSO-d$_6$) 0.77 (s, 9H) 1.35-1.44 (m, 1H) 1.60-1.70 (m, 1H) 2.56-2.63 (m, 1H) 2.70-2.82 (m, 2H) 2.87-3.01 (m, 2H) 3.52 (s, 3H) 3.59 (br. s., 1H) 3.74 (br. s., 1H) 3.86-3.95 (m, 2H) 4.07 (s, 3H) 4.10 (d, J = 12.5 Hz, 1H) 4.18 (d, J = 12.5 Hz, 1H) 4.82 (br. s., 1H) 5.09 (d, J = 7.4 Hz, 1H) 5.30 (s, 1H) 6.63 (d, J = 10.0 Hz, 1H) 6.76 (d, J = 8.2 Hz, 1H) 6.96-7.03 (m, 3H) 7.07 (s, 1H) 7.16 (d, J = 9.6 Hz, 1H) 7.22 (d, J = 7.2 Hz, 2H) 7.26-7.30 (m, 1H) 7.32 (s, 1H) 7.62-7.68 (m, 3H) 7.97 (d, J = 9.6 Hz, 1H) |
| 30 | (400 MHz, DMSO-d$_6$) 0.77 (s, 9H) 1.36-1.45 (m, 1H) 1.60-1.70 (m, 1H) 2.55-2.64 (m, 1H) 2.69-2.87 (m, 2H) 2.87-3.03 (m, 2H) 3.47 (s, 3H) 3.56 (s, 1H) 3.61 (d, J = 9.8 Hz, 1H) 3.74 (br. s., 1H) 3.88 (d, J = 10.2 Hz, 1H) 3.95 (br. s., 1H) 3.92 (s, 3H) 4.09 (dd, J = 11.7, 3.3 Hz, 1H) 4.18 (d, J = 11.5 Hz, 1H) 4.88 (br. s., 1H) 5.08 (d, J = 6.1 Hz, 1H) 6.67 (d, J = 10.2 Hz, 1H) 6.76 (d, J = 8.8 Hz, 1H) 6.73 (d, J = 8.2 Hz, 1H) 6.96-7.03 (m, 3H) 7.08 (s, 1H) 7.11-7.19 (m, 1H) 7.25-7.32 (m, 3H) 7.45 (d, J = 7.4 Hz, 1H) 7.65 (d, J = 9.4 Hz, 1H) 7.74 (t, J = 7.7 Hz, 1H) 7.89 (d, J = 8.0 Hz, 2H) 8.04 (d, J = 8.8 Hz, 1H) |
| 31 | (400 MHz, DMSO-d$_6$) 0.76 (s, 9H) 1.35-1.45 (m, 1H) 1.61-1.71 (m, 1H) 2.60 (dd, J = 13.1, 7.4 Hz, 1H) 2.74-2.88 (m, 2H) 2.88-3.02 (m, 2H) 3.44 (s, 3H) 3.60 (br. s., 1H) 3.75 (br. s., 1H) 3.87 (d, J = 9.8 Hz, 1H) 3.92-4.01 (m, 1H) 4.09 (dd, J = 11.7, 3.5 Hz, 1H) 4.18 (d, J = 11.5 Hz, 1H) 4.85 (d, J = 5.5 Hz, 1H) 5.08 (dd, J = 8.6, 3.5 Hz, 1H) 5.31 (d, J = 2.5 Hz, 1H) 6.63 (d, J = 9.6 Hz, 1H) 6.74 (d, J = 8.8 Hz, 1H) 6.75 (none, 1H) 6.95-7.03 (m, 3 H) 7.05 (d, J = 2.0 Hz, 1H) 7.14 (dd, J = 8.7, 2.4 Hz, 1H) 7.24-7.31 (m, 1H) 7.36 (d, J = 8.2 Hz, 2H) 7.63 (d, J = 9.2 Hz, 1H) 7.70 (d, J = 8.2 Hz, 1H) 7.95 (dd, J = 5.3, 1.4 Hz, 1H) 7.98 (d, J = 9.0 Hz, 1H) 8.06 (s, 1H) 8.77 (d, J = 5.1 Hz, 1H) |
| 34 | (400 MHz, DMSO-d$_6$) 0.78 (s, 9H) 1.37-1.51 (m, 1H) 1.61-1.75 (m, 1H) 2.62-2.90 (m, 4H) 2.92-3.01 (m, 1H) 3.04 (s, 6H) 3.18 (s, 3H) 3.37-3.44 (m, 2H) 3.61 (br. s., 1H) 3.68 (br. s., 1H) 3.89 (d, J = 9.6 Hz, 1H) 3.92-3.98 (m, 1H) 3.99-4.09 (m, 3H) 4.13 (d, J = 11.3 Hz, 1H) 4.91 (d, J = 5.1 Hz, 1H) 5.07 (dd, J = 8.4, 2.7 Hz, 1H) 5.21 (d, J = 2.9 Hz, 1H) 6.69 (d, J = 9.0 Hz, 1H) 6.71-6.80 (m, 2H) 6.83 (dd, J = 9.3, 2.4 Hz, 1H) 6.97 (td, J = 8.6, 2.3 Hz, 1H) 7.03-7.15 (m, 2H) 7.17-7.30 (m, 4H) 7.38 (d, J = 8.0 Hz, 2H) 7.62 (d, J = 9.0 Hz, 1H) 7.73 (dd, J = 8.9, 2.1 Hz, 1H) 7.88 (d, J = 9.0 Hz, 1H) 8.33 (d, J = 1.8 Hz, 1H) |
| 54 | (400 MHz, DMSO-d$_6$) 0.80 (s, 9H) 1.38-1.48 (m, 1H) 1.66-1.75 (m, 1H) 2.45 (s, 6H) 2.68-2.77 (m, 2H) 2.78-2.88 (m, 2H) 2.91-3.01 (m, 1H) 3.50 (s, 3H) 3.58 (br. s., 1H) 3.68 (br. s., 1H) 3.90 (d, J = 10.0 Hz, 1H) 3.93-3.99 (m, 1H) 4.17 (dd, J = 11.9, 3.5 Hz, 1H) 4.25 (d, J=11.1 Hz, 1H) 4.89 (d, J = 4.9 Hz, 1H) 5.09 (dd, J = 8.3, 3.6 Hz, 1H) 5.27 (br. s., 1H) 6.74 (d, J = 9.6 Hz, 1H) 6.79 (t, J = 7.8 Hz, 1H) 6.94 (d, J = 7.6 Hz, 1H) 7.06-7.14 (m, 2H) 7.20-7.28 (m, 3H) 7.26 (s, 2H) 7.32 (d, J = 8.4 Hz, 2H) 7.56 (d, J = 8.0 Hz, 2H) 7.66 (d, J = 8.8 Hz, 1H) 7.84 (d, J = 9.0 Hz, 1H) |
| 56 | (400 MHz, DMSO-d$_6$) 0.78 (s, 9H) 1.40-1.49 (m, 1H) 1.66-1.75 (m, 1H) 2.66-2.90 (m, 4H) 2.94-3.03 (m, 1H) 3.48 (s, 3H) 3.60 (br. s., 1H) 3.70 (br. s., 1H) 3.88 (s, 3H) 3.89 (d, J = 10.0 Hz, 1H) 3.92-4.00 (m, 1H) 4.19 (dd, J = 11.7, 3.3 Hz, 1H) 4.27 (d, J = 11.3 Hz, 1H) 4.90 (d, J = 4.5 Hz, 1H) 5.12 (dd, J = 8.7, 3.2 Hz, 1H) 5.35 (br. s., 1H) 6.69 (d, J = 9.6 Hz, 1H) 6.81 (dd, J = 9.1, 2.2 Hz, 1H) 6.88 (d, J = 8.6 Hz, 1H) 7.06-7.14 (m, 2H) 7.21-7.29 (m, 3H) 7.27 (d, J = 8.2 Hz, 2H) 7.43 (d, J = 8.2 Hz, 2H) 7.64 (d, J = 9.2 Hz, 1H) 7.90 (dd, J = 8.6, 2.5 Hz, 1H) 7.94 (d, J = 8.8 Hz, 1H) 8.38 (d, J = 2.1 Hz, 1H) |
| 57 | (400 MHz, DMSO-D$_6$) 0.77 (s, 9H) 1.42-1.54 (m, 1H) 1.65-1.79 (m, 1H) 2.66-2.89 (m, 3H) 2.89-3.06 (m, 2H) 3.17 (s, 3H) 3.39 (d, J = 5.7 Hz, 2H) 3.67 (br. s., 1H) 3.65 (br. s., 1H) 3.90 (d, J = 10.0 Hz, 1H) 3.88 (s, 3H) 3.94-4.09 (m, 4H) 4.13 (d, J = 11.1 Hz, 1H) 4.97 (d, J = 4.9 Hz, 1H) 5.08 (dd, J = 8.8, 3.5 Hz, 1H) 5.22 (br. s., 1H) 6.76 (d, J = 9.2 Hz, 1H) 6.73 (dd, J = 9.0, 4.9 Hz, 1H) 6.83 (d, J = 9.4, 2.5 Hz, 1H) 6.87 (d, J = 8.6 Hz, 1H) 6.95 (td, J = 8.6, 3.0 Hz, 1H) 7.17-7.26 (m, 2H) 7.26-7.32 (m, 3H) 7.35-7.41 (m, 1H) 7.44 (d, J = 8.2 Hz, 2H) 7.63 (d, J = 9.2 Hz, 1H) 7.86 (d, J = 8.8 Hz, 1H) 7.91 (dd, J = 8.8, 2.5 Hz, 1H) 8.39 (d, J = 2.1 Hz, 1H) |
| 58 | (400 MHz, DMSO-d$_6$) 0.76 (s, 9H) 1.40-1.54 (m, 1H) 1.66-1.80 (m, 1H) 2.72-2.88 (m, 3H) 2.87-2.98 (m, 1H) 2.98-3.09 (m, 1H) 3.48 (s, 3H) 3.66 (br. s., 1H) 3.69 (br. s., 1H) 3.88 (s, 3H) 3.89 (d, J = 10.0 Hz, 1H) 3.95-4.04 (m, 1H) 4.08 (dd, J = 11.7, 3.5 Hz, 1H) 4.12-4.25 (m, J = 11.5 Hz, 1H) 4.96 (d, J = 4.9 Hz, 1H) 5.09 (dd, J = 8.6, 3.5 Hz, 1H) 5.31 (br. s., 1H) 6.68 (d, J = 9.6 Hz, 1H) 6.75 (d, J = 8.8 Hz, 1H) 6.88 (d, J = 8.6 Hz, 1H) 7.08 (d, J = 1.8 Hz, 1H) 7.15 (dd, J = 8.8, 2.3 Hz, 1H) 7.19-7.32 (m, 5H) 7.34-7.41 (m, 1H) 7.43 (d, J = 8.0 Hz, 2H) 7.60 (d, J = 9.2 Hz, 1H) 7.91 (dd, J = 8.6, 2.5 Hz, 1H) 7.90 (d, J = 8.2 Hz, 1H) 8.39 (d, J = 2.3 Hz, 1H) |
| 60 | (400 MHz, DMSO-d$_6$) 0.80 (s, 9H) 1.38-1.50 (m, 1H) 1.65-1.77 (m, 1H) 2.62-2.88 (m, 4H) 2.90-3.00 (m, 1H) 2.95 (s, 6H) 3.50 (s, 3H) 3.59 (br. s., 1H) 3.68 (br. s., 1H) 3.89 (d, J = 9.6 Hz, 1H) 3.96 (br. s., 1H) 4.14 (dd, J = 11.5, 3.5 Hz, 1H) 4.21 (d, J = 11.1 Hz, 1H) 4.89 (d, J = 4.5 Hz, 1H) 5.09 (dd, J = 8.8, 3.7 Hz, 1H) 5.27 (br. s., 1H) 6.71-6.83 (m, 3H) |

TABLE 3-continued

| Comp. N° | ¹H NMR (δ ppm) |
|---|---|
| | 6.96-7.05 (m, 1H) 7.05-7.14 (m, 2H) 7.28 (d, J = 8.2 Hz, 2H) 7.20-7.27 (m, 2H) 7.49 (d, J = 8.2 Hz, 2H) 7.65 (d, J = 8.8 Hz, 1H) 7.84 (d, J = 9.0 Hz, 1H) 7.93 (d, J = 2.0 Hz, 1H) 8.42 (d, J = 2.2 Hz, 1H) |
| 61 | (400 MHz, DMSO-$d_6$) 0.77 (s, 9H) 1.39-1.51 (m, 1H) 1.62-1.77 (m, 1H) 2.65-2.90 (m, 4H) 2.98 (d, J = 7.0 Hz, 1H) 3.48 (s, 3H) 3.60 (br. s., 1H) 3.72 (br. s., 1H) 3.88 (s, 3H) 3.84-3.92 (m, 1H) 3.97 (br. s., 1H) 4.18 (dd, J = 11.7, 2.9 Hz, 1H) 4.27 (d, J = 11.5 Hz, 1H) 4.87 (d, J = 4.9 Hz, 1H) 5.11 (dd, J = 8.0, 2.1 Hz, 1H) 5.38 (d, J = 2.9 Hz, 1H) 6.68 (d, J = 9.6 Hz, 1H) 6.88 (d, J = 8.6 Hz, 1H) 6.90 (br. s., 1H) 7.04-7.14 (m, 2H) 7.27 (d, J = 8.0 Hz, 5H) 7.43 (d, J = 7.8 Hz, 2H) 7.60 (d, J = 8.8 Hz, 1H) 7.92 (d, 1H) 7.90 (dd, J = 8.2, 2.3 Hz, 1H) 8.38 (d, J = 1.8 Hz, 1H) |
| 63 | (400 MHz, DMSO-$d_6$) 0.78 (s, 9H) 1.47 (t, J = 10.0 Hz, 1H) 1.74 (t, J = 11.7 Hz, 1H) 2.69-2.87 (m, 3H) 2.87-3.06 (m, 2H) 3.15 (s, 6H) 3.49 (s, 3H) 3.65 (br. s., 1H) 3.68 (br. s., 1H) 3.89 (d, J = 9.6 Hz, 1H) 3.92-4.00 (m, 1H) 4.05 (dd, J = 11.7, 3.7 Hz, 1H) 4.09-4.17 (m, J = 11.5 Hz, 1H) 4.91 (br. s., 1H) 5.08 (dd, J = 9.0, 3.7 Hz, 1H) 5.17 (br. s., 1H) 6.70 (d, J = 9.8 Hz, 1H) 6.73 (dd, J = 9.0, 4.9 Hz, 1H) 6.83 (d, J = 9.7, 3.0 Hz, 1H) 6.95 (td, J = 8.5, 3.0 Hz, 1H) 7.17-7.32 (m, 5H) 7.36-7.40 (m, 1H) 7.41 (d, J = 8.0 Hz, 2H) 7.64 (d, J = 9.0 Hz, 1H) 7.81 (d, J = 9.0 Hz, 1H) 8.59 (s, 2H) |
| 64 | (400 MHz, DMSO-$d_6$) 0.77 (s, 9H) 1.35-1.44 (m, 1H) 1.62-1.72 (m, 1H) 2.61-2.66 (m, 1H) 2.69-2.83 (m, 2H) 2.92-3.03 (m, 2H) 3.48 (s, 3H) 3.57-3.65 (m, 1H) 3.70-3.74 (m, 1H) 3.88 (s, 3H) 3.88 (d, J = 10.0 Hz, 1H) 3.91-3.96 (m, 1H) 4.07 (dd, J = 11.7, 3.7 Hz, 1H) 4.14 (d, J = 11.3 Hz, 1H) 4.85 (d, J = 5.3 Hz, 1H) 5.08 (dd, J = 8.6, 3.5 Hz, 1H) 5.23 (d, J = 2.9 Hz, 1H) 6.67 (d, J = 9.4 Hz, 1H) 6.74 (dd, J = 9.0, 4.9 Hz, 1H) 6.83 (dd, J = 9.4, 2.7 Hz, 1H) 6.88 (d, J = 8.6 Hz, 1H) 6.96 (td, J = 8.4, 3.0 Hz, 1H) 7.14-7.22 (m, 3H) 7.27 (d, J = 8.2 Hz, 2H) 7.35-7.41 (m, 1H) 7.43 (d, J = 8.2 Hz, 2H) 7.64 (d, J = 8.8 Hz, 1H) 7.90 (dd, J = 8.6, 2.5 Hz, 1H) 7.99 (d, J = 8.8 Hz, 1H) 8.38 (d, J = 2.3 Hz, 1H) |
| 65 | (400 MHz, DMSO-$d_6$) 0.77 (s, 9H) 1.35-1.44 (m, 1H) 1.62-1.72 (m, 1H) 2.57-2.65 (m, 1H) 2.65-2.84 (m, 2H) 2.87-3.02 (m, 2H) 3.47 (s, 3H) 3.55-3.63 (m, 1H) 3.74 (br. s., 1H) 3.88 (d, J = 9.6 Hz, 1H) 3.93 (br. s., 1H) 3.95 (s, 3H) 4.07 (dd, J = 11.5, 3.7 Hz, 1H) 4.15 (d, J = 11.3 Hz, 1H) 4.85 (d, J = 5.5 Hz, 1H) 5.09 (dd, J = 8.9, 3.6 Hz, 1H) 5.22 (d, J = 3.1 Hz, 1H) 6.67 (d, J = 9.6 Hz, 1H) 6.73 (dd, J = 8.9, 4.8 Hz, 1H) 6.81 (dd, J = 9.4, 2.7 Hz, 1H) 6.95 (td, J = 8.6, 2.9 Hz, 1H) 6.97-7.04 (m, 3H) 7.24-7.35 (m, 1H) 7.31 (d, J = 8.2 Hz, 2H) 7.51 (d, J = 8.2 Hz, 2H) 7.64 (d, J = 8.8 Hz, 1H) 7.95 (d, J = 8.8 Hz, 1H) 8.83 (s, 2H) |
| 66 | (400 MHz, DMSO-$d_6$) 0.77 (s, 9H) 1.39-1.48 (m, 1H) 1.70-1.78 (m, 1H) 2.19 (s, 3H) 2.69-2.80 (m, 3H) 2.80-2.90 (m, 1H) 2.92-3.01 (m, 1H) 3.48 (s, 3H) 3.68 (br. s., 2H) 3.88 (d, J = 10.0 Hz, 1H) 3.88 (s, 3H) 4.01 (br. s., 1H) 4.01 (dd, J = 11.5, 4.1 Hz, 1H) 4.08 (dd, J = 8.8, 3.5 Hz, 1H) 4.88 (d, J = 4.9 Hz, 1H) 5.05 (d, J = 3.9 Hz, 1H) 5.07 (d, J = 3.1 Hz, 1H) 6.61 (d, J = 8.0 Hz, 1H) 6.65 (d, J = 9.6 Hz, 1H) 6.86-6.92 (m, 3H) 7.06-7.13 (m, 2H) 7.20-7.29 (m, 2H) 7.27 (d, J = 8.2 Hz, 2H) 7.43 (d, J = 8.2 Hz, 2H) 7.61 (d, J = 9.2 Hz, 1H) 7.77 (d, J = 9.0 Hz, 1H) 7.91 (dd, J = 8.6, 2.5 Hz, 1H) 8.39 (d, J = 2.1 Hz, 1H) |
| 67 | (400 MHz, DMSO-$d_6$) 0.78 (s, 9H) 1.41-1.53 (m, 1H) 1.68-1.80 (m, 1H) 2.65-2.87 (m, 3H) 2.87-3.08 (m, 2H) 3.48 (s, 3H) 3.60-3.72 (m, 2H) 3.88 (s, 3H) 3.90 (d, J = 11.5 Hz, 1H) 3.93-4.02 (m, 1H) 4.05 (dd, J = 11.7, 3.5 Hz, 1H) 4.13 (d, J = 11.3 Hz, 1H) 4.96 (d, J = 4.9 Hz, 1H) 5.08 (dd, J = 8.8, 3.5 Hz, 1H) 5.23 (br. s., 1H) 6.69 (d, J = 9.8 Hz, 1H) 6.73 (dd, J = 9.0, 4.9 Hz, 1H) 6.83 (dd, J = 9.4, 3.1 Hz, 1H) 6.88 (d, J = 8.8 Hz, 1H) 6.95 (td, J = 8.5, 3.1 Hz, 1H) 7.18-7.25 (m, 2H) 7.25-7.32 (m, 3H) 7.35-7.41 (m, 1H) 7.44 (d, J = 8.2 Hz, 2H) 7.64 (d, J = 9.4 Hz, 1H) 7.87 (d, J = 9.0 Hz, 1H) 7.91 (dd, J = 8.7, 2.6 Hz, 1H) 8.38 (d, J = 2.1 Hz, 1H) |
| 68 | (400 MHz, DMSO-$d_6$) 1.17-1.38 (m, 2H) 1.39-1.53 (m, 1H) 1.77-1.89 (m, 1H) 2.64-2.94 (m, 5H) 2.95-3.05 (m, 1H) 3.06 (s, 6H) 3.48 (dd, J = 9.6, 5.5 Hz, 1H) 3.52-3.79 (m, 6H) 4.07 (dd, J = 11.9, 3.7 Hz, 1H) 4.15 (d, J = 11.5 Hz, 1H) 4.80 (dt, J = 8.1, 5.7 Hz, 0H) 4.89 (d, J = 4.9 Hz, 1H) 5.10 (dd, J = 8.5, 3.6 Hz, 1H) 5.27 (br. s., 1H) 5.46 (d, J = 5.3 Hz, 1H) 6.71 (d, J = 8.8 Hz, 1H) 6.74 (dd, J = 9.0, 4.9 Hz, 1H) 6.80 (d, J = 9.4, 2.7 Hz, 1H) 6.96 (td, J = 8.5, 2.8 Hz, 1H) 7.08-7.18 (m, 3H) 7.25 (d, J = 8.4 Hz, 2H) 7.24-7.33 (m, 2H) 7.46 (d, J = 8.2 Hz, 2H) 7.77 (dd, J = 9.0, 2.5 Hz, 2H) 7.82 (d, J = 9.0 Hz, 1H) 8.38 (d, J = 2.3 Hz, 1H) |
| 69 | (500 MHz, DMSO-$d_6$) 0.78 (s, 9H), 1.30-1.47 (m, 3H), 1.74 (t, J = 11.4 Hz, 1H), 2.48 (d, J = 4.5 Hz, 3H), 2.59 (dd, J = 13.7, 10.8 Hz, 1H), 2.64-2.84 (m, 4H), 2.90-2.99 (m, 1H), 3.05 (s, 6H), 3.49-3.57 (m, 2H), 3.59-3.72 (m, 3H), 3.83 (dd, J = 9.5, 6.0 Hz, 1H), 4.12 (d, J = 9.5 Hz, 1H), 4.85-4.93 (m, 2H), 5.50 (d, J = 5.2 Hz, 1H), 6.70 (d, J = 8.9 Hz, 1H), 7.01 (t, J = 7.4 Hz, 1H), 7.05-7.10 (m, 1H), 7.12-7.17 (m, 2H), 7.21 (m, 3H), 7.41-7.48 (m, 3H), 7.56-7.78 (m, 2H), 8.38 (d, J = 2.5 Hz, 1H) |
| 70 | (400 MHz, DMSO-$d_6$) 1.17-1.24 (m, 1H) 1.28-1.38 (m, 1H) 1.41-1.50 (m, 1H) 1.73-1.82 (m, 1H) 2.55-2.68 (m, 1H) 2.68-2.83 (m, 3H) 2.89-2.98 (m, 2H) 3.48 (dd, J = 9.6, 5.5 Hz, 1H) 3.53-3.66 (m, 3H) 3.69-3.77 (m, 3H) 3.73 (s, 3H) 3.88 (s, 3H) 4.11 (dd, J = 11.7, 3.3 Hz, 1H) 4.20 (d, J = 11.4 Hz, 1H) 4.77-4.84 (m, 2H) 5.12 (dd, J = 8.6, 2.9 Hz, 1H) 5.32 (d, J = 2.2 Hz, 1H) 5.46 (d, J = 5.1 Hz, 1H) 6.73-6.80 (m, 4H) 6.88 (d, J = 8.6 Hz, 1H) 7.06 (d, J = 1.8 Hz, 1H) 7.09 (d, J = 9.6 Hz, 1H) 7.12-7.22 (m, 2H) 7.29 (d, J = 8.0 Hz, 2H) 7.52 (d, J = 8.2 Hz, 2H) 7.87 (d, J = 8.8 Hz, 1H) 7.95 (dd, J = 8.6, 2.3 Hz, 1H) 8.43 (d, J = 2.3 Hz, 1H) |
| 73 | (400 MHz, DMSO-$d_6$) 1.17-1.37 (m, 2H) 1.41-1.50 (m, 1H) 1.76-1.86 (m, 1H) 2.65-2.86 (m, 4H) 2.94-3.04 (m, 2H) 3.49 (dd, J = 9.6, 5.5 Hz, 1H) 3.53-3.67 (m, 3H) 3.68-3.77 (m, 3H) 3.88 (s, 3H) 4.10 (dd, J = 11.7, 3.3 Hz, 1H) 4.19 (d, J = 11.5 Hz, 1H) 4.76-4.85 (m, 2H) 5.10 (dd, J = 8.5, 3.2 Hz, 1H) 5.29 (d, J = 3.3 Hz, 1H) 5.46 (d, J = 5.3 Hz, 1H) 6.76 (d, J = 8.6 Hz, 1H) 6.88 (d, J = 8.6 Hz, 1H) 7.07 (s, 1H) 7.07 (d, J = 9.3 Hz, 1H) 7.12-7.22 (m, 3H) 7.25 (d, J = 7.8 Hz, 1H) 7.30 (d, J = 8.0 Hz, 2H) 7.41 (t, J = 7.8 Hz, 1H) 7.52 (d, J = 8.2 Hz, 2H) 7.90 (d, J = 8.8 Hz, 1H) 7.95 (dd, J = 8.6, 2.5 Hz, 1H) 8.43 (d, J = 2.3 Hz, 1H) |
| 74 | (400 MHz, DMSO-$d_6$) 1.21-1.46 (m, 3H) 1.74-1.88 (m, 2H) 1.89-2.04 (m, 1H) 2.56-2.95 (m, 8H) 3.49 (dd, J = 9.6, 5.3 Hz, 1H) 3.53-3.81 (m, 6H) 3.88 (s, 3H) 4.72 (d, J = 3.7 |

TABLE 3-continued

| Comp. N° | ¹H NMR (δ ppm) |
|---|---|
| | Hz, 1H) 4.82-4.90 (m, 3H) 5.48 (d, J = 5.3 Hz, 1H) 6.66 (d, J = 5.1 Hz, 1H) 6.89 (d, J = 8.6 Hz, 1H) 7.07-7.21 (m, 4H) 7.29 (d, J = 8.0 Hz, 2H) 7.22-7.29 (m, 2H) 7.53 (d, J = 8.2 Hz, 2H) 7.66 (d, J = 9.0 Hz, 1H) 7.97 (dd, J = 8.7, 2.6 Hz, 1H) 8.44 (d, J = 2.0 Hz, 1H) |
| 78 | (400 MHz, DMSO-d₆) 1.10-1.20 (m, 1H) 1.21-1.36 (m, 1H) 1.46-1.59 (m, 1H) 1.75-1.88 (m, 1H) 2.63-2.75 (m, 1H) 2.75-2.84 (m, 2H) 2.84-2.95 (m, 1H) 2.95-3.07 (m, 2 H) 3.43 (dd, J = 9.5, 5.0 Hz, 1H) 3.49-3.75 (m, 5H) 3.75-3.86 (m, 1H) 3.88 (s, 3H) 4.08 (dd, J = 11.7, 2.9 Hz, 0H) 4.19 (d, J = 11.3 Hz, 0H) 4.67-4.78 (m, 1H) 4.96 (d, J = 4.3 Hz, 1H) 5.03-5.19 (m, 1H) 5.35-5.52 (m, 2H) 6.75 (d, J = 8.8 Hz, 3H) 6.89 (d, J = 8.6 Hz, 1H) 7.01 (s, 1H) 7.14 (dd, J = 8.6, 2.1 Hz, 1H) 7.18 (d, J = 9.6 Hz, 1H) 7.21-7.37 (m, 5H) 7.37-7.46 (m, 1H) 7.52 (d, J = 8.0 Hz, 2H) 7.82 (d, J = 9.2 Hz, 1H) 7.95 (dd, J = 8.5, 2.2 Hz, 1H) 8.43 (d, J = 2.0 Hz, 1H) |
| 79 | (400 MHz, DMSO-d₆) 1.17-1.37 (m, 2H) 1.44-1.53 (m, 1H) 1.76-1.86 (m, 1H) 2.67-2.84 (m, 3H) 2.85-2.93 (m, 1H) 2.94-3.09 (m, 2H) 3.05 (s, 6H) 3.46-3.52 (m, 1H) 3.52-3.80 (m, 6H) 4.05-4.13 (m, 1H) 4.19 (d, J = 11.3 Hz, 1H) 4.75-4.82 (m, 1H) 4.86 (d, J = 4.5 Hz, 1H) 5.10 (br. s., 1H) 5.32 (s, 1H) 5.45 (d, J = 4.7 Hz, 1H) 6.75 (d, J = 8.4 Hz, 1H) 6.70 (d, J = 8.6 Hz, 1H) 7.02-7.19 (m, 5H) 7.21-7.31 (m, 4H) 7.45 (d, J = 7.2 Hz, 2H) 7.77 (d, J = 8.2 Hz, 1H) 7.82 (d, J = 8.8 Hz, 1H) 8.37 (br. s., 1H) |
| 81 | (400 MHz, DMSO-d₆) 1.14-1.26 (m, 1H) 1.26-1.39 (m, 1H) 1.42-1.55 (m, 1H) 1.74-1.87 (m, 1H) 2.64-2.84 (m, 4H) 2.84-2.94 (m, 1H) 2.94-3.09 (m, 1H) 3.45-3.53 (m, 1H) 3.53-3.67 (m, 3H) 3.68-3.79 (m, 3H) 3.88 (s, 3H) 4.18 (dd, J = 11.7, 2.9 Hz, 1H) 4.28 (d, J = 11.3 Hz, 0H) 4.79 (dt, J = 8.0, 5.8 Hz, 0H) 4.87 (d, J = 5.3 Hz, 1H) 5.13 (dd, J = 8.4, 2.9 Hz, 1H) 5.43 (d, J = 3.5 Hz, 0H) 5.46 (d, J = 5.3 Hz, 1H) 6.85-6.92 (m, 2H) 7.07-7.18 (m, 3H) 7.29 (d, J = 8.2 Hz, 2H) 7.22-7.29 (m, 3H) 7.52 (d, J = 8.0 Hz, 2H) 7.86 (d, J = 9.0 Hz, 0H) 7.95 (dd, J = 8.6, 2.5 Hz, 1H) 8.42 (d, J = 2.3 Hz, 1H) |
| 82 | (400 MHz, DMSO-d₆) 0.67 (d, J = 6.4 Hz, 3H) 0.79-0.98 (m, 1H) 1.21-1.66 (m, 9H) 1.67-1.78 (m, 1H) 2.56-2.84 (m, 6H) 3.25 (t, J = 10.5 Hz, 1H) 3.34 (br. s., 1H) 3.47-3.72 (m, 5H) 3.83 (dd, J = 9.6, 6.0 Hz, 1H) 3.88 (s, 3H) 4.25 (d, J = 3.3 Hz, 1H) 4.81 (d, J = 5.1 Hz, 1H) 4.88 (dt, J = 8.2, 5.7 Hz, 1H) 5.50 (d, J = 5.3 Hz, 1H) 6.89 (d, J = 8.8 Hz, 1H) 7.04-7.3 1 (m, J = 8.2 Hz, 2H) 7.04-7.26 (m, 6H) 7.52 (d, J = 8.2 Hz, 2H) 7.96 (dd, J = 8.6, 2.5 Hz, 1H) 8.44 (d, J = 2.5 Hz, 1H) |
| 83 | (500 MHz, DMSO-d₆) 0.73 (d, J = 6.0 Hz, 3H), 0.84 (s, 9H), 0.96-0.99 (m, 1H), 1.35 (t, J = 10.2 Hz, 1H), 1.42-1.45 (m, 1H), 1.49 (t, J = 12.2 Hz, 1H), 1.81-1.71 (m, 3H), 2.56-2.71 (m, 5H), 2.73-2.96 (m, 3H), 3.36-3.40 (m, 1H), 3.44-3.46 (m, 1H), 3.52 (s, 3H), 3.71 (q, J = 3.9 Hz, 1H), 3.84 (q, J = 7.8 Hz, 1H), 3.88 (d, J = 9.8 Hz, 1H), 4.41 (d, J = 3.8 Hz, 1H), 4.86 (d, J = 5.0 Hz, 1H), 6.75 (d, J = 9.6 Hz, 1H), 7.05-7.08 (m, 2H), 7.14 (d, J = 8.8 Hz, 1H), 7.18-7.24 (m, 4H), 7.41 (d, J = 8.1 Hz, 2H), 7.62 (d, J = 8.7 Hz, 1H), 7.92 (s, 1H) |
| 84 | (500 MHz, DMSO-d₆) 0.71 (s, 9H), 0.82 (s, 9H), 1.31 (t, J = 7.3 Hz, 3H), 1.38 (t, J = 10.8 Hz, 1H), 1.52 (t, J = 12.2 Hz, 1H), 2.47 (d, J = 4.4 Hz, 3H), 2.57-2.70 (m, 3H), 2.78 (dd, J = 13.0, 6.4 Hz, 1H), 2.92 (q, J = 7.2 Hz, 1H), 2.99 (m, 1H), 3.43 (d, J = 10.3 Hz, 1H), 3.52 (s, 3H), 3.85 (q, J = 7.8 Hz, 1H), 3.90 (d, J = 9.3 Hz, 1H), 4.05 (d, J = 9.3 Hz, 1H), 5.02 (s, 1H), 6.82 (d, J = 9.6 Hz,H), 6.98 (t, J = 7.5 Hz, 1H), 7.05 (t, J = 9.3 Hz, 1H), 7.12 (t, J = 7.3 Hz, 1H), 7.18 (t, J = 7.2 Hz, 1H), 7.19 (d, J = 8.3 Hz, 2H), 7.41 (d, J = 7.9 Hz, 2H), 7.57 (d, J = 9.3 Hz, 1H), 7.65 (d, J = 8.9 Hz, 1H), 7.81 (q, J = 4.3 Hz, 1H), 7.94 (s, 1H) |
| 87 | (500 MHz, DMSO-d₆) 0.75 (d, J = 6.1 Hz, 3H), 0.87 (s, 9H), 1.07 (dd, J = 8.5, 14.7 Hz, 1H), 1.30-1.48 (m, 2H), 1.48-1.59 (m, 1H), 1.69-1.87 (m, 3H), 2.55-2.70 (m, 2H), 2.70-2.86 (m, 3H), 3.05 (s, 6H), 3.35-3.42 (m, 1H), 3.55 (s, 3H), 3.43-3.59 (m, 1H), 3.69 (d, J = 4.1 Hz, 1H), 3.78-3.97 (m, 2H), 4.40 (d, J = 3.6 Hz, 1H), 4.85 (d, J = 4.9 Hz, 1H), 6.70 (d, J = 8.9 Hz, 1H), 6.77 (d, J = 9.6 Hz, 1H), 6.99-7.30 (m, 7H), 7.50 (d, J = 8.0 Hz, 2H), 7.69 (d, J = 8.9 Hz, 1H), 7.74 (dd, J = 2.6, 8.9 Hz, 1H), 8.35 (d, J = 2.6 Hz, 1H) |
| 88 | (400 MHz, CHLOROFORM-d) 0.91 (s, 18H) 1.64-1.86 (m, 2H) 2.73 (d, J = 4.3 Hz, 3H) 2.75-2.82 (m, 1H) 2.85-2.99 (m, 4H) 3.59 (s, 3H) 3.80-3.91 (m, 2H) 3.96 (s, 3H) 4.04-4.13 (m, 1H) 4.15 (d, J = 8.8 Hz, 1H) 4.25 (br. s., 1H) 5.45 (br. s., 1H) 5.88 (br. s., 1H) 6.44 (d, J = 7.0 Hz, 1H) 6.61 (d, J = 8.6 Hz, 1H) 6.78 (d, J = 8.8 Hz, 1H) 6.85-6.98 (m, 3H) 7.08-7.16 (m, 1H) 7.23 (d, J = 7.8 Hz, 2H) 7.36 (d, J = 7.2 Hz, 2H) 7.70 (d, J = 8.4 Hz, 1H) 8.31 (s, 1H) |
| 89 | (400 MHz, DMSO-d₆) 0.58 (d, J = 6.4 Hz, 3H) 0.81 (s, 9H) 0.81-0.92 (m, 1H) 1.17-1.43 (m, 3H) 1.43-1.66 (m, 5H) 2.57-2.83 (m, 5H) 3.05 (s, 6H) 3.14-3.24 (m, 1H) 3.30 (br. s., 1H) 3.48 (br. s., 1H) 3.51 (s, 3H) 3.81-3.89 (m, 1H) 3.89 (d, J = 9.4 Hz, 1H) 4.22 (d, J = 3.3 Hz, 1H) 4.81 (d, J = 4.7 Hz, 1H) 6.71 (d, J = 8.8 Hz, 1H) 6.79 (d, J = 9.6 Hz, 1H) 7.09 (d, J = 9.6 Hz, 1H) 7.05 (dd, J = 7.6, 1.2 Hz, 1H) 7.15-7.26 (m, 5H) 7.39 (d, J = 8.2 Hz, 2H) 7.61 (d, J = 9.0 Hz, 1H) 7.74 (dd, J = 9.0, 2.5 Hz, 1H) 8.35 (d, J = 2.1 Hz, 1H) |
| 90 | (500 MHz, DMSO-d₆) 0.71 (s, 9H), 0.82 (s, 9H), 1.40 (t, J = 11.5, 1H), 1.53 (t, J = 12.3 Hz, 1H), 2.47 (d, J = 4.4 Hz, 3H), 2.56-2.71 (m, 3H), 2.79 (dd, J = 13.2, 6.8 Hz, 1H), 2.86-2.96 (m, 1H), 3.05 (s, 6H), 3.41-3.49 (m, 1H), 3.52 (s, 3H), 3.86 (q, J = 7.3 Hz, 1H), 3.90 (d, J = 9.3 Hz, 1H), 4.05 (d, J = 9.3 Hz,H), 4.86 (d, J = 4.8 Hz,H), 6.71 (d, J = 8.9 Hz, 1H), 6.83 (d, J = 9.6 Hz, 1H), 6.98 (t, J = 7.5 Hz, 1H), 7.04 (dd, J = 10.5, 8.5 Hz, 1H), 7.11 (t, J = 7.3 Hz, 1H), 7.17-7.21 (m, 3H), 7.40 (d, J = 8.0 Hz, 2H), 7.45 (d, J = 9.5 Hz, 1H), 7.61 (d, J = 8.8 Hz, 1H), 7.72-7.80 (m, 2H), 8.35 (d, J = 2.4 Hz, 1H) |
| 91 | (400 MHz, DMSO-d₆) 0.58 (d, J = 6.4 Hz, 3H) 0.76-0.93 (m, 1H) 0.81 (s, 9H) 1.20-1.34 (m, 2H) 1.35-1.46 (m, 1H) 1.47-1.66 (m, 5H) 2.57-2.89 (m, 5H) 3.21 (t, J = 10.0 Hz, 1H) 3.34 (br. s., 1H) 3.51 (br. s., 1H) 3.50 (s, 3H) 3.88 (s, 3H) 3.89-3.94 (m, 2H) 4.23 (d, J = 2.7 Hz, 1H) 4.87 (d, J = 4.5 Hz, 1H) 6.80 (d, J = 9.8 Hz, 1H) 6.89 (d, J = 8.8 Hz, 1H) 7.15 (d, J = 9.2 Hz, 1H) 7.18-7.23 (m, 3H) 7.25 (d, J = 8.2 Hz, 2H) 7.36 (d, J = 8.0 Hz, 2H) 7.63 (d, J = 8.8 Hz, 1H) 7.93 (dd, J = 8.6, 2.5 Hz, 1H) 8.41 (d, J = 2.3 Hz, 1H) |
| 92 | (400 MHz, CHLOROFORM-d) 0.91 (s, 9H) 0.94 (s, 9H) 1.65-1.76 (m, 1H) 1.76-1.88 (m, 1H) 2.65 (dd, J = 12.2, 5.6 Hz, 1H) 2.84-2.97 (m, 4H) 3.22-3.32 (m, 1H) 3.34 (s, 3H) 3.38-3.44 (m, 2H) 3.44-3.55 (m, 1H) 3.59 (s, 3H) 3.63-3.69 (m, 1H) 3.83 (d, J = 10.4 Hz, 1H) 3.90 (d, J = 9.2 Hz, 1H) 3.97 (s, 3H) 4.10-4.16 (m, 1H) 4.20 (d, J = 8.8 Hz, |

TABLE 3-continued

| Comp. N° | ¹H NMR (δ ppm) |
|---|---|
| | 1H) 4.34 (br. s., 1H) 5.50 (d, J = 8.6 Hz, 1H) 6.18 (br. s., 1H) 6.51 (d, J = 8.8 Hz, 1H) 6.63 (d, J = 8.4 Hz, 1H) 6.71 (d, J = 9.8 Hz, 1H) 6.75-6.85 (m, 2H) 6.78 (d, J = 8.4 Hz, 1H) 7.10 (td, J = 7.8, 6.3 Hz, 1H) 7.23 (d, J = 7.8 Hz, 2H) 7.36 (d, J = 7.8 Hz, 1H) 7.70 (dd, J = 8.4, 1.6 Hz, 1H) 8.31 (d, J = 1.8 Hz, 1H) |
| 93 | (600 MHz, DMSO-$d_6$) δ ppm 0.81(s, 9H), 1.43 (ddd, J = 13.2, 10.9, 3.2 Hz, 1H), 1.68 (t, J = 11.9 Hz, 1H), 1.74-1.83 (m, 1H), 1.90-2.00 (m, 1H), 2.63 (dt, J = 16.4, 4.7 Hz, 1H), 2.66-2.74 (m, 2H), 2.78-2.86 (m, 3H), 2.86-2.92 (m, 1H), 3.50 (s, 3H), 3.55 (br. d, J = 10.0 Hz, 1H), 3.77 (br. s., 1H), 3.85-3.89 (m, 1H), 3.89 (s, 3H), 3.96 (br. q, J = 7.8, 7.8, 7.8 Hz, 1H), 4.50 (d, J = 3.7 Hz, 1H), 4.74 (br. s, 1H), 4.84 (br. d, J = 8.9 Hz, 1H), 6.58 (s, 1H), 6.64 (d, J = 5.2 Hz, 1H), 6.87 (d, J = 8.6 Hz, 1H), 7.04-7.10 (m, 2H), 7.12 (d, J = 5.2 Hz, 1H), 7.20-7.23 (m, 1H), 7.24-7.27 (m, 1H), 7.28 (d, J = 7.8 Hz, 2H), 7.47 (d, J = 7.8 Hz, 2H), 7.50 (d, J = 9.1 Hz, 1H), 7.58 (d, J = 8.8 Hz, 1H), 7.92 (dd, J = 8.6, 2.6 Hz, 1H), 8.40 (d, J = 2.6 Hz, 1H) |
| 94 | (400 MHz, DMSO-$d_6$) 0.59 (d, J = 6.4 Hz, 3H) 0.80 (s, 9H) 0.82-0.93 (m, 1H) 1.21-1.41 (m, 3H) 1.46-1.67 (m, 5H) 2.54-2.66 (m, 2H) 2.74-2.90 (m, 3H) 3.20 (t, J = 10.3 Hz, 1H) 3.34 (br. s., 1H) 3.47 (br. s., 1H) 3.49 (s, 3H) 3.83-3.91 (m, 2H) 3.88 (s, 3H) 4.25 (d, J = 3.5 Hz, 1H) 4.81 (d, J = 5.1 Hz, 1H) 6.75 (d, J = 9.6 Hz, 1H) 6.89 (d, J = 8.6 Hz, 1H) 7.10 (s, 1H) 7.15 (d, J = 7.2 Hz, 2H) 7.25 (d, J = 8.2 Hz, 3H) 7.36 (t, J = 8.0 Hz, 1H) 7.46 (d, J = 8.2 Hz, 2H) 7.63 (d, J = 8.8 Hz, 1H) 7.94 (dd, J = 8.7, 2.6 Hz, 1H) 8.41 (d, J = 2.1 Hz, 1H) |
| 96 | (400 MHz, DMSO-$d_6$) 0.58 (d, J = 6.4 Hz, 3H) 0.81 (s, 9H) 0.80-0.88 (m, 1H) 1.21-1.65 (m, 8H) 2.59-2.84 (m, 5H) 3.15-3.24 (m, 1H) 3.29-3.36 (m, 1H) 3.48 (br. s., 1H) 3.49 (s, 3H) 3.83-3.89 (m, 2H) 3.88 (s, 3H) 4.22 (d, J = 3.3 Hz, 1H) 4.82 (d, J = 4.9 Hz, 1H) 6.78 (d, J = 9.4 Hz, 1H) 6.89 (d, J = 8.6 Hz, 1H) 7.05 (dd, J = 7.4, 1.2 Hz, 1H) 7.09 (d, J = 9.4 Hz, 1H) 7.15-7.27 (m, 3H) 7.24 (d, J = 8.2 Hz, 2H) 7.45 (d, J = 8.2 Hz, 2H) 7.62 (d, J = 9.0 Hz, 1H) 7.93 (dd, J = 8.6, 2.5 Hz, 1H) 8.40 (d, J = 2.1 Hz, 1H) |
| 98 | (400 MHz, DMSO-$d_6$) 0.72 (s, 9H) 0.82 (s, 9H) 1.38-1.48 (m, 1H) 1.53-1.62 (m, 1H) 2.62-2.74 (m, 2H) 2.75-2.86 (m, 2H) 2.89-2.98 (m, 1H) 3.02-3.18 (m, 2H) 3.21 (s, 3H) 3.25 (t, J = 5.9 Hz, 2H) 3.51 (s, 3H) 3.48 (br. s., 1H) 3.88 (s, 3H) 3.91 (d, J = 9.6 Hz, 2H) 4.12 (d, J = 9.6 Hz, 1H) 4.93 (br. s., 1H) 6.84 (d, J = 9.6 Hz, 1H) 6.90 (d, J = 8.6 Hz, 1H) 7.09-7.21 (m, 3H) 7.25 (d, J = 8.0 Hz, 2H) 7.35 (d, J = 7.8 Hz, 1H) 7.43 (d, J = 10.0 Hz, 1H) 7.46 (d, J = 8.0 Hz, 2H) 7.64 (d, J = 8.8 Hz, 1H) 7.94 (dd, J = 8.5, 2.6 Hz, 1H) 7.94 (br. s., 1H) 8.41 (d, J = 2.1 Hz, 1H) |
| 99 | (400 MHz, DMSO-$d_6$) δ ppm 0.72 (d, J = 6.0 Hz, 3H) 0.80 (s, 9H) 0.90-1.03 (m, 1H) 1.31-1.47 (m, 2H) 1.47-1.59 (m, 1H) 1.66-1.85 (m, 3H) 2.58-2.69 (m, 2H) 2.71-2.85 (m, 3H) 3.35-3.43 (m, 1H) 3.44-3.52 (m, 1H) 3.49 (s, 3H) 3.65-3.72 (m, 1H) 3.83-3.93 (m, 2H) 3.88 (s, 3H) 4.40 (d, J = 3.7 Hz, 1H) 4.86 (d, J = 5.1 Hz, 1H) 6.76 (d, J = 9.4 Hz, 1H) 6.89 (d, J = 8.8 Hz, 1H) 7.08 (d, J = 6.6 Hz, 2H) 7.12-7.23 (m, 3H) 7.25 (d, J = 8.2 Hz, 2H) 7.45 (d, J = 8.2 Hz, 2H) 7.62 (d, J = 8.6 Hz, 1H) 7.93 (dd, J = 8.7, 2.6 Hz, 1H) 8.41 (d, J = 2.3 Hz, 1H) |
| 100 | (400 MHz, DMSO-$d_6$) δ ppm 0.81 (s, 9H) 0.99-1.67 (m, 10H) 2.55-2.87 (m, 5H) 3.36-3.46 (m, 2H) 3.46-3.50 (m, 1H) 3.50 (s, 3H) 3.80-3.93 (m, 2H) 3.88 (s, 3H) 4.42 (d, J = 2.7 Hz, 1H) 4.86 (d, J = 4.3 Hz, 1H) 6.79 (d, J = 9.6 Hz, 1H) 6.89 (d, J = 8.6 Hz, 1H) 7.01-7.13 (m, 2H) 7.13-7.24 (m, 3H) 7.25 (d, J = 7.8 Hz, 2H) 7.47 (d, J = 7.6 Hz, 2H) 7.61 (d, J = 8.4 Hz, 1H) 7.95 (d, J = 8.6 Hz, 1H) 8.35-8.50 (m, 1H) |
| 102 | (400 MHz, DMSO-$d_6$) 0.78 (s, 9H) 1.38-1.51 (m, 1H) 1.63-1.75 (m, 1H) 2.10 (s, 3H) 2.63-2.88 (m, 4H) 2.96 (m, J = 6.8 Hz, 1H) 3.48 (s, 3H) 3.61 (br. s., 1H) 3.69 (br. s., 1H) 3.88 (s, 3H) 3.89-3.91 (m, 1H) 3.93 (br. s., 1H) 4.06-4.17 (m, 2H) 4.87 (d, J = 4.5 Hz, 1H) 5.03-5.10 (m, 1H) 5.15 (br. s., 1H) 6.61-6.72 (m, 2H) 6.88 (d, J = 8.4 Hz, 1H) 6.84-6.90 (m, 1H) 7.03-7.14 (m, 2H) 7.20-7.31 (m, 4H) 7.42 (s, 2H) 7.62 (d, J = 9.0 Hz, 1H) 7.84 (d, J = 8.8 Hz, 1H) 7.90 (dd, J = 8.6, 2.5 Hz, 1H) 8.38 (d, J = 2.3 Hz, 1H) |

BIOLOGICAL EXAMPLES

General Antiviral Assay

MT4-LTR-EGFP cells were obtained by transfecting MT4 cells with a selectable construct encompassing the sequences coding for the HIV long terminal repeat (LTR) as a promoter for the expression of enhanced green fluorescent protein (EGFP) and subsequent selection of permanently transfected cells.

The antiviral activity on different HIV-1 strains, was determined in a cell-based virus replication assay. Here MT4-LTR-EGFP cells (150,000 cells/ml) are infected (multiplicity of infection [MOI] of 0.0025) in the presence or absence of different inhibitor concentrations. Two methodologies for read-out were used, either quantification of GFP-fluoresence on day 3 post-infection, or quantification of cell-viability using rezazurin (as described by Fields, R. D., and M. V. Lancaster (1993) Am. Biotechnol. Lab. 11:48-50) on day 4 post infection. Both methods showed similar dose-respons curves from which EC50s could be determined

General Toxicity Assay

The toxicity of inhibitors is determined in parallel on mock-infected MT4 cells (150,000 cells/ml) stably transformed with a CMV-EGFP reporter gene and cultured in the presence or absence of test compound concentrations. Two methodologies for read-out were used, either quantification of GFP-fluoresence on day 3, or quantification of cell-viability using rezazurin on day 4. Both methods showed similar dose-response curves from which CC50s could be determined

50% HS-Rezazurin

For the Antiviral assay in the presence of 50% human serum MT-4 cells were infected with HIV-1 IIIB at a MOI of 0.001 to 0.01 CCID50/cell in RPMI1640 medium. Following 1 h of incubation, cells were washed and plated into a 96-well plate containing serial dilutions of compound in the presence of 10% fetal calf serum (FCS), or 50% human serum. After 4 days incubation, the EC50 in the presence of 50% human serum was determined by a cell viability assay using resazurin.

In the following Table, Strains A, B, and C are clinical isolates that include the following protease inhibitor resistance mutations in the protease domain (background mutations are not mentioned).

TABLE 4

In the following Table, Strains A, B, and C are clinical isolates that include the following protease inhibitor resistance mutations in the protease domain (background mutations are not mentioned).

| | | |
|---|---|---|
| B | M046I | I050V |
| A | M046I | I084V |
| C | G048G/V | V082A |

The last column lists the results for the wild-type strain IIB in the presence of 50% human serum MT-4 cells.

| Comp. N° | HIV-IIIB nM | TOX-MT4CMV μM | TOX-MT4LTR μM | A EC$_{50}$, nM | B EC$_{50}$, nM | C EC$_{50}$, nM | HIV-IIIB + 50% HS EC50, nM |
|---|---|---|---|---|---|---|---|
| 1 | 7.7 | >32 | | 5.7 | 4.8 | 3.7 | 39.3 |
| 2 | 3.0 | >32 | | 3.3 | 2.2 | 1.1 | 19.7 |
| 3 | 2.6 | >32 | | 2.3 | 3.5 | 2.4 | 13.6 |
| 4 | 5.6 | >32 | | 3.9 | 3.9 | 2.7 | 31.2 |
| 5 | 4.7 | >32 | | 5.4 | 4.4 | 5.1 | 28.6 |
| 6 | 3.2 | >32 | | 3.9 | 2.7 | 1.5 | 15.2 |
| 7 | 1.6 | >32 | >49 | 1.5 | 0.9 | 0.8 | 10.4 |
| 8 | 1.8 | >32 | >49 | 2.0 | 1.2 | 1.0 | 12.4 |
| 9 | 8.8 | >27 | | 8.8 | 6.6 | 3.7 | 31.7 |
| 10 | 3.2 | >32 | | 4.0 | 2.5 | 1.7 | 20.1 |
| 11 | 4.2 | >32 | | 3.9 | 3.5 | 2.1 | 22.4 |
| 12 | 4.0 | >32 | | 3.7 | 3.0 | 2.2 | 35.7 |
| 13 | 4.7 | >32 | | 4.6 | 3.0 | 2.4 | 22.6 |
| 14 | 3.0 | >32 | | 3.5 | 2.1 | 1.3 | 24.6 |
| 15 | 2.0 | >32 | | 2.1 | 1.2 | 1.3 | 8.7 |
| 16 | 2.5 | >32 | | 2.0 | 1.3 | 1.1 | 6.6 |
| 17 | 1.9 | >32 | | 2.0 | 1.2 | 1.1 | 6.4 |
| 18 | 2.7 | >32 | >32 | 3.0 | 2.0 | 1.6 | 14.0 |
| 19 | 5.3 | >27 | | 3.7 | 2.4 | 1.8 | 22.1 |
| 20 | 3.1 | 6 | | 7.4 | 3.1 | 2.7 | 11.2 |
| 21 | 6.1 | >32 | | 3.8 | 3.2 | 3.6 | 34.9 |
| 22 | 3.8 | >32 | | 3.5 | 2.6 | 2.1 | 26.4 |
| 23 | 3.0 | 19 | | 3.7 | 2.4 | 2.0 | 12.3 |
| 24 | 3.3 | >32 | | 3.3 | 1.9 | 1.7 | 16.1 |
| 25 | 4.9 | >32 | | 4.6 | 2.7 | 2.5 | 26.4 |
| 26 | 5.0 | >32 | | 4.2 | 3.4 | 3.2 | 15.4 |
| 27 | 3.1 | >32 | >32 | 2.8 | 2.2 | 1.6 | 10.7 |
| 28 | 3.2 | >32 | | 3.1 | 2.1 | 1.4 | 22.5 |
| 29 | 5.5 | 10 | | 6.6 | 3.4 | 3.1 | 13.7 |
| 30 | 4.0 | >32 | | 5.9 | 2.8 | 2.5 | 17.4 |
| 31 | 7.0 | >32 | | 5.0 | 3.2 | 3.4 | 26.4 |
| 32 | 5.9 | 2.2 | | 5.0 | 3.7 | 3.1 | 28.6 |
| 33 | 2.5 | >32 | | 1.5 | 1.0 | 0.9 | 9.8 |
| 34 | 2.7 | >32 | >32 | 2.0 | 1.5 | 1.3 | 10.0 |
| 35 | 2.1 | >32 | >32 | 4.0 | 2.2 | 2.0 | 8.4 |
| 36 | 2.9 | >32 | >32 | 2.4 | 1.4 | 1.3 | 14.3 |
| 37 | 1.7 | >32 | >32 | 2.5 | 0.9 | 0.8 | 4.6 |
| 38 | 7.1 | 10 | | 4.4 | 3.6 | 2.6 | 37.9 |
| 39 | 3.0 | >32 | >32 | 3.9 | 2.1 | 1.3 | 16.4 |
| 40 | 2.4 | >32 | >32 | 1.6 | 1.0 | 0.8 | 11.2 |
| 41 | 3.0 | >32 | >32 | 2.4 | 1.2 | 1.1 | 10.5 |
| 42 | 4.2 | >32 | >32 | 7.2 | 4.1 | 3.9 | 23.7 |
| 43 | 2.0 | | >32 | 1.7 | 1.0 | 1.1 | 10.6 |
| 44 | 3.2 | | >32 | 3.2 | 2.2 | 2.0 | 13.7 |
| 45 | 3.5 | | >32 | 1.2 | 0.8 | 0.7 | 5.2 |
| 46 | 5.3 | | 10 | 9.4 | 5.6 | 3.7 | 34.6 |
| 47 | 3.2 | | >32 | 11.1 | 6.8 | 5.5 | 10.4 |
| 48 | 3.8 | | >32 | 2.6 | 2.2 | 1.3 | 7.5 |
| 49 | 4.1 | | >32 | 5.2 | 3.5 | 2.9 | 19.0 |
| 50 | 2.8 | | >32 | 2.0 | 1.4 | 1.1 | 6.9 |
| 51 | 3.0 | | >32 | 2.3 | 1.5 | 1.3 | 7.0 |
| 52 | 1.8 | | >32 | 1.2 | 0.9 | 0.7 | 6.2 |
| 53 | 2.3 | | >32 | 4.1 | 2.0 | 2.0 | 9.5 |
| 54 | 4.8 | | >32 | 2.7 | 2.1 | 1.6 | 19.8 |
| 55 | 2.7 | | >32 | 2.1 | 1.5 | 1.2 | 12.5 |
| 56 | 2.6 | | >32 | 1.4 | 1.2 | 0.7 | 8.4 |
| 57 | 1.9 | | >32 | 1.9 | 0.9 | 0.8 | 8.7 |
| 58 | 3.9 | | >32 | 6.0 | 2.5 | 1.8 | 13.3 |
| 59 | 1.2 | | >32 | 0.9 | 0.6 | | 5.8 |
| 60 | 4.1 | | 10 | 2.6 | 1.9 | 1.2 | 25.2 |
| 61 | 4.1 | | >32 | 3.0 | 2.1 | 1.6 | 16.1 |
| 62 | 3.2 | | >32 | 2.2 | 1.5 | 0.9 | 16.3 |
| 63 | 1.5 | | >32 | 1.2 | 0.7 | 0.6 | 9.4 |
| 64 | 2.6 | | >32 | 3.0 | 1.6 | 1.3 | 15.1 |
| 65 | 9.1 | | >32 | 4.5 | 3.6 | 2.3 | 24.7 |
| 66 | 0.9 | | >32 | 0.8 | 0.8 | 0.5 | 7.7 |
| 67 | 2.9 | >32 | >32 | 2.1 | 1.2 | 1.0 | 5.3 |
| 68 | 3.0 | >32 | | 2.2 | 1.5 | 1.3 | 9.4 |
| 69 | 11.6 | >32 | | 11.6 | 7.0 | 5.7 | 26.6 |
| 70 | 2.6 | >32 | >32 | 1.6 | 1.6 | 1.2 | 11.4 |
| 71 | 2.1 | >32 | >32 | 2.2 | 2.3 | 1.0 | 10.9 |
| 72 | 1.5 | | >32 | 0.8 | 0.8 | 0.5 | 5.8 |
| 73 | 3.3 | | >32 | 3.7 | 4.1 | 1.9 | 9.2 |
| 74 | 0.9 | | >32 | 0.8 | 0.6 | 0.4 | 3.5 |
| 75 | 2.4 | | >32 | 1.4 | 0.9 | 0.8 | 9.3 |
| 76 | 2.9 | | >32 | 1.7 | 1.5 | 1.1 | 20.5 |
| 77 | 1.9 | | >32 | 1.6 | 1.0 | 0.7 | 6.5 |
| 78 | 2.1 | | >32 | 1.9 | 1.4 | 0.9 | 10.6 |
| 79 | 1.7 | | >32 | 1.1 | 1.0 | 0.7 | 12.8 |
| 80 | 2.4 | | >32 | 1.5 | 1.1 | 0.8 | 10.9 |
| 81 | 4.1 | | >32 | 2.8 | 2.4 | 1.3 | 13.4 |
| 82 | 1.8 | | >27 | 1.1 | 0.8 | 0.7 | 5.1 |
| 83 | 4.0 | >32 | | 8.3 | 2.5 | 2.7 | 14.3 |
| 84 | 6.4 | >32 | | 4.7 | 3.3 | 2.4 | 28.0 |
| 85 | 2.9 | >32 | >32 | 3.0 | 1.3 | 1.1 | 17.5 |
| 86 | 2.6 | | >32 | 7.5 | 1.4 | 1.3 | 17.1 |
| 87 | 4.7 | >32 | | 8.0 | 1.9 | 5.4 | 14.4 |
| 88 | 3.4 | >32 | | 4.8 | 2.8 | 3.0 | 9.9 |
| 89 | 1.1 | >32 | >32 | 1.1 | | 0.8 | 4.9 |
| 90 | 4.7 | >32 | | 4.8 | 2.6 | 2.8 | 13.6 |
| 91 | 1.1 | 17 | 16 | 2.6 | 0.7 | 1.0 | 3.2 |
| 92 | 2.6 | >32 | >32 | 4.2 | 1.8 | 2.9 | 8.4 |
| 93 | 1.3 | >32 | >32 | 0.8 | 0.6 | 0.4 | 3.5 |
| 94 | 0.9 | | >32 | 1.9 | 0.8 | 1.4 | 7.1 |
| 95 | 1.5 | | 23 | 2.2 | 1.3 | 1.0 | 5.9 |
| 96 | 0.9 | | >32 | 0.7 | 0.4 | 0.5 | 2.0 |
| 97 | 5.6 | | >32 | 4.7 | 2.8 | 2.0 | 12.7 |
| 98 | 2.1 | | >32 | 3.7 | 1.0 | 2.2 | 11.2 |
| 99 | 1.1 | | >32 | 1.7 | 0.6 | 0.9 | 3.3 |
| 100 | 1.8 | | >32 | 1.8 | 0.7 | 0.6 | 5.9 |
| 101 | 2.8 | | >32 | 2.5 | 2.4 | 1.7 | 9.8 |
| 102 | 2.3 | | >32 | 5.4 | 3.3 | 1.5 | 6.8 |
| LPV | 13 | 20 | >32 | 110 | 320 | 31 | 61 |
| ATV | 7.6 | 26 | >32 | 59 | 3.3 | 62 | 16 |

LPV = lopinavir
ATV = atazanavir

The invention claimed is:

1. A compound formula I:

(I)

wherein

R$^1$ is halo, C$_{1-4}$alkoxy, trifluoromethoxy;

$R^2$ is a group of formula:

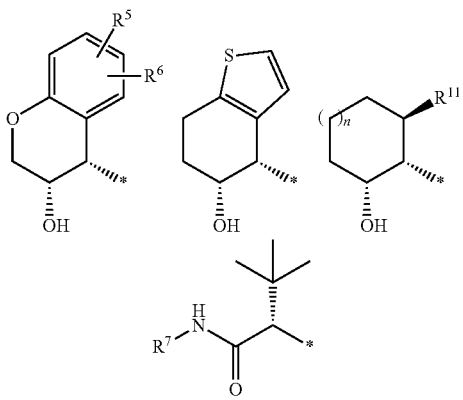

$R^3$ is a group of formula:

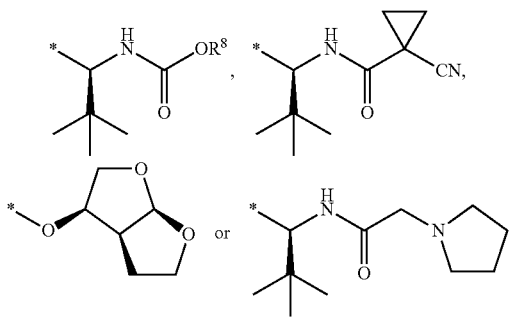

$R^4$ is a group of formula:

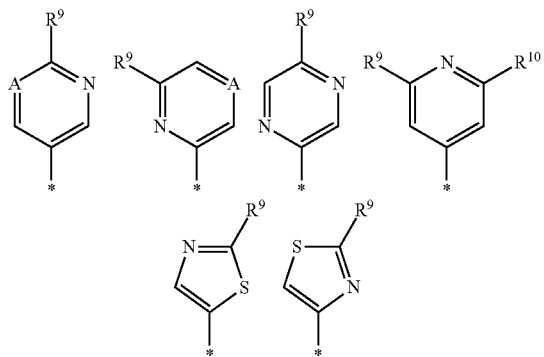

n is 0 or 1;
each A independently is CH or N;
$R^5$ and $R^6$ independently are hydrogen, $C_{1-4}$alkyl, or halo;
$R^7$ is $C_{1-4}$alkyl or $C_{1-4}$alkoxy$C_{1-4}$-alkyl;
$R^8$ is $C_{1-4}$-alkyl or $C_{1-4}$-alkoxy$C_{1-4}$-alkyl;
each $R^9$ independently is $C_{1-4}$alkyl, cyclopropyl, trifluoromethyl, $C_{1-4}$alkoxy, or dimethylamino;
$R^{10}$ is hydrogen, $C_{1-4}$alkyl, cyclopropyl, trifluoromethyl, $C_{1-4}$alkoxy, or dimethylamino;
$R^{11}$ is hydrogen or $C_{1-4}$alkyl;
the pharmaceutically acceptable addition salts and the pharmaceutically acceptable solvates thereof.

2. The compound of claim 1 wherein $R^1$ is halo or methoxy.

3. The compound of claim 1 wherein $R^1$ is fluoro or chloro; which fluoro or chloro is substituted in ortho position; or $R^1$ is methoxy; which methoxy is substituted in meta position.

4. The compound of any of claim 1, wherein $R^2$ is a group of formula

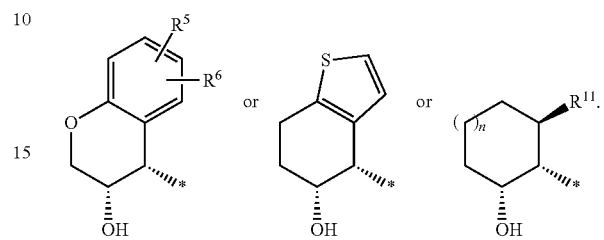

5. The compound of claim 1, wherein $R^2$ is a group of formula

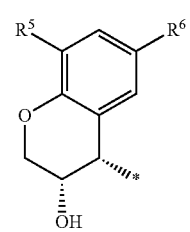

6. The compound of claim 1, wherein $R^5$ is hydrogen, and $R^6$ is halo or $C_{1-4}$alkyl; $R^5$ is halo and $R^6$ is hydrogen; $R^5$ is halo or $C_{1-4}$alkyl, and $R^6$ is hydrogen; or $R^5$ and $R^6$ are both hydrogen, or are both halo; $R^{11}$ is $C_{1-4}$alkyl.

7. The compound of claim 1, wherein $R^5$ is hydrogen and $R^6$ is fluoro or chloro; $R^5$ is fluoro or chloro and $R^6$ is hydrogen; $R^5$ is hydrogen and $R^6$ is methyl; $R^5$ and $R^6$ are both hydrogen, or $R^5$ is chloro and $R^6$ is fluoro; more in particular wherein $R^5$ is hydrogen and $R^6$ is fluoro; $R^5$ is chloro and $R^6$ is hydrogen; $R^5$ is hydrogen and $R^6$ is methyl; $R^5$ and $R^6$ are both hydrogen, or $R^5$ is chloro and $R^6$ is fluoro; and $R^{11}$ is methyl.

8. The compound of any of claim 1, wherein $R^3$ is a group of formula

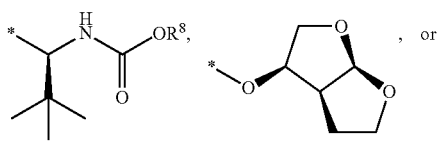

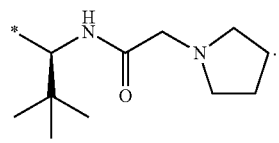

9. The compound of any of claim 1, wherein $R^3$ is a group of formula

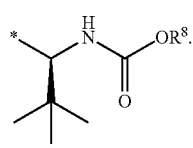

10. The compound of claim 9 wherein $R^8$ is methyl or 2-methoxyethyl.

11. The compound of claim 1 wherein $R^9$ is $C_{1-2}$alkoxy or dimethylamino.

12. The compound of any of claim 1, wherein $R^4$ is a group having the chemical structure specified in claim 1, but wherein in the first group $R^9$ is $R^{9a}$ in the second group $R^9$ is $R^{9b}$ in the third group $R^9$ is $R^{9c}$ in the fourth group $R^9$ is $R^{9d}$ in the fifth and in the sixth group $R^9$ is $R^{9e}$; which groups can be represented as follows:

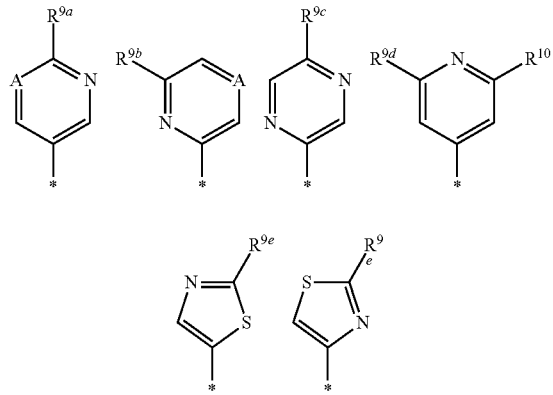

wherein each A independently is CH or N; or wherein each A is CH;

$R^{9a}$ is $C_{1-4}$alkoxy or dimethylamino;

$R^{9b}$ is $C_{1-4}$-alkoxy or dimethylamino;

$R^{9c}$ is $C_{1-4}$alkoxy or dimethylamino;

$R^{9d}$ is $C_{1-4}$alkyl, cyclopropyl, trifluoromethyl;

$R^{10}$ is hydrogen, $C_{1-4}$alkyl, cyclopropyl, or trifluoromethyl; or $R^{10}$ is hydrogen, methyl, cyclopropyl, or trifluoromethyl;

each $R^{9e}$ independently is $C_{1-4}$alkyl, cyclopropyl, $C_{1-4}$alkoxy, or dimethylamino.

13. The compound of claim 12 wherein in $R^{9a}$, $R^{9b}$, $R^{9c}$, $R^{9d}$, or $R^{9e}$ $C_{1-4}$alkoxy is methoxy and $C_{1-4}$alkyl is methyl.

14. The compound of any of claim 1 wherein $R^4$ is:

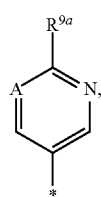

wherein A is CH and $R^{9a}$ is methoxy or dimethylamino.

15. The compound of claim 1 having the formula

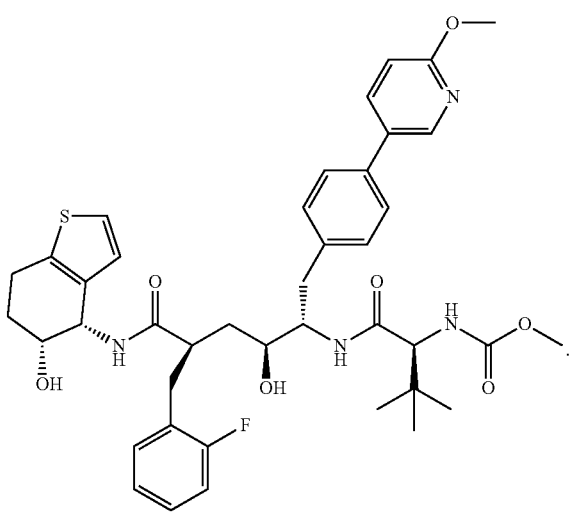 [SMILES: COC(=O)N[C@H](C(=O)N[C@@H](Cc1ccc(-c2ccc(OC)nc2)cc1)[C@@H](O)C[C@@H](Cc1ccccc1F)C(=O)N[C@H]1c2ccsc2CC[C@H]1O)C(C)(C)C]

16. The compound of claim 1 having the formula

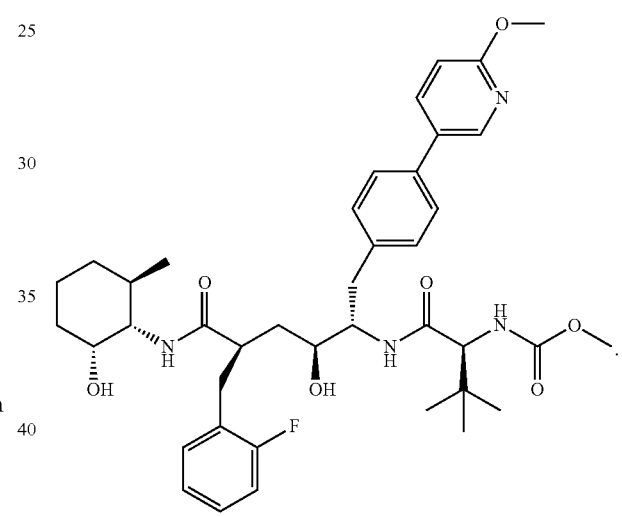

17. The compound of claim 1 having the formula

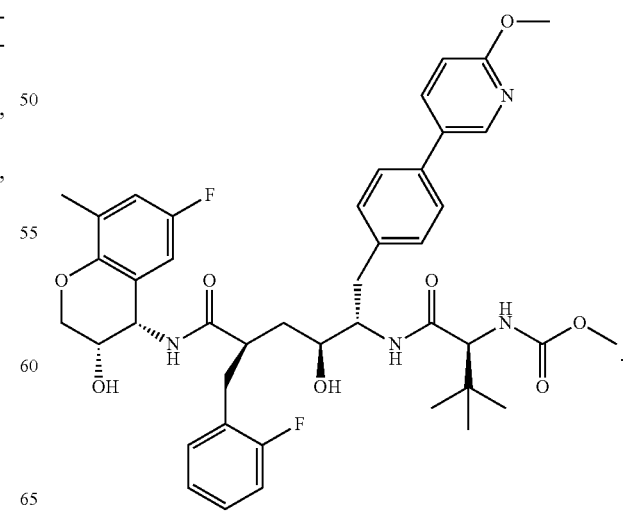

18. A pharmaceutical composition comprising an effective amount of a compound of formula I as defined in claim 1 and a carrier.

19. A pharmaceutical composition comprising an effective amount of a compound of formula I as defined in claim 15 and a carrier.

20. A pharmaceutical composition comprising an effective amount of a compound of formula I as defined in claim 16 and a carrier.

21. A pharmaceutical composition comprising an effective amount of a compound of formula I as defined in claim 17 and a carrier.

\* \* \* \* \*

UNITED STATES PATENT AND TRADEMARK OFFICE
CERTIFICATE OF CORRECTION

PATENT NO. : 8,592,429 B2
APPLICATION NO. : 13/515187
DATED : November 26, 2013
INVENTOR(S) : Kalayanov et al.

It is certified that error appears in the above-identified patent and that said Letters Patent is hereby corrected as shown below:

On the title page item (57) Abstract line 4 and line 5, "allyl" change to "alkyl"

Signed and Sealed this
Fifth Day of August, 2014

Michelle K. Lee
*Deputy Director of the United States Patent and Trademark Office*